(12) United States Patent
Zhou et al.

(10) Patent No.: US 8,637,507 B2
(45) Date of Patent: Jan. 28, 2014

(54) BICYCLIC COMPOUNDS AS INHIBITORS OF DIACYLGLYCEROL ACYLTRANSFERASE

(75) Inventors: Gang Zhou, Bridgewater, NJ (US); Grant Wishart, Lanarkshire (GB); Pauline C. Ting, New Providence, NJ (US); Robert G. Aslanian, Rockaway, NJ (US); Nicolas Zorn, Short Hills, NJ (US); David Won-shik Kim, North Bergen, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 196 days.

(21) Appl. No.: 13/203,983

(22) PCT Filed: Mar. 16, 2010

(86) PCT No.: PCT/US2010/027443
§ 371 (c)(1),
(2), (4) Date: Aug. 31, 2011

(87) PCT Pub. No.: WO2010/107765
PCT Pub. Date: Sep. 23, 2010

(65) Prior Publication Data
US 2011/0319403 A1 Dec. 29, 2011

Related U.S. Application Data

(60) Provisional application No. 61/161,212, filed on Mar. 18, 2009.

(51) Int. Cl.
*C07D 413/04* (2006.01)
*C07D 413/14* (2006.01)
*A61K 31/538* (2006.01)

(52) U.S. Cl.
USPC ........................................ 514/230.5; 544/105

(58) Field of Classification Search
USPC ........................................ 544/105; 514/230.5
See application file for complete search history.

(56) References Cited

U.S. PATENT DOCUMENTS

| | | | |
|---|---|---|---|
| 4,026,891 A | | 5/1977 | Austel et al. |
| 4,621,084 A * | | 11/1986 | Takaya et al. ............... 514/224.2 |
| 5,061,705 A | | 10/1991 | Wuest et al. |
| 6,294,503 B1 * | | 9/2001 | Gupta et al. ................... 504/225 |
| 7,553,867 B2 | | 6/2009 | Hamamura et al. |
| 2004/0185559 A1 | | 9/2004 | Monia et al. |
| 2004/0209871 A1 | | 10/2004 | Fox et al. |
| 2004/0224997 A1 | | 11/2004 | Smith et al. |
| 2005/0245531 A1 | | 11/2005 | Ji et al. |
| 2007/0244096 A1 | | 10/2007 | Fox et al. |
| 2008/0045539 A1 | | 2/2008 | Ji et al. |
| 2009/0064747 A1 | | 3/2009 | Evans |

FOREIGN PATENT DOCUMENTS

| | | |
|---|---|---|
| EP | 1 219 716 A2 | 7/2002 |
| EP | 1 219 716 A3 | 1/2004 |
| FR | 2 273 545 A1 | 1/1976 |
| JP | 03081275 A * | 4/1991 |
| JP | 2004-67635 A | 3/2004 |
| WO | 2004/022551 A1 | 3/2004 |
| WO | 2004/047755 A2 | 6/2004 |
| WO | 2004/047755 A3 | 6/2004 |
| WO | 2004/058176 A2 | 7/2004 |
| WO | 2004/058176 A3 | 7/2004 |
| WO | 2004/100881 A2 | 11/2004 |
| WO | 2004/100881 A3 | 11/2004 |
| WO | 2005/044250 A1 | 5/2005 |
| WO | 2005/047279 A1 | 5/2005 |
| WO | 2005/113527 A1 | 12/2005 |
| WO | 2007/003604 A2 | 1/2007 |
| WO | 2007/003604 A3 | 1/2007 |
| WO | 2007/126957 A2 | 11/2007 |
| WO | 2007/126957 A3 | 11/2007 |
| WO | 2008/012326 A1 | 1/2008 |
| WO | 2008/067257 A2 | 6/2008 |
| WO | 2008/067257 A3 | 6/2008 |
| WO | 2009/011285 A1 | 1/2009 |
| WO | 2009/040410 A1 | 4/2009 |

OTHER PUBLICATIONS

Brazil, M., "Slimming down without DGAT", Nature Reviews Drug Discovery, 2002, p. 408, vol. 1.
Casaschi, A. et al., "The Chalcone Xanthohumol Inhibits Triglyceride and Apolipoprotein B Secretion in HepG2 Cells", The Journal of Nutrition, 2004, p. 1340-1346.
Cases, S. et al., "Cloning of DGAT2, a Second Mammalian Diacylglycerol Acyltransferase, and Related Family Members", The Journal of Biological Chemistry, 2001, p. 38870-38876, vol. 276, No. 42.

(Continued)

*Primary Examiner* — Kahsay Habte
(74) *Attorney, Agent, or Firm* — Kenrick L. Vidale; Anna L. Cocuzzo; Janet E. Fair

(57) ABSTRACT

The present invention relates to novel heterocyclic compounds as diacylglycerol acyltransferase ("DGAT") inhibitors, pharmaceutical compositions comprising the heterocyclic compounds and the use of the compounds for treating or preventing a cardiovascular disease, a metabolic disorder, obesity or an obesity-related disorder, diabetes, dyslipidemia, a diabetic complication, impaired glucose tolerance or impaired fasting glucose. An illustrative compound of the invention is shown below: formula (I).

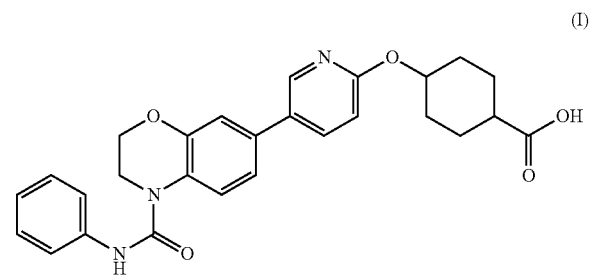

(I)

4 Claims, No Drawings

(56) References Cited

OTHER PUBLICATIONS

Cases, S., et al., "Identification of a gene encoding an acyl CoA:diacylglycerol acyltransferase, a key enzyme in triacylglycerol synthesis", Proc. Natl. Acad. Sci., 1998, p. 13018-13023, vol. 95.

Chung, M. Y. et al., "In vitro Inhibition of Diacylglycerol Acyltransferase by Prenylfavonoids from Sophora flavescens", Planta Med, 2004, p. 258-260, vol. 70.

Goto, K. et al., Synthesis and Biological Activity of the Metabolites of Diethyl 4-[(4-Bromo-2-cyanophenyl) carbamoyl]benzylphosphonate (NO-1886), Chem. Pharm. Bull., 1996, p. 547-551, vol. 44, No. 3.

Ikeda, M. et al., "Effects of OT-13540, a potential antiobesity compound, on plasma triglyceride levels in experimental hypertriglyceridemia rats", 16th International Symposium on Atherosclerosis, 2003, p. 127.

Kahn, C. R., "Triglycerides and toggling the tummy", Nature Genetics, 2000, p. 6-7, vol. 25.

Ko, J. S. et al., "Inhibitory Activity of Diacylglycerol Acyltransferase by Tanshinones from the Root of Salvia miltiorrhiza", Arch Pharm Res, 2002, p. 446-448, vol. 25, No. 4.

Ko, J. S. et al., "Quinolone Alkaloids, Diacylglycerol Acyltransferase Inhibitors from the Fruits of Evodia Rutaecarpa", Planta Med, 2002, p. 1131-1133, vol. 68.

Kurogi, Y. et al., "Synthesis and Hypolipidemic Activities fo Novel 2[4-[(Diethoxyphosphoryl)methyl]phenyl] quinazolines and 4(3H)-Quinazolinones", J. Med. Chem, 1996, p. 1433-1437, vol. 39.

Lardizabal, K. D. et al., "DGAT2 Is a New Diacylglycerol Acyltransferase Gene Family", The Journal of Biological Chemistry, 2001, p. 38862-38869, vol. 276, No. 42.

Lee, S. W. et al., "New Polyacetylenes, DGAT Inhibitors from the Roots of Panax ginseng", Planta Med, 2004, p. 197-200, vol. 70.

Lewis, G. F. et al., "Disordered Fat Storage and Mobilization in the Pathogenesis of Insulin Resistance and Type 2 Diabetes", Endocrine Reviews, 2002, p. 201-229, vol. 23, No. 2.

Malloy, M. J., "A Risk Factor for Atherosclerosis: Triglyceride-rich Lipoproteins", Advances in Internal Medicine, 2001, p. 111-136, vol. 47.

Mayorek, N. et al., "Inhibition of Diacylglycerol Acyltransferase by 2-Bromooctanoate in Cultured Rat Hepatocytes", The Journal of Biological Chemistry, 1985, p. 6528-6532, vol. 260, No. 11.

Mayorek, N. et al., "Triacylglycerol synthesis in cultured rat hepatocytes", Eur. J. Biochem, 1989, p. 395-400, vol. 182.

Subauste, A. et al., "DGAT: Novel Therapeutic Target for Obesity and Type 2 Diabetes Mellitus", Current Drug Targets—Immune, Endocrine & Metabolic Disorders, 2002, p. 263-270, vol. 3.

Sun, Q. et al., "Synthesis and Evaluation of Terbenzimidazoles as Topoisomerase I Inhibitors", J. Med. Chem, 1995, p. 3638-3644, vol. 38.

Tabata, N. et al., "Xanthohumols, Diacylglycerol Acyltransferase Inhibitors, From Humulus Lupulus", Phytochemistry, 1997, p. 683-687, vol. 46, No. 4.

Yanovski, S. Z. et al., "Obesity", N Engl J Med, 2002, p. 591-602, vol. 346, No. 8.

Yu, Y. H. et al., "The role of acyl-CoA:diacylglycerol acyltransferase (DGAT) in energy metabolism", Annals of Medicine, 2004, p. 252-261, vol. 36.

Zhu, D. et al., "Effect of gemfibrozil on apolipoprotein B secretion and diacylglycerol acyltransferase activity in human hepatoblastoma (HepG2) cells", Atherosclerosis, 2002, p. 221-228, vol. 164.

\* cited by examiner

BICYCLIC COMPOUNDS AS INHIBITORS OF DIACYLGLYCEROL ACYLTRANSFERASE

CROSS-REFERENCE TO RELATED APPLICATIONS

This application is a U.S. National Phase application under 35 U.S.C. §371 of PCT Application No. PCT/US2010/027443, filed Mar. 16, 2010, which published as WO 2010/107765 A1 on Sep. 23, 2010, and claims priority under 35 U.S.C. §365(b) from U.S. provisional patent application No. 61/161,212, filed Mar. 18, 2009.

FIELD OF THE INVENTION

The present invention relates to certain heterocyclic compounds useful as diacylglycerol acyltransferase ("DGAT") inhibitors, especially diacylglycerol acyltransferase 1 ("DGAT1") inhibitors, pharmaceutical compositions containing the compounds, and methods of treatment using the compounds and compositions to treat or prevent various diseases including cardiovascular disease, dyslipidemia, obesity and diabetes (e.g., Type 2 diabetes).

BACKGROUND OF THE INVENTION

There is a need for additional ways of treating diseases associated with metabolic syndrome such as, for example, dyslipidemia, cardiovascular disease, obesity and diabetes (e.g., Type 2 diabetes).

Triglycerides or triacylglycerols are the major form of energy storage in eukaryotic organisms. In mammals, these compounds are primarily synthesized in three tissues: the small intestine, liver, and adipocytes. Triglycerides or triacylglycerols support the major functions of dietary fat absorption, packaging of newly synthesized fatty acids and storage in fat tissue (see Subauste and Burant, Current Drug Targets-Immune, Endocrine & Metabolic Disorders (2003) 3, pp. 263-270).

Diacylglycerol O-acyltransferase, also known as diglyceride acyltransferase or DGAT, is a key enzyme in triglyceride synthesis. DGAT catalyzes the final and rate-limiting step in the triacylglycerol synthesis from 1,2-diacylglycerol (DAG) and long chain fatty acyl CoA as substrates. Thus, DGAT plays an essential role in the metabolism of cellular diacylglycerol and is critically important for triglyceride production and energy storage homeostasis (see Mayorek et al, European Journal of Biochemistry (1989) 182, pp. 395-400).

Two forms of DGAT have been cloned and are designated DGAT1 and DGAT2 [see Cases et al, Proceedings of the National Academy of Science, USA (1998) 95, pp. 13018-13023, Lardizabal et al, Journal of Biological Chemistry (2001) 276, pp. 38862-38869 and Cases et al, Journal of Biological Chemistry (2001) 276, pp. 38870-38876]. Although both enzymes utilize the same substrates, there is no homology between DGAT1 and DGAT2. Both enzymes are widely expressed. However, some differences do exist in the relative abundance of expression in various tissues.

Disorders or imbalances in triglyceride metabolism, both absorption as well as de novo synthesis, have been implicated in the pathogenesis of a variety of disease risks. These include obesity, insulin resistance syndrome, Type II diabetes, dyslipidemia, metabolic syndrome (syndrome X) and coronary heart disease [see Kahn, Nature Genetics (2000) 25, pp. 6-7, Yanovski and Yanovski, New England Journal of Medicine (2002) 346, pp. 591-602, Lewis et al, Endocrine Reviews (2002) 23, pp. 201, Brazil, Nature Reviews Drug Discovery (2002) 1, pp. 408, Malloy and Kane, Advances in Internal Medicine (2001) 47, pp. 111, Subauste and Burant, Current Drug Targets-Immune, Endocrine & Metabolic Disorders (2003) 3, pp. 263-270 and Yu and Ginsberg, Annals of Medicine (2004) 36, pp. 252-261]. Compounds that can decrease the synthesis of triglycerides from diacylglycerol by inhibiting or lowering the activity of the DGAT enzyme would be of value as therapeutic agents for the treatment of diseases associated with abnormal metabolism of triglycerides.

Known inhibitors of DGAT include: dibenzoazepinones (see Ramharack et al, EP1219716 and Burrows et al, 26th National Medicinal Chemistry Symposium (1998) poster C-22), substituted amino-pyrimidino-oxazines (see Fox et al, WO2004047755), chalcones such as xanthohumol (see Tabata et al, Phytochemistry (1997) 46, pp. 683-687 and Casaschi et al, Journal of Nutrition (2004) 134, pp. 1340-1346), substituted benzyl-phosphonates (see Kurogi et al, Journal of Medicinal Chemistry (1996) 39, pp. 1433-1437, Goto et al, Chemistry and Pharmaceutical Bulletin (1996) 44, pp. 547-551, Ikeda et al, Thirteenth International Symposium on Atherosclerosis (2003), abstract 2P-0401, and Miyata et al, JP 2004067635), aryl alkyl acid derivatives (see Smith et al, WO2004100881 and US20040224997), furan and thiophene derivatives (see WO2004022551), pyrrolo[1,2b]pyridazine derivatives (see Fox et al, WO2005103907), and substituted sulfonamides (see Budd Haeberlein and Buckett, WO20050442500).

Also known to be inhibitors of DGAT are: 2-bromo-palmitic acid (see Colman et al, Biochimica et Biophysica Acta (1992) pp. 1125, 203-9), 2-bromo-octanoic acid (see Mayorek and Bar-Tana, Journal of Biological Chemistry (1985) 260, pp. 6528-6532), roselipins (see Noriko et al, (Journal of Antibiotics (1999) 52, pp. 815-826), amidepsin (see Tomoda et al, Journal of Antibiotics (1995) 48, pp. 42-7), isochromophilone, prenylflavonoids (see Chung et al, Planta Medica (2004) 70, v58-260), polyacetylenes (see Lee et al, Planta Medica (2004) 70, pp. 97-200), cochlioquinones (see Lee et al, Journal of Antibiotics (2003) 56, pp. 967-969), tanshinones (see Ko et al, Archives of Pharmaceutical Research (2002) 25, pp. 446-448), gemfibrozil (see Zhu et al, Atherosclerosis (2002) 164, pp. 221-228), and substituted quinolones (see Ko et al, Planta Medica (2002) 68, pp. 1131-1133). Also known to be modulators of DGAT activity are antisense oligonucleotides (see Monia and Graham, US20040185559).

DGAT inhibitors have been described. See, for example, PCT publication US 2007/0244096 (published Oct. 31, 2007; applicant: Japan Tobacco). Claim 1 therein discloses compounds of the formula:

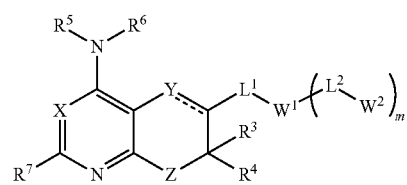

wherein $R^3$, $R^4$, $R^5$, $R^6$, $R^7$, X, Y, Z, $L^1$, $L^2$, $W^1$, $W^2$ and m are described. WO 2007/126957 (published Nov. 8, 2007; applicant: Novartis Pharma). Claim 1 therein discloses compounds of the formula:

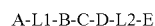

A-L1-B-C-D-L2-E wherein A, L1, B, C, D, L2 and E are described. WO 2008/067257 (published Jun. 5, 2008; applicant: Abbott Laboratories). Claim 1 therein discloses compounds of the formula:

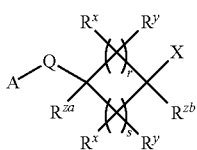

wherein A, Q, X, $R^x$, $R^y$, $R^{za}$, $R^{zb}$, r and s are described. WO 2009/011285 (published Jan. 22, 2009; applicant: Taisho Pharmaceutical Co.). Claim 1 therein discloses compounds of the formula:

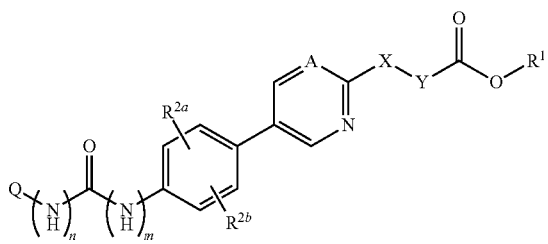

Wherein are A, X, Y, Q, $R^1$, $R^{2a}$, and $R^{2b}$ are described.

Commonly owned U.S. provisional patent application Ser. Nos. 61/115,991, 61/115,995, 61/116,000, 61/115,982, 61/115,985 and 61/115,987, all filed Nov. 19, 2008, also describe DGAT inhibitors.

A need exists in the art, however, for additional DGAT inhibitors that have efficacy for the treatment of metabolic disorders such as, for example, obesity, Type II diabetes mellitus and metabolic syndrome.

SUMMARY OF THE INVENTION

In an embodiment, this invention discloses a compound, or pharmaceutically acceptable salts, solvates, esters or prodrugs of said compound, or pharmaceutically acceptable salts, solvates or esters of said prodrug, the compound being represented by the Formula IA:

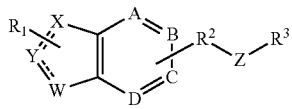

or a stereoisomer or tautomer of said compound, wherein
the bond denoted by ═ represents a single bond or a double bond;
W is selected from the group consisting of $C(R^4)$, $C(R^4R^4)$, N, $N(R^4)$, S or O;
X is selected from the group consisting of $C(R^4)$, $C(R^4R^4)$, N, $N(R^4)$, S or O;
Y is selected from the group consisting of $C(R^4)$, $C(R^4R^4)$, N, $N(R^4)$, S or O;
$R^4$ is present depending on the allowed vacancy and is selected from H, alkyl, $R^1$, —OH, (═O), or hydroxyalkyl;
W, X or Y is substituted with $R^1$ depending on the allowed valency;
$R^1$ is selected from the group consisting of alkyl-, aryl-, arylalkyl-, heteroaryl-, heteroarylalkyl-, cycloalkyl-, (cycloalkyl)alkyl-, heterocycloalkyl-, (heterocycloalkyl)alkyl-, (alkyl)amino-, (aryl)amino-, (arylalkyl)amino-, (heteroaryl)amino-, (heteroarylalkyl)amino-, (cycloalkyl)amino-, ((cycloalkyl)alkyl)amino-, (heterocycloalkyl)amino-, ((heterocycloalkyl)alkyl)amino-, (alkyl)carbonyl-, (cycloalkyl)carbonyl-, (cycloalkyl)alkylcarbonyl-, (heterocycloalkyl)carbonyl-, (heterocyclyl)alkylcarbonyl-, (aryl)carbonyl-, (aryl)alkylcarbonyl-, (heteroaryl)carbonyl-, (heteroaryl)alkylcarbonyl-, (alkyl)thiocarbonyl-, (cycloalkyl)thiocarbonyl-, (cycloalkyl)alkylthiocarbonyl-, (heterocycloalkyl)thiocarbonyl-, (heterocyclyl)alkylthiocarbonyl-, (aryl)thiocarbonyl-, (aryl)alkylthiocarbonyl-, (heteroaryl)thiocarbonyl-, (heteroaryl)alkylthiocarbonyl-, (alkyloxy)carbonyl-, (cycloalkyloxy)carbonyl-, (heterocycloalkyloxy)carbonyl-, (aryloxy)carbonyl-, (arylalkyloxy)carbonyl-, (heteroaryloxy)carbonyl-, (heteroarylalkyloxy)carbonyl-, (alkylamino)carbonyl-, (cycloalkylamino)carbonyl-, (heterocycloalkylamino)carbonyl-, (arylamino)carbonyl-, (arylalkylamino)carbonyl-, (heteroarylamino)carbonyl[, (heteroarylalkylamino)carbonyl-, (alkyl)sulfonyl-, (cycloalkyl)sulfonyl-, (heterocycloalkyl)sulfonyl-, (aryl)sulfonyl-, (arylalkyl)sulfonyl-, (heteroaryl)sulfonyl-, (heteroarylalkyl)sulfonyl-, (alkylamino)sulfonyl-, (cycloalkylamino)sulfonyl-, (heterocycloalkylamino)sulfonyl-, (arylamino)sulfonyl-, (arylalkylamino)sulfonyl-, (heteroarylamino)sulfonyl- and (heteroarylalkylamino)sulfonyl-, wherein each of these $R^1$ groups is unsubstituted or optionally independently substituted with 1-4 substituents independently selected from halogen, amino, alkylamino, hydroxy, alkoxy, alkyl, cycloalkyl, carboxy, carboxyester, methylenedioxy, CN, cyanoalkyl-, nitro and $CF_3$;
A is selected from the group consisting of $C(R^5)$ or N;
B is selected from the group consisting of $C(R^5)$ or N;
C is selected from the group consisting of $C(R^5)$ or N;
D is selected from the group consisting of $C(R^5)$ or N;
$R^5$ is selected from H, alkyl, cycloalkyl, amino, alkylamino, hydroxy, alkoxy, halogen, cycloalkyl, heterocycloalkyl, heteroaryl or aryl, wherein each of these $R^5$ groups is unsubstituted or optionally independently substituted with 1-4 substituents independently selected from halogen, amino, alkylamino, hydroxy, alkoxy, alkyl, cycloalkyl, CN and $CF_3$;
each of A, B, C or D is optionally substituted, depending on the allowed vacancy, with cycloalkyl, heterocycloalkyl, heteroaryl or aryl, wherein each of these groups is unsubstituted or optionally independently substituted with 1-4 substituents independently selected from halogen, amino, alkylamino, hydroxy, alkoxy, alkyl, cycloalkyl, CN and $CF_3$;
$R^2$ is heteroaryl, wherein said heteroaryl is unsubstituted or optionally independently substituted with 1-4 substituents independently selected from halogen, amino, alkylamino, hydroxy, alkoxy, alkyl, cycloalkyl, CN and $CF_3$;
Z is selected from the group consisting of a bond, O, $N(R^6)$, alkyl, carbonyl and sulfonyl;
$R^6$ is selected from H or alkyl;
$R^3$ is selected from the group consisting of cycloalkyl, heterocyclyl, aryl and heteroaryl, wherein each of these $R^3$ groups is unsubstituted or optionally independently substituted with 1-4 substituents independently selected from halogen, amino, alkylamino, hydroxy, alkoxy, alkyl, cycloalkyl, —CN, —$CF_3$, —C(O)NH($R^6$), —CON($R^6$)$_2$, —COOH, —C(O)—Oalkyl, -alkylCOOH, -alkyl-C(O)O-alkyl, -alkyl-C(O)$NH_2$, -alkyl-C(O)—NH—$(CH_2)_{1-3}$—CN, -alkyl-C(O)—NH—$(CH_2)_{1-3}$-(heteroaryl), —COOH bioisostere or -alkylCOOH bioisostere.

The term "COOH bioisostere" is as defined in *The Practice of Medicinal Chemistry*, C. G. Wermuth Ed.; Academic Press: New York, 1996, p. 203. Non-limiting examples of COOH bioisosteres include —SO₃H, —S(O)₂NHR⁷, —S(O)₂NHC(O)R⁷, —CH₂S(O)₂R⁷, —C(O)NHS(O)₂R⁷, —C(O)NHOH, —C(O)NHCN, —CH(CF₃)OH, —C(CF₃)₂OH, —P(O)(OH)₂ and the groups listed below:

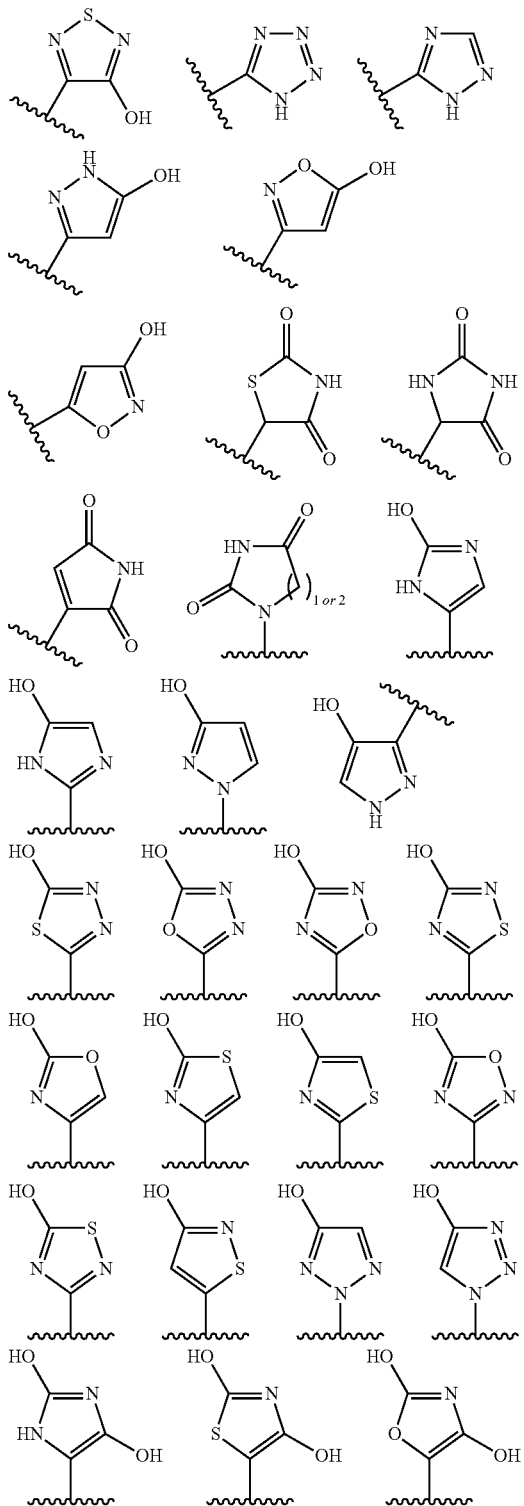
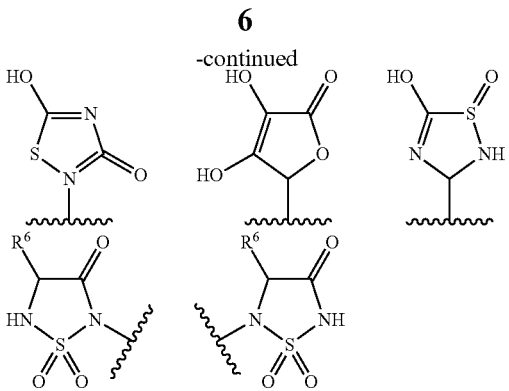

where R⁷ is selected from alkyl, aryl or heteroaryl.

In another aspect, this invention discloses a compound, or pharmaceutically acceptable salts, solvates, esters or prodrugs of said compound, or pharmaceutically acceptable salts, solvates or esters of said prodrug, the compound being represented by the Formula IB:

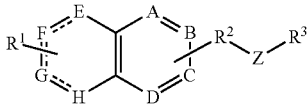

IB or a stereoisomer or tautomer of said compound, wherein the bond denoted by ═══ represents a single bond or a double bond;

E is selected from the group consisting of C(R⁴), C(R⁴R⁴), N, N→O, N(R⁴), S or O;

F is selected from the group consisting of C(R⁴), C(R⁴R⁴), N, N→O, or NR⁴;

G is selected from the group consisting of C(R⁴), C(R⁴R⁴), N, N→O, or NR⁴;

H is selected from the group consisting of C(R⁴), C(R⁴R⁴), N, N→O(R⁴), S or O;

R⁴ is present depending on the allowed vacancy and is selected from H, alkyl, R¹, —OH, (═O), or hydroxyalkyl;

E, F, G or H is substituted with R¹ depending on the allowed valency;

R¹ is selected from the group consisting of alkyl, aryl, arylalkyl, heteroaryl, heteroarylalkyl, cycloalkyl, (cycloalkyl)alkyl, heterocycloalkyl, (heterocycloalkyl)alkyl, (alkyl)amino-, (aryl)amino-, (arylalkyl)amino-, (heteroaryl)amino-, (heteroarylalkyl)amino-, (cycloalkyl)amino-, ((cycloalkyl)alkyl)amino-, (heterocycloalkyl)amino-, ((heterocycloalkyl)alkyl)amino-, (alkyl)carbonyl, (cycloalkyl)carbonyl, (cycloalkyl)alkylcarbonyl, (heterocycloalkyl)carbonyl, (heterocyclyl)alkylcarbonyl, (aryl)carbonyl, (aryl)alkylcarbonyl, (heteroaryl)carbonyl, (heteroaryl)alkylcarbonyl, (alkyl)thiocarbonyl, (cycloalkyl)thiocarbonyl, (cycloalkyl)alkylthiocarbonyl; (heterocycloalkyl)thiocarbonyl, (heterocyclyl)alkylthiocarbonyl, (aryl)thiocarbonyl, (aryl)alkylthiocarbonyl; (heteroaryl)thiocarbonyl, (heteroaryl)alkylthiocarbonyl; (alkyloxy)carbonyl, (cycloalkyloxy)carbonyl, (heterocycloalkyloxy)carbonyl, (aryloxy)carbonyl, (arylalkyloxy)carbonyl; (heteroaryloxy)carbonyl, (heteroarylalkyloxy)carbonyl; (alkylamino)carbonyl, (cycloalkylamino)carbonyl, (heterocycloalkylamino)carbonyl, (arylamino)carbonyl, (arylalkylamino)carbonyl; (heteroarylamino)carbonyl, (heteroarylalkylamino)carbonyl; (alkyl)sulfonyl, (cycloalkyl)sulfonyl, (heterocycloalkyl)sulfonyl, (aryl)sulfonyl, (arylalkyl)sulfonyl; (heteroaryl)sulfonyl, (heteroarylalkyl)sulfonyl; (alkylamino)sulfonyl, (cycloalkylamino)sulfonyl, (heterocycloalkylamino)sulfonyl, (arylamino)sulfonyl, (arylalkylamino)sulfonyl; (heteroarylamino)sulfonyl and (heteroarylalkylamino) sulfonyl wherein each of these $R^1$ groups is unsubstituted or optionally independently substituted with 1-4 substituents independently selected from halogen, amino, alkylamino, hydroxy, alkoxy, alkyl, cycloalkyl, carboxy, carboxyester, methylenedioxy, CN, cyanoalkyl-, nitro and $CF_3$;

A is selected from the group consisting of $CR^5$ or N;
B is selected from the group consisting of $CR^5$ or N;
C is selected from the group consisting of $CR^5$ or N;
D is selected from the group consisting of $CR^5$ or N;
$R^5$ is selected from H, alkyl, cycloalkyl, amino, alkylamino, hydroxy, alkoxy, halogen, cycloalkyl, heterocycloalkyl, heteroaryl or aryl, wherein each of these $R^5$ groups is unsubstituted or optionally independently substituted with 1-4 substituents independently selected from halogen, amino, alkylamino, hydroxy, alkoxy, alkyl, cycloalkyl, CN and $CF_3$;
each of A, B, C or D is optionally substituted, depending on the allowed vacancy, with cycloalkyl, heterocycloalkyl, heteroaryl or aryl, wherein each of these groups is unsubstituted or optionally independently substituted with 1-4 substituents independently selected from halogen, amino, alkylamino, hydroxy, alkoxy, alkyl, cycloalkyl, CN and $CF_3$;
$R^2$ is heteroaryl, wherein said heteroaryl is unsubstituted or optionally independently substituted with 1-4 substituents independently selected from halogen, amino, alkylamino, hydroxy, alkoxy, alkyl, cycloalkyl, CN and $CF_3$;
Z is selected from the group consisting of a bond, O, S, $NR^6$, alkyl, carbonyl and sulfonyl;
$R^6$ is selected from H or alkyl; and
$R^3$ is selected from the group consisting of alkyl, cycloalkyl, heterocyclyl, aryl, heteroaryl, -alkyl(cycloalkyl), -alkyl(heterocyclyl), -alkyl(aryl) and -alkyl(heteroaryl), wherein each of these $R^3$ groups is unsubstituted or optionally independently substituted with 1-4 substituents independently selected from halogen, amino, alkylamino, hydroxy, alkoxy, alkyl, cycloalkyl, spirocyclyl, —CN, —$CF_3$, —C(O)NH($R^6$), —CON($R^6$)$_2$, —COOH, —C(O)Oalkyl, -alkylCOOH, -alkyl-C(O)O-alkyl, -alkyl-C(O)NH$_2$, -alkyl-C(O)—NH—(CH$_2$)$_{1-3}$—CN, —C(O)—NH—(CH$_2$)$_{1-3}$-(heteroaryl), -alkyl-C(O)—NH—(CH$_2$)$_{1-3}$-(heteroaryl), —COOH bioisostere or -alkyl-COOH bioisostere.

The term "COOH bioisostere" is as defined under Formula IA.

In another aspect, this invention provides compositions comprising at least one compound of Formula IA or Formula IB.

In another aspect, this invention provides pharmaceutical compositions comprising at least one compound of Formula IA or Formula IB and at least one pharmaceutically acceptable carrier.

In another aspect, this invention provides a method of treating diabetes in a patient in need of such treatment using therapeutically effective amounts of at least one compound of Formula IA or Formula IB, or of a composition comprising at least one compound of Formula IA or Formula IB.

In another aspect, this invention provides a method of treating diabetes in a patient in need of such treatment, e.g., Type 2 diabetes, using therapeutically effective amounts of at least one compound of Formula IA or Formula IB, or of a composition comprising at least one compound of Formula IA or Formula IB.

In another aspect, this invention provides a method of treating metabolic syndrome in a patient in need of such treatment, using therapeutically effective amounts of at least one compound of Formula IA or Formula IB, or of a composition comprising at least one compound of Formula IA or Formula IB.

In another aspect, this invention provides a method of inhibiting DGAT using therapeutically effective amounts of at least one compound of Formula IA or Formula IB, or of a composition comprising at least one compound of Formula IA or Formula IB.

In another aspect, this invention provides a method of inhibiting DGAT1 using therapeutically effective amounts of at least one compound of Formula IA or Formula IB, or of a composition comprising at least one compound of Formula IA or Formula IB.

DESCRIPTION OF THE INVENTION

In an embodiment, the present invention discloses compounds of Formula IA or Formula IB, or pharmaceutically acceptable salts, solvates, esters or prodrugs thereof.

The following embodiments (stated as "another embodiment") are independent of one another; different such embodiments can be independently selected and combined in various combinations. Such combinations should be considered as part of the invention. The thus described embodiments are applicable independently to Formula IA and Formula IB as appropriate.

In another embodiment, W is $C(R^4)$.
In another embodiment, W is $C(R^4R^4)$.
In another embodiment, W is N.
In another embodiment, W is $N(R^4)$.
In another embodiment, W is S.
In another embodiment, W is O.
In another embodiment, X is $C(R^4)$.
In another embodiment, X is $C(R^4R^4)$.
In another embodiment, X is N.
In another embodiment, X is $N(R^4)$.
In another embodiment, X is S.
In another embodiment, X is O.
In another embodiment, Y is $C(R^4)$.
In another embodiment, Y is $C(R^4R^4)$.
In another embodiment, Y is N.
In another embodiment, Y is $N(R^4)$.
In another embodiment, Y is S.
In another embodiment, Y is O.
In another embodiment, W=X=N.
In another embodiment, W=Y=N.
In another embodiment, X=Y=N.
In another embodiment, ═ represents a single bond.
In another embodiment, ═ represents a double bond.
In another embodiment in Formula IB, both ═ represent double bonds.
In another embodiment in Formula IB, both ═ represent single bonds.
In another embodiment in Formula IB, one ═ represents a double bond and the other ═ represents a single bond.
In another embodiment, $R^1$ is alkyl.
In another embodiment, $R^1$ is aryl.
In another embodiment, $R^1$ is arylalkyl.
In another embodiment, $R^1$ is cycloalkyl.
In another embodiment, $R^1$ is cycloalkylalkyl.
In another embodiment, $R^1$ is heterocyclyl.

In another embodiment, $R^1$ is heterocyclylalkyl.
In another embodiment, $R^1$ is heteroaryl.
In another embodiment, $R^1$ is heteroarylalkyl.
In another embodiment, $R^1$ is alkylcarbonyl.
In another embodiment, $R^1$ is arylcarbonyl.
In another embodiment, $R^1$ is cycloalkylcarbonyl.
In another embodiment, $R^1$ is (cycloalkyl)alkylcarbonyl.
In another embodiment, $R^1$ is heteroarylcarbonyl.
In another embodiment, $R^1$ is heterocyclylcarbonyl.
In another embodiment, $R^1$ is (heterocyclyl)alkylcarbonyl.
In another embodiment, $R^1$ is (aryl)alkylcarbonyl.
In another embodiment, $R^1$ is (heteroaryl)alkylcarbonyl.
In another embodiment, $R^1$ is (alkylthio)carbonyl-.
In another embodiment, $R^1$ is (alkoxy)carbonyl-.
In another embodiment, $R^1$ is (alkylamino)carbonyl.
In another embodiment, $R^1$ is (arylamino)carbonyl-.
In another embodiment, $R^1$ is (heteroarylamino)carbonyl-.
In another embodiment, $R^1$ is (heterocyclylamino)carbonyl.
In another embodiment, $R^1$ is (cycloalkylamino)carbonyl.
In another embodiment, $R^1$ is (heterocyclylamino)sulfonyl.
In another embodiment, $R^1$ is (arylamino)sulfonyl-.
In another embodiment, $R^1$ is (heteroarylamino)sulfonyl.
In another embodiment, $R^1$ comes off a ring carbon on the ring shown in Formula IA or IB.
In another embodiment, $R^1$ comes off a ring nitrogen on the ring shown in Formula IA or IB.
In another embodiment, E is $C(R^4)$.
In another embodiment, E is $C(R^4R^4)$.
In another embodiment, E is N.
In another embodiment, E is $N(R^4)$.
In another embodiment, E is S.
In another embodiment, E is O.
In another embodiment, H is $C(R^4)$.
In another embodiment, H is $C(R^4R^4)$.
In another embodiment, H is N.
In another embodiment, H is $N(R^4)$.
In another embodiment, H is S.
In another embodiment, H is O.
In another embodiment, F is $C(R^4)$.
In another embodiment, F is $C(R^4R^4)$.
In another embodiment, F is N.
In another embodiment, F is $N(R^4)$.
In another embodiment, G is $C(R^4)$.
In another embodiment, G is $C(R^4R^4)$.
In another embodiment, G is N.
In another embodiment, G is $N(R^4)$.
In another embodiment, E=F=N.
In another embodiment, E=G=N.
In another embodiment, F=H=N.
In another embodiment, E=F=G=H.
In another embodiment, A is $C(R^5)$.
In another embodiment, A is N.
In another embodiment, B is $C(R^5)$.
In another embodiment, B is N.
In another embodiment, C is $C(R^5)$.
In another embodiment, C is N.
In another embodiment, D is $C(R^5)$.
In another embodiment, D is N.
In another embodiment, $R^5$ is H.
In another embodiment, $R^5$ is alkyl.
In another embodiment, $R^5$ is methyl.
In another embodiment, $R^5$ is cycloalkyl.
In another embodiment, $R^5$ is amino.
In another embodiment, $R^5$ is alkylamino.
In another embodiment, $R^5$ is —OH.
In another embodiment, $R^5$ is alkoxy.
In another embodiment, $R^5$ is halo.
In another embodiment, $R^5$ is chloro.
In another embodiment, $R^5$ is cycloalkyl, heterocycloalkyl, heteroaryl or aryl, wherein each of these $R^5$ groups is unsubstituted or optionally independently substituted with 1-4 substituents independently selected from halogen, amino, alkylamino, hydroxy, alkoxy, alkyl, cycloalkyl, CN and $CF_3$;
In another embodiment, $R^6$ is H.
In another embodiment, $R^6$ is alkyl.
In another embodiment, Z is a bond.
In another embodiment, Z is O.
In another embodiment, Z is $N(R^4)$.
In another embodiment, Z is alkyl.
In another embodiment, Z is carbonyl.
In another embodiment, Z is sulfonyl.
In another embodiment, $R^3$ is cycloalkyl.
In another embodiment, $R^3$ is aryl.
In another embodiment, $R^3$ is heteroaryl.
In another embodiment, $R^3$ is heterocyclyl.
In another embodiment, $R^3$ is unsubstituted.
In another embodiment, $R^3$ is substituted with one moiety as described earlier.
In another embodiment, $R^3$ is substituted with more than one moiety as described earlier.
In another embodiment, $R^3$ is substituted with an alkyl.
In another embodiment, $R^3$ is substituted with a lower alkyl.
In another embodiment, $R^3$ is substituted with a —C(O)NH($R^6$).
In another embodiment, $R^3$ is substituted with a —C(O)N($R^6$)$_2$.
In another embodiment, $R^3$ is substituted with a carboxyl or carboxyester.
In another embodiment, $R^3$ is substituted with COOH bioisostere,
wherein COOH bioisostere is as defined earlier.
In another embodiment, $R^3$ is substituted with halo.
In another embodiment, $R^3$ is substituted with cyano.
In another embodiment, $R^3$ is substituted with —$OR^5$.
In another embodiment, $R^3$ is substituted with —$N(R^4R^5)$.
In another embodiment, $R^3$ is substituted with —C(O)—$N(R^4R^5)$.
In another embodiment, $R^3$ is substituted with both halo and carboxyl.
In another embodiment, $R^3$ is substituted with both —$OR^5$ and carboxyl.
In another embodiment, $R^3$ is substituted with both carboxy and alkyl-.
In another embodiment, $R^3$ is substituted with -alkyl)-C(O)$N(R^4R^5)$.
In another embodiment, in Formula IA, the moiety:

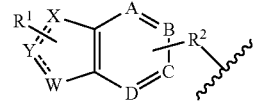

represents the moiety:

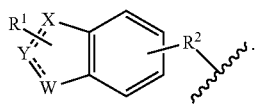

In another embodiment, in Formula IA, the moiety:

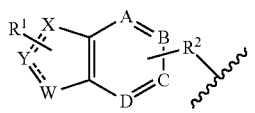

represents the moiety:

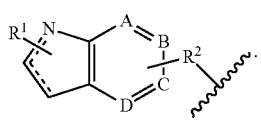

In another embodiment, in Formula IA, the moiety:

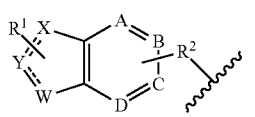

represents the moiety:

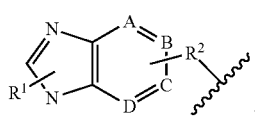

In another embodiment, in Formula IA, the moiety:

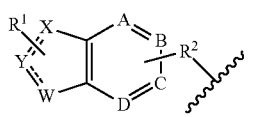

represents the moiety:

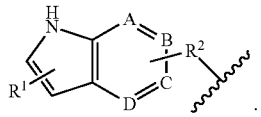

In another embodiment, in Formula IA, the moiety:

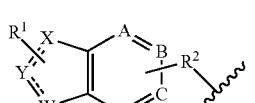

represents the moiety:

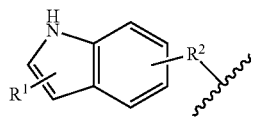

In another embodiment, in Formula IB, the moiety:

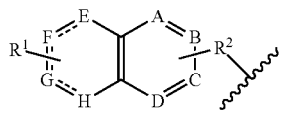

represents the moiety:

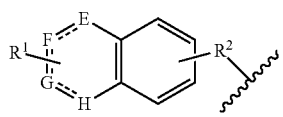

In another embodiment, in Formula IB, the moiety:

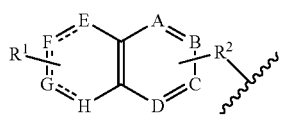

represents the moiety:

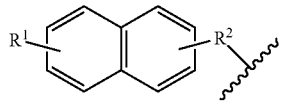

In another embodiment, in Formula IB, the moiety:

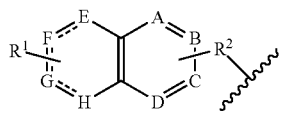

represents the moiety:

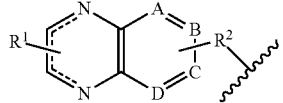

In another embodiment, in Formula IB, the moiety:

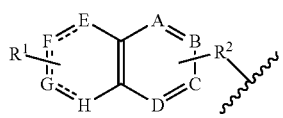

represents the moiety:

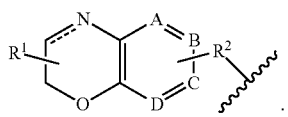

In another embodiment, in Formula IB, the moiety:

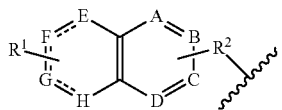

represents the moiety:

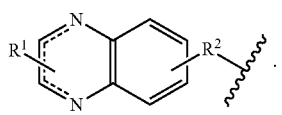

In another embodiment, in Formula IB, the moiety:

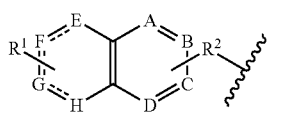

represents the moiety:

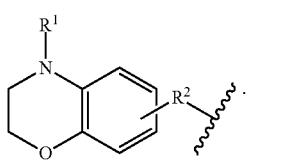

In another embodiment of Formula IA or Formula IB, wherein X, Y, W, Z, $R^1$, $R^2$, and $R^3$ and any remaining moieties are independently selected, W is C, X is C, Y is C, Z is aryl, and the others are as previously defined.

In another embodiment of Formula IA or Formula IB, wherein X, Y, W, Z, $R^1$, $R^2$, and $R^3$ and any remaining moieties are independently selected, W is N, X is C, Y is C, Z is aryl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is aryl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is aryl, $R^1$ is (arylamino)carbonyl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is aryl, $R^1$ is (arylamino)carbonyl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is aryl, $R^1$ is arylcarbonyl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is aryl, $R^1$ is arylcarbonyl, $R^3$ is cycloalkyl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is phenyl, $R^1$ is (arylamino)carbonyl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is phenyl, $R^1$ is (arylamino)carbonyl, $R^3$ is cycloalkyl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is biphenyl, $R^1$ is (arylamino)carbonyl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is biphenyl, $R^1$ is (arylamino)carbonyl, $R^3$ is cycloalkyl, and the others are as previously defined.

In another embodiment of Formula IA or Formula IB, wherein X, Y, W, Z, $R^1$, $R^2$, and $R^3$ and any remaining moieties are independently selected, W is N, X is N, Y is C, Z is biphenyl, $R^1$ is (arylamino)carbonyl, $R^3$ is cycloalkyl, and the others are as previously defined.

Non-limiting examples of the compounds of Formula IA or Formula IB are shown below as well as in the Examples section:

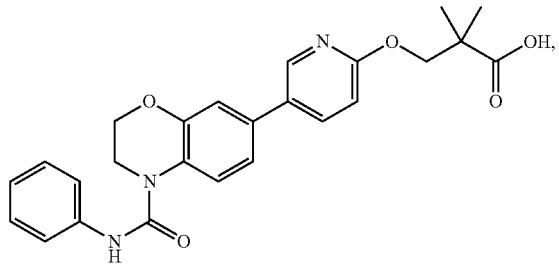

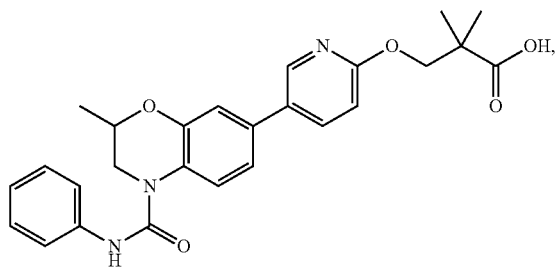

-continued
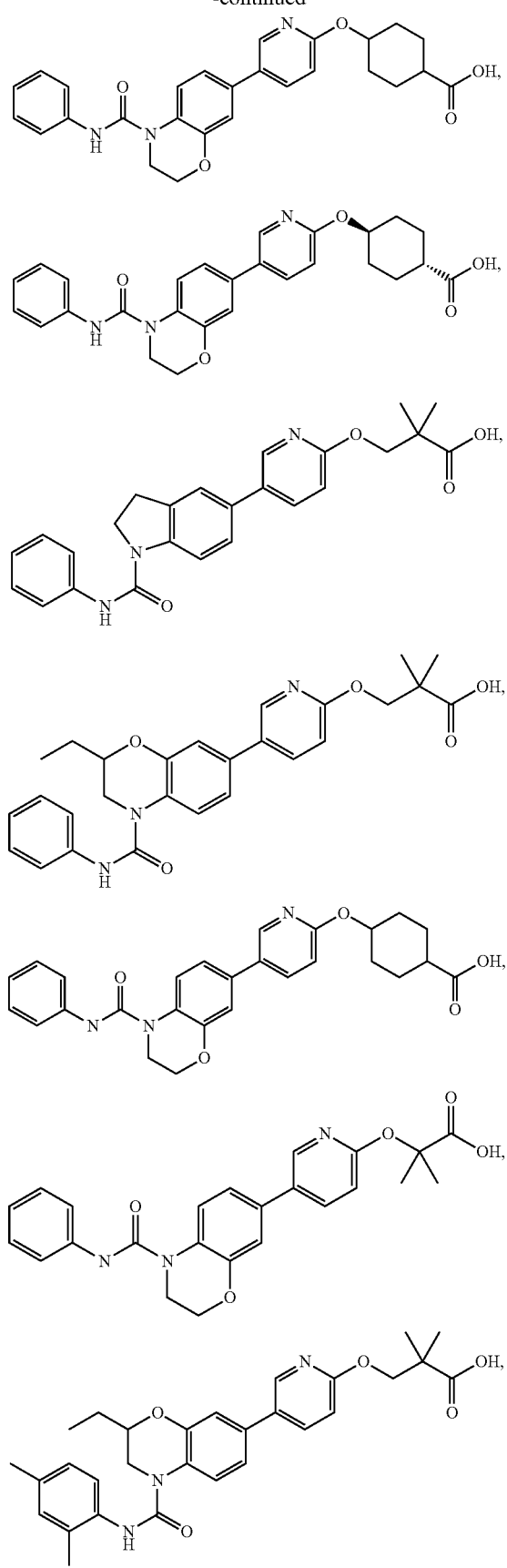
-continued
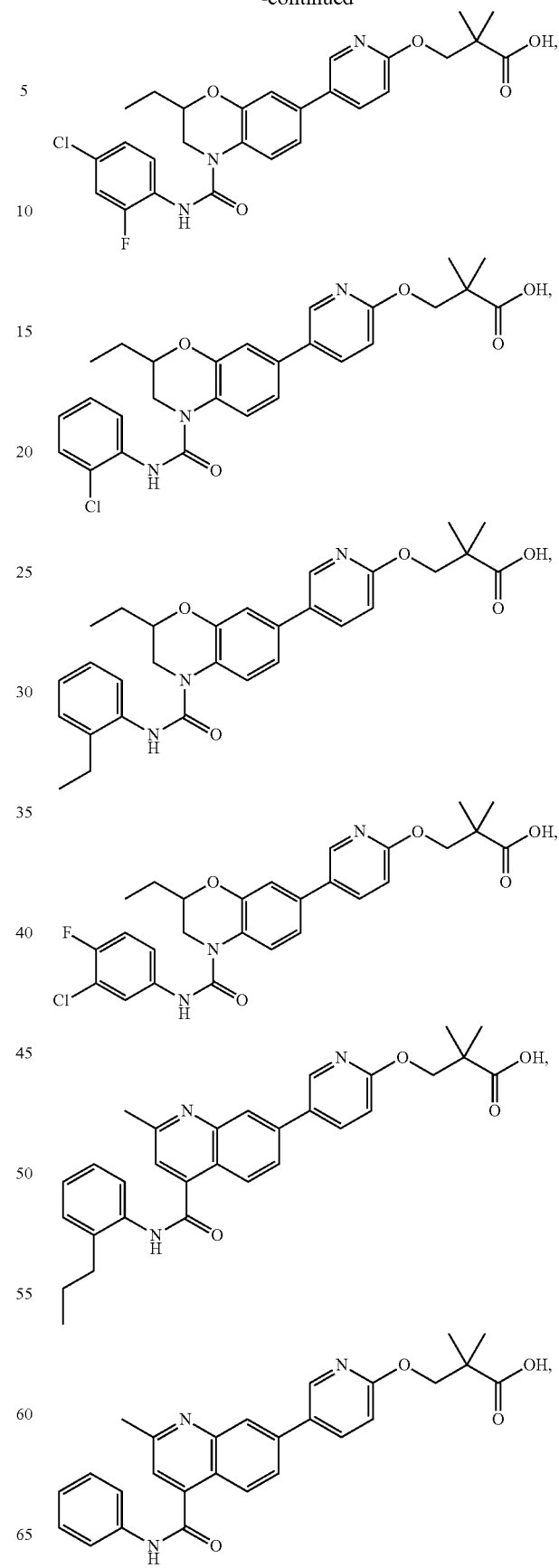

17
-continued
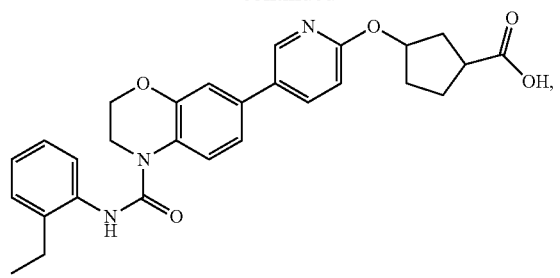
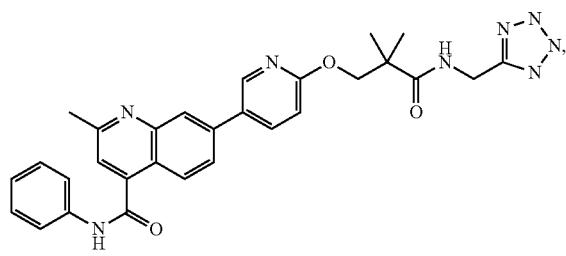
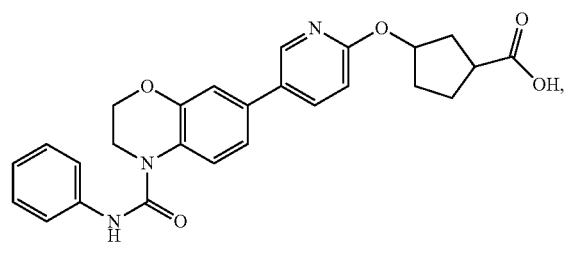
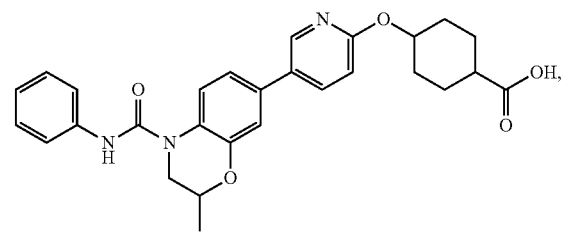
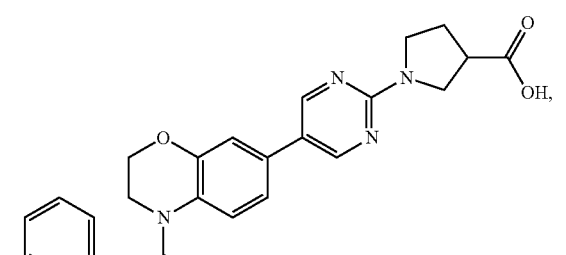
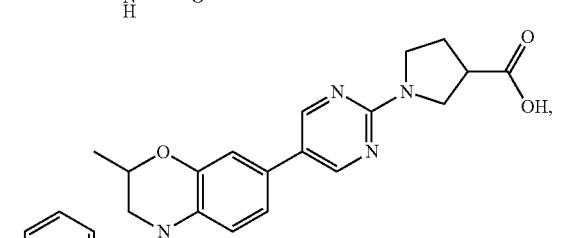
18
-continued
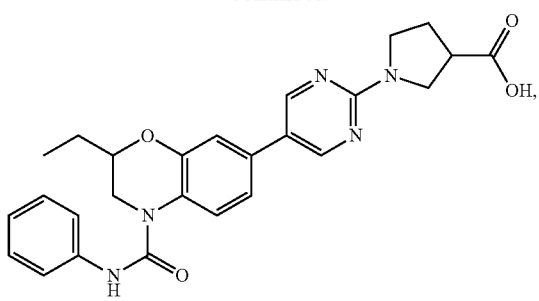
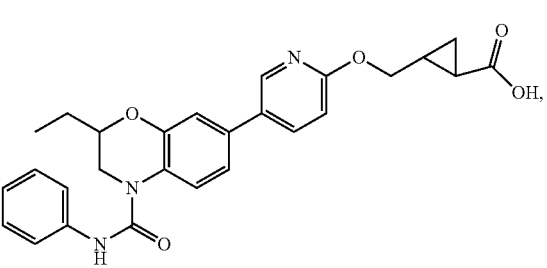
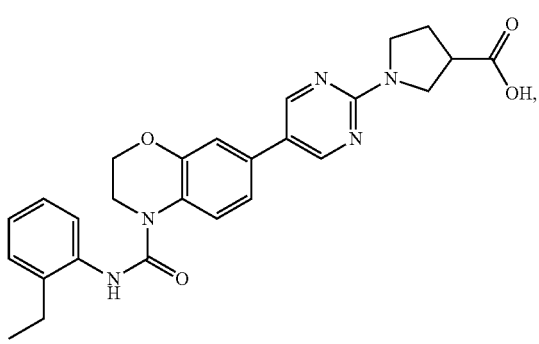
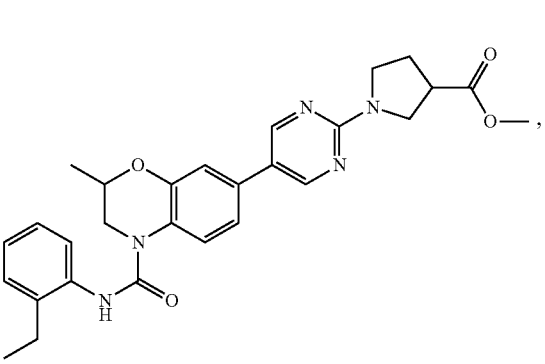
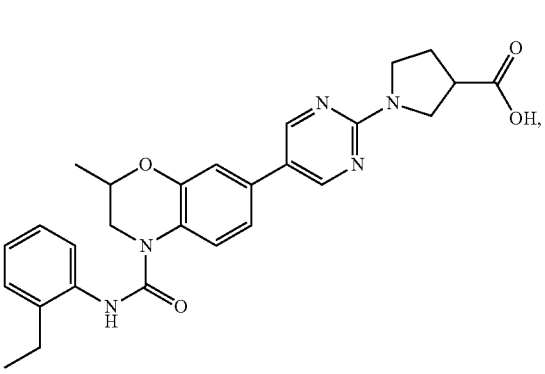

19
-continued
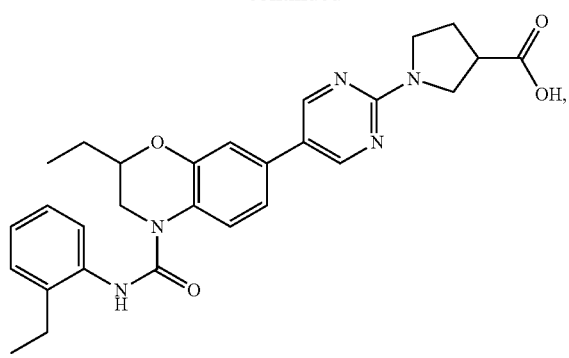
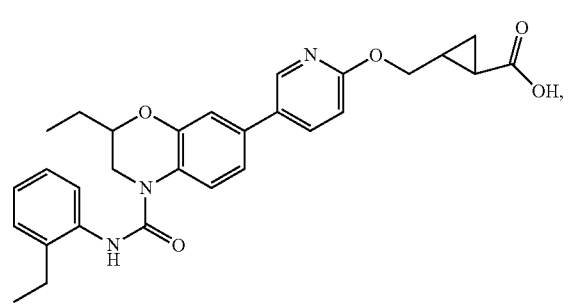
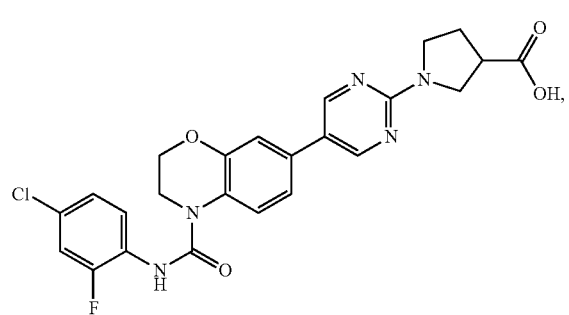
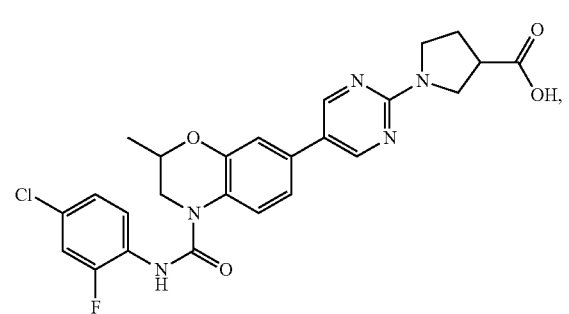 [SMILES: CC1CN(C(=O)Nc2ccc(Cl)cc2F)c2ccc(-c3cnc(N4CCC(C(=O)O)C4)nc3)cc2O1]
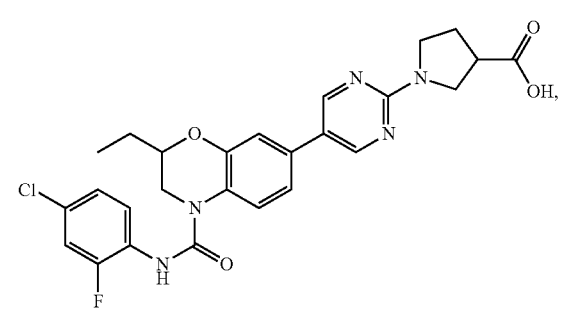
20
-continued
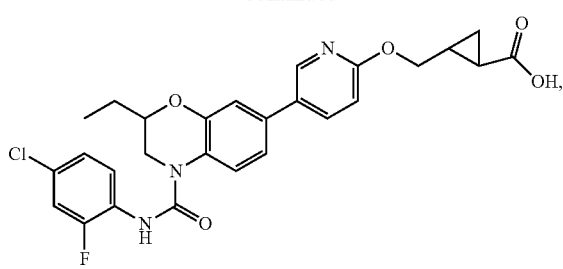
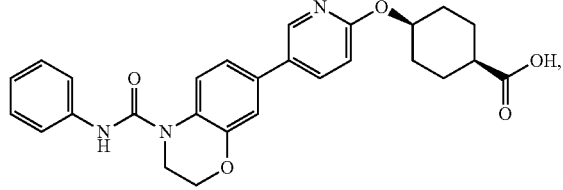
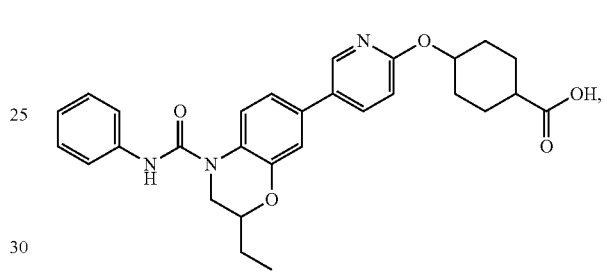
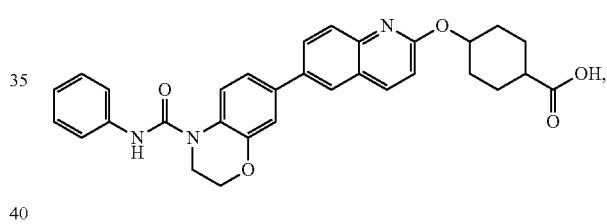
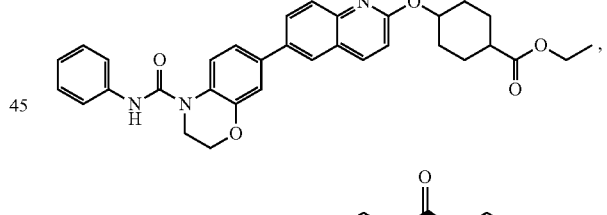
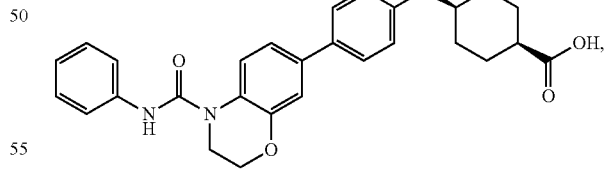
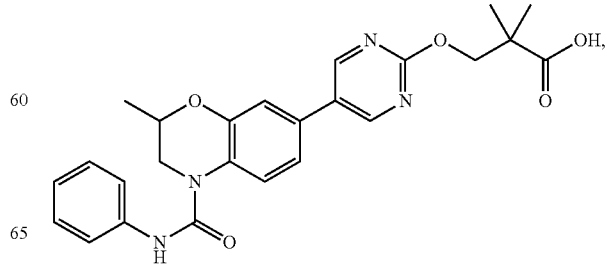

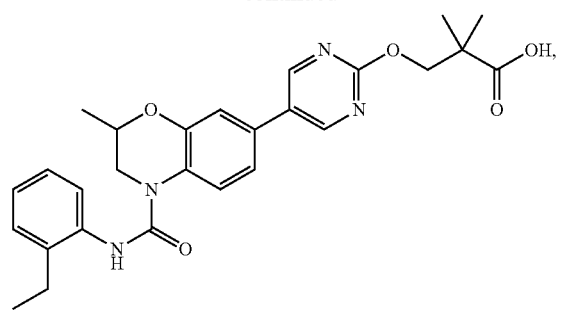
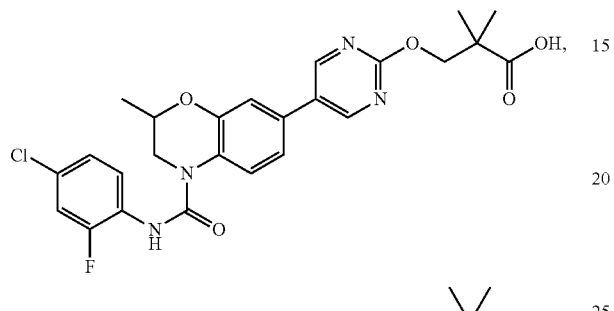
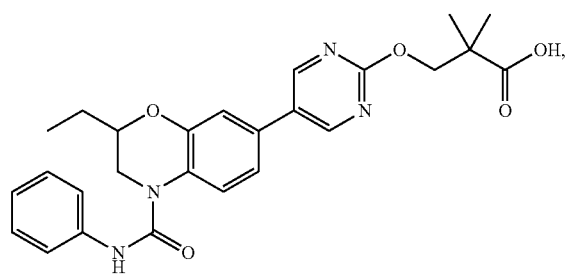
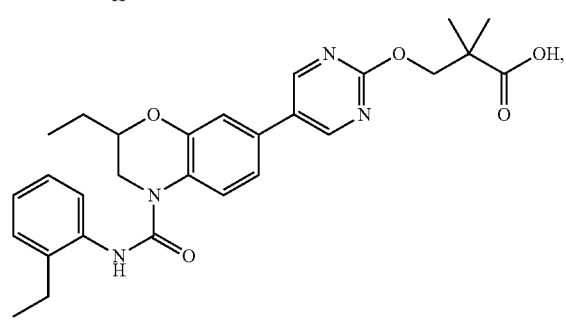
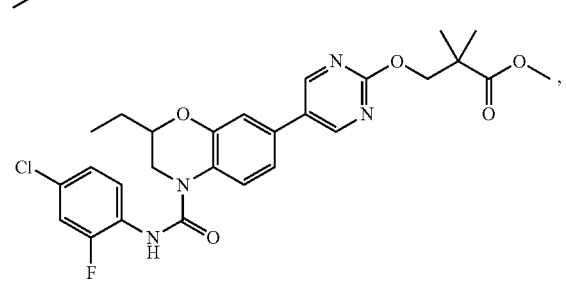
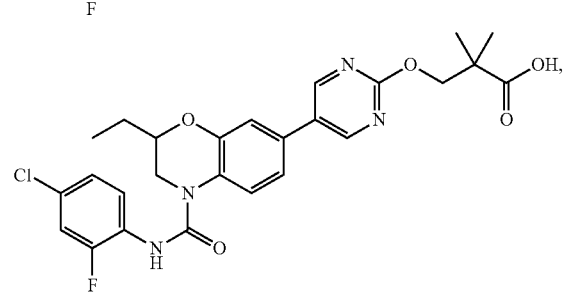
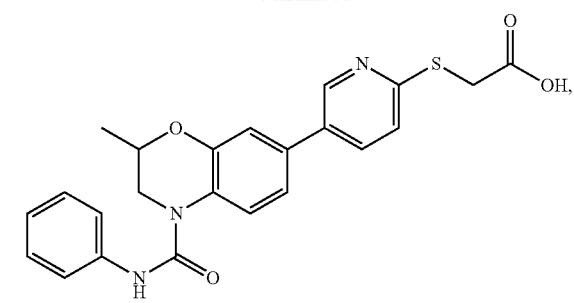
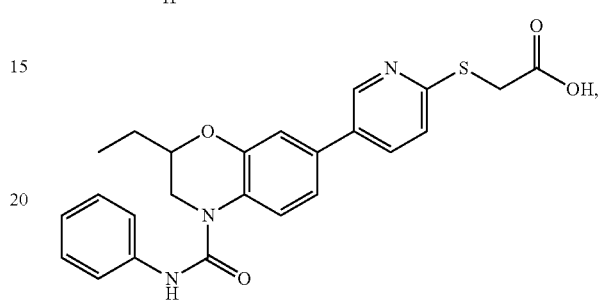
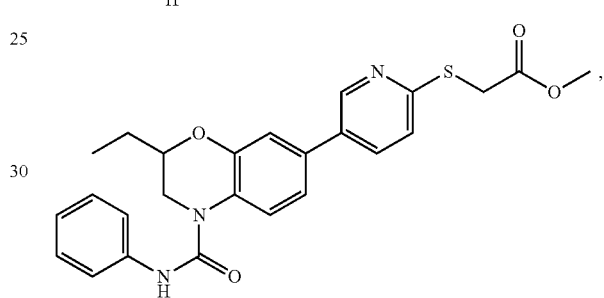
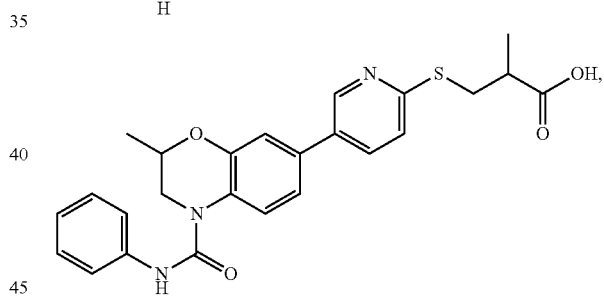
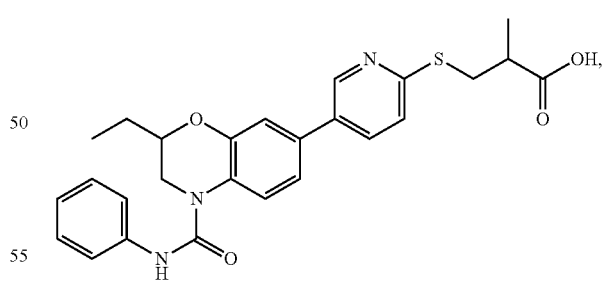
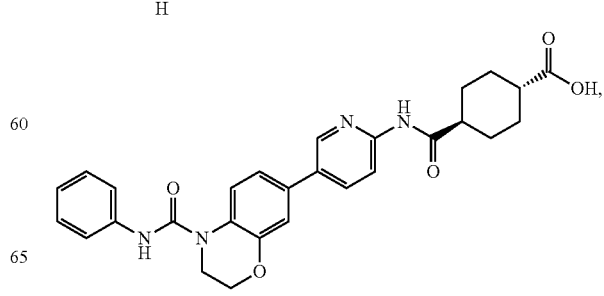

-continued
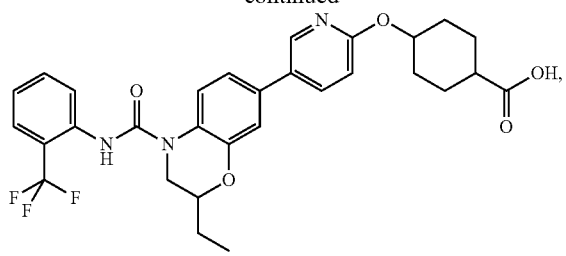
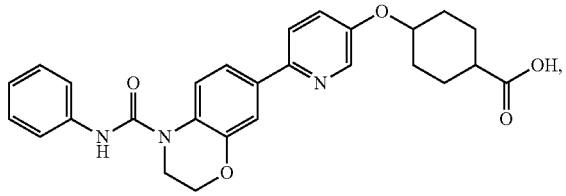
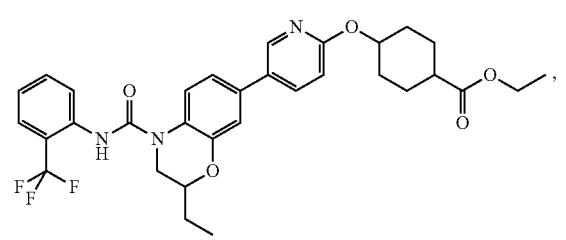
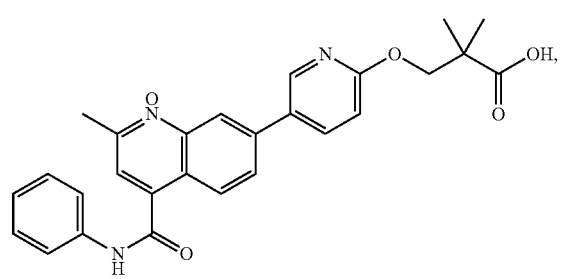
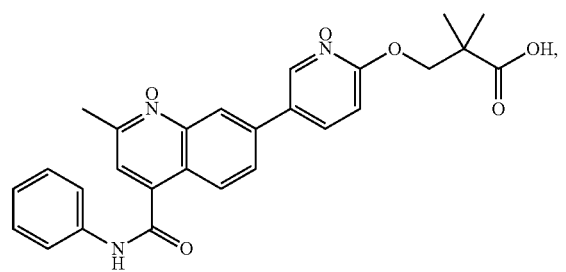
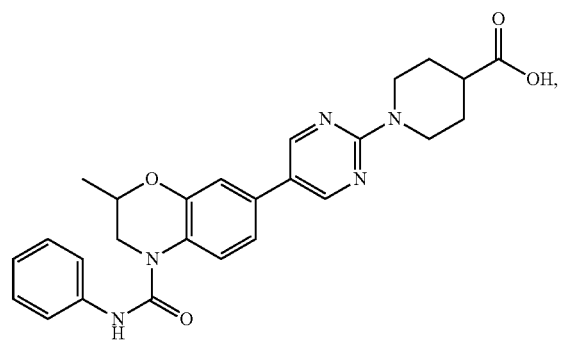
-continued
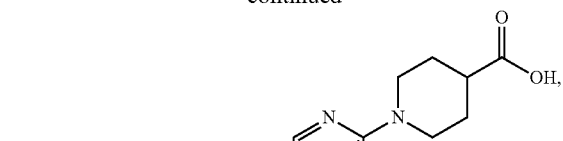
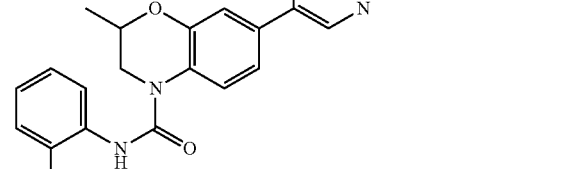
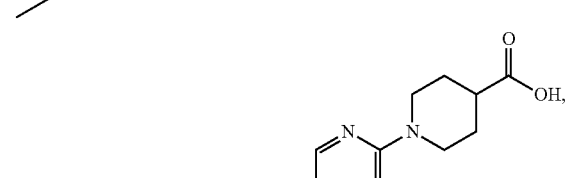
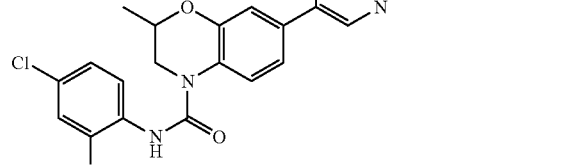
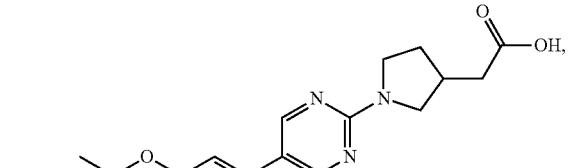
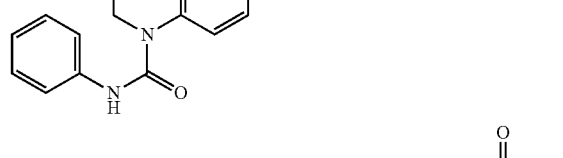
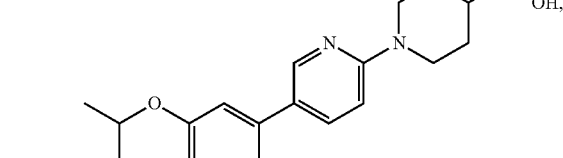
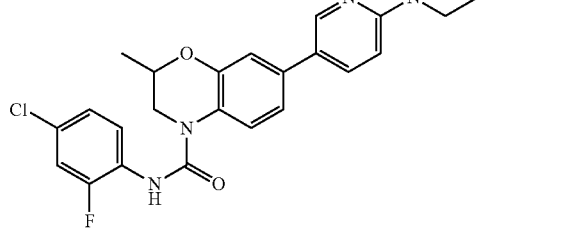

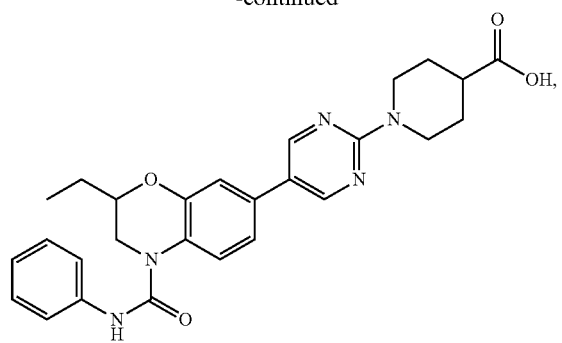
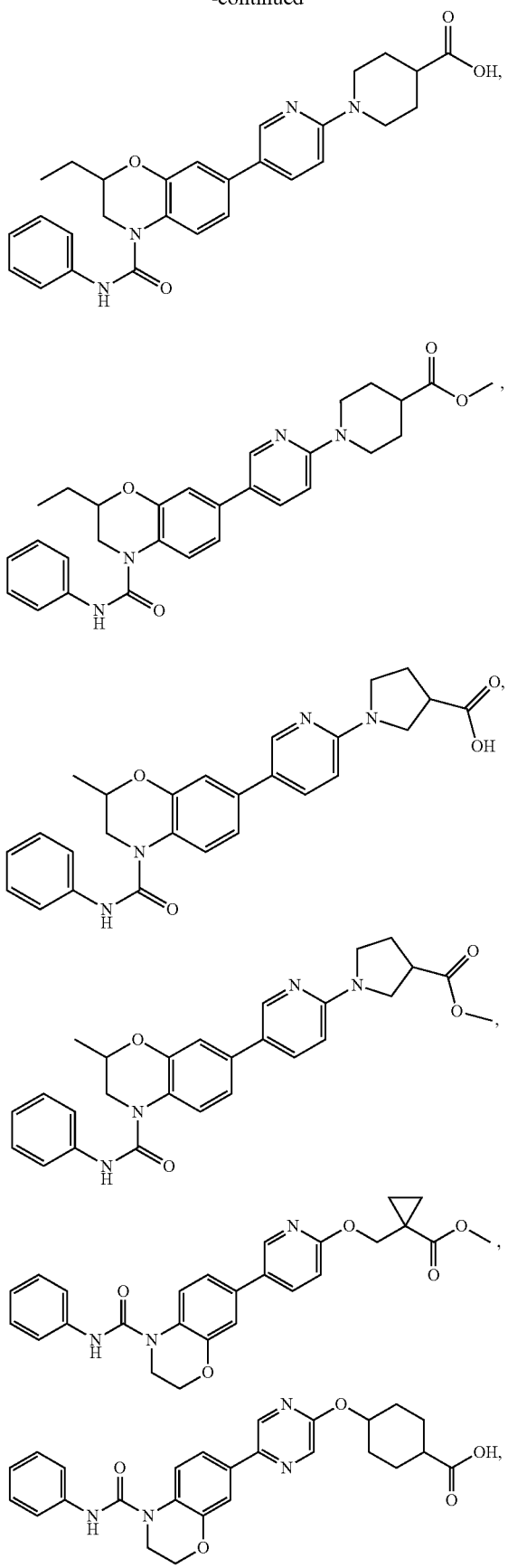

27
-continued
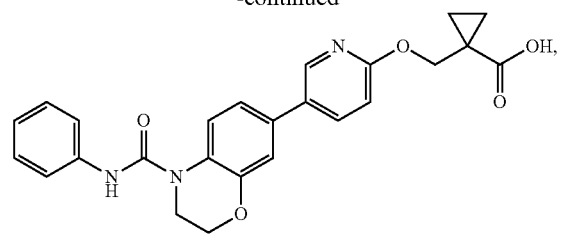
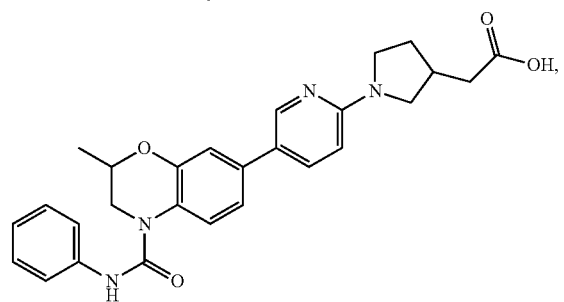
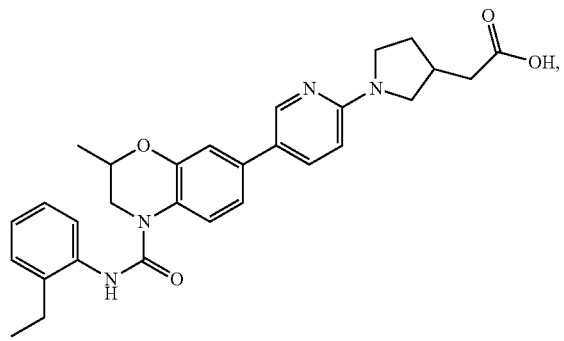
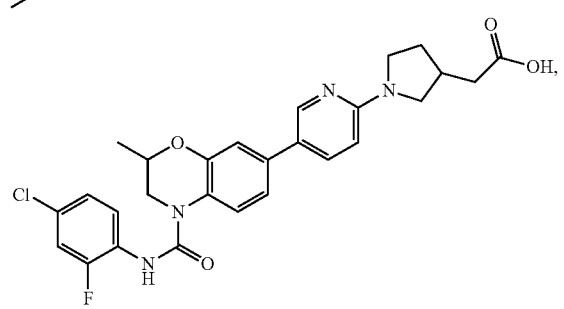
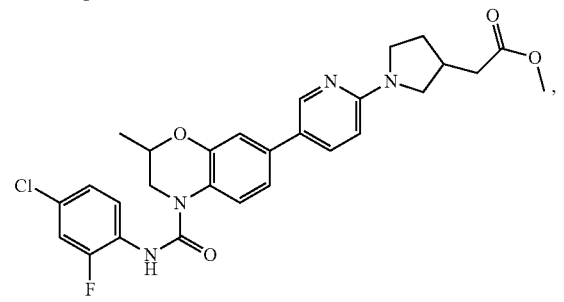
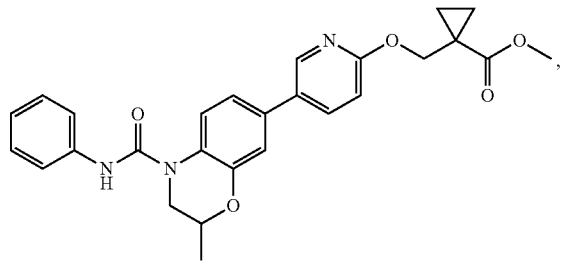
28
-continued
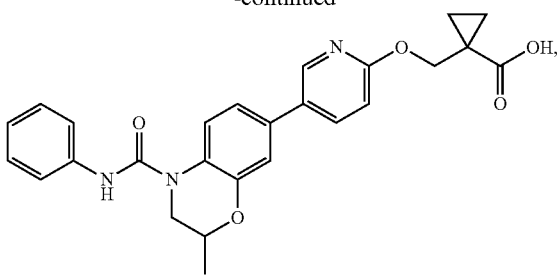
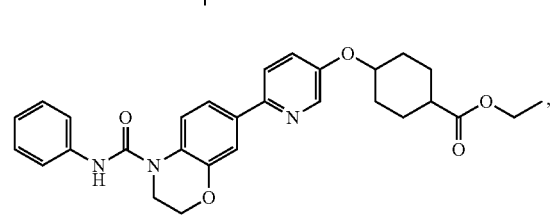
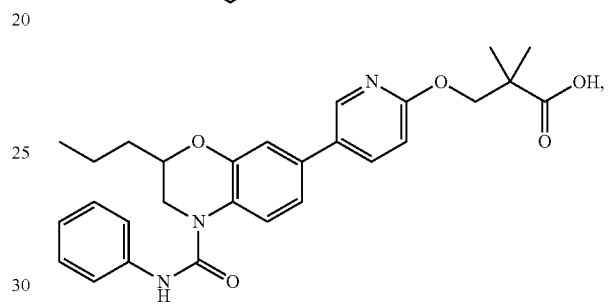
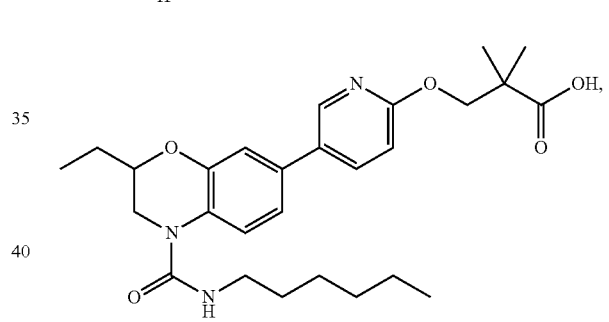
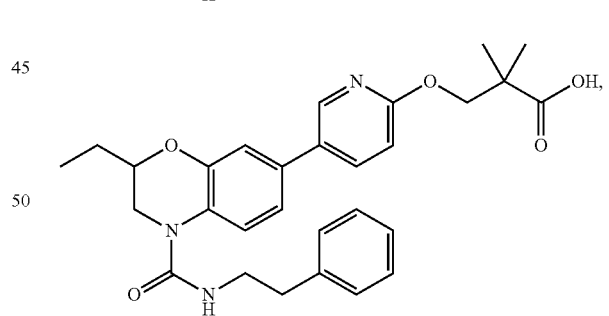
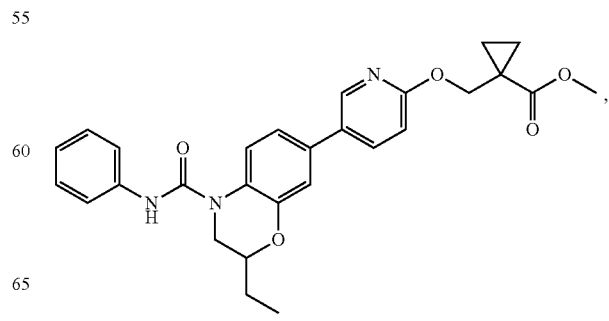

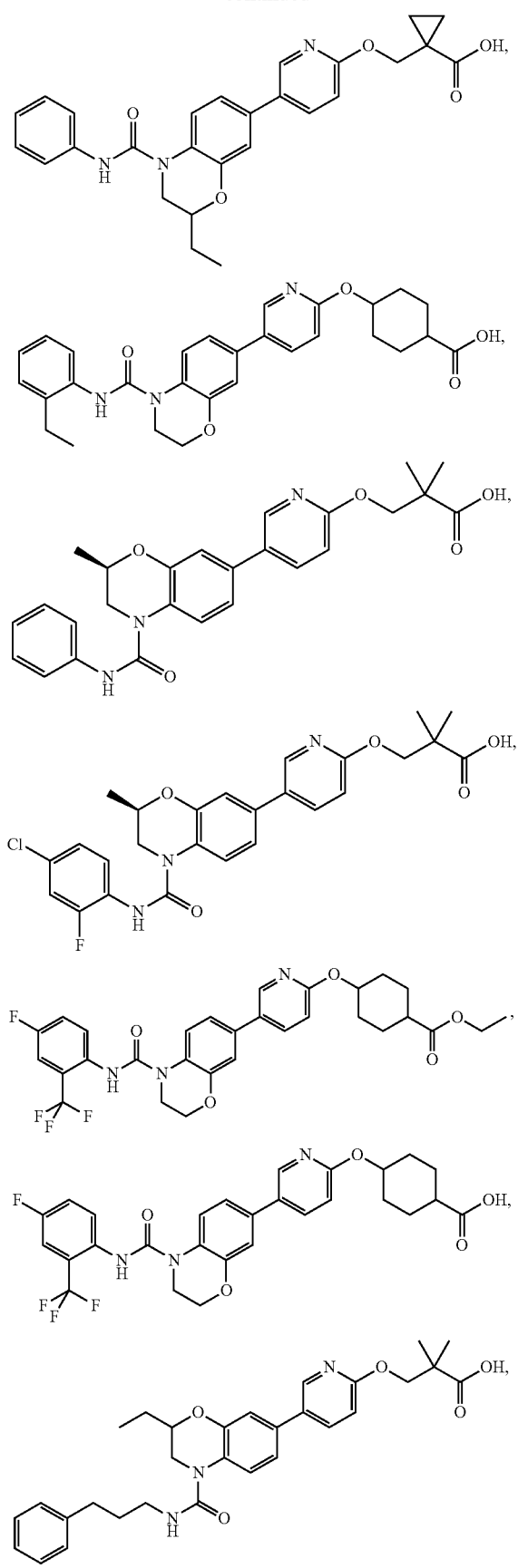
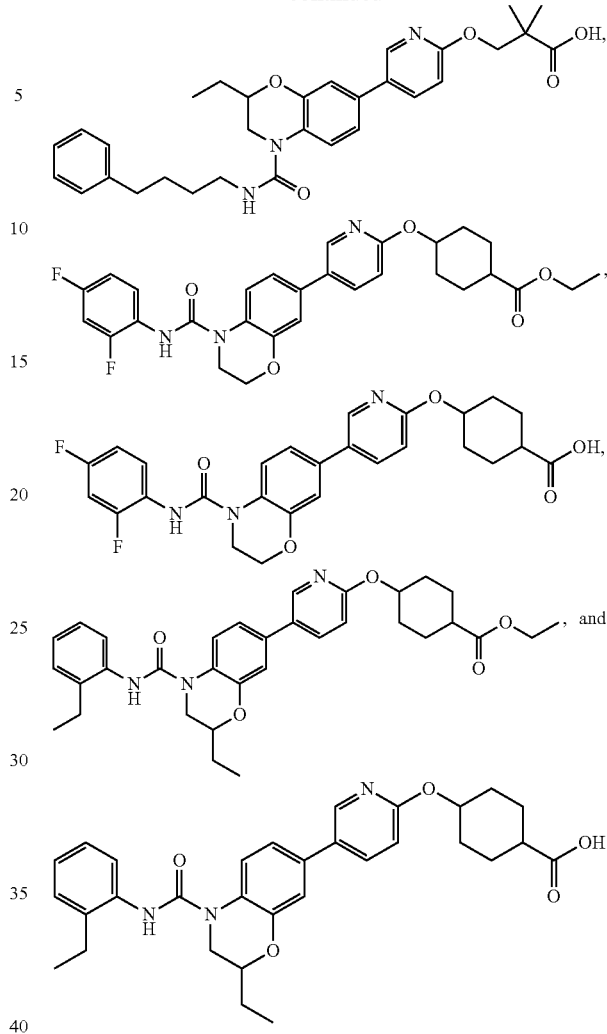

or pharmaceutically acceptable salts, solvates, esters and prodrugs thereof.

Several of the above-noted compounds exhibited IC50 values less than 3 μM in the assay described on page 84. Many compounds exhibited IC50 values less than 1 μM, with some compounds under <100 nM.

As used above, and throughout this disclosure, the following terms, unless otherwise indicated, shall be understood to have the following meanings:

"Patient" includes both humans and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. Lower alkyl means a group having about 1 to about 6 carbon atoms in the chain which may be straight or branched. Alkyl may be unsubstituted or optionally substituted by one or more substituents which may be the same or different, each substituent being independently selected from the group consisting of halo, alkyl, aryl, cycloalkyl, cyano, pyridine, alkoxy, alkylthio, amino, oxime (e.g., =N—OH), —NH (alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. Lower alkenyl means about 2 to about 6 carbon atoms in the chain which may be straight or branched. Alkenyl may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. Lower alkynyl means about 2 to about 6 carbon atoms in the chain which may be straight or branched. Non-limiting examples of suitable alkynyl groups include ethynyl, propynyl, 2-butynyl and 3-methylbutynyl. Alkynyl may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridine (including N-substituted pyridones), isoxazolyl, isothiazolyl, oxazolyl, thiazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y₁Y₂N—, Y₁Y₂N-alkyl-, Y₁Y₂NC(O)—, Y₁Y₂NSO₂— and —SO₂NY₁Y₂, wherein Y₁ and Y₂ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH₃)₂— and the like which form moieties such as, for example:

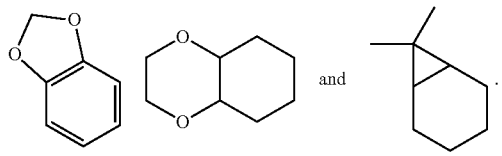

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

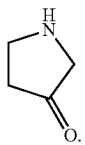

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

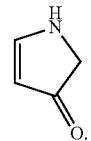

"Heterocyclenylalkyl" means a heterocyclenyl moiety as defined above linked via an alkyl moiety (defined above) to a parent core.

It should be noted that in heteroatom containing ring systems of this invention, there are no hydroxyl groups on carbon atoms adjacent to a N, O or S, as well as there are no N or S groups on carbon adjacent to another heteroatom. Thus, for example, in the ring:

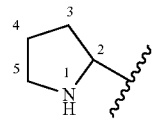

there is no —OH attached directly to carbons marked 2 and 5.

It should also be noted that tautomeric forms such as, for example, the moieties:

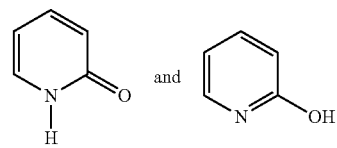 [SMILES: O=c1cccc[nH]1 ; Oc1ccccn1]

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkoxyalkyl-" means an alkyl-O-alkyl-group in which the alkyl group is as previously described. Non-limiting examples of suitable alkoxyalkyl groups include methoxymethyl, ethoxymethyl, n-propoxyethyl, isopropoxyethyl and n-butoxymethyl. The bond to the parent moiety is through the alkyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxyalkyl-" means an aryl-O-alkyl-group in which the aryl and aryl groups are as previously described. Non-limiting examples of suitable aryloxyalkyl groups include phenoxymethyl and naphthoxyethyl. The bond to the parent moiety is through the alkyl.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

The term "spirocyclyl" refers to a cyclic moiety whose two carbon atoms attached to the same carbon atom, for example, such as:

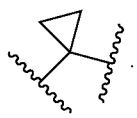 [SMILES: *C1(*)CC1]

"Alkylthio" means an alkyl-S— group in which the alkyl group is as previously described. Non-limiting examples of suitable alkylthio groups include methylthio and ethylthio. The bond to the parent moiety is through the sulfur.

"Alkylthioalkyl-" means an alkyl-S-alkyl-group in which the alkyl group is as previously described. Non-limiting examples of suitable alkylthioalkyl groups include methylthioethyl and ethylthiomethyl. The bond to the parent moiety is through the alkyl.

"Arylthio" means an aryl-S— group in which the aryl group is as previously described. Non-limiting examples of suitable arylthio groups include phenylthio and naphthylthio. The bond to the parent moiety is through the sulfur.

"Arylthioalkyl-" means an aryl-S-alkyl-group in which the aryl group is as previously described. Non-limiting examples of suitable arylthioalkyl groups include phenylthioethyl and phenylthiomethyl. The bond to the parent moiety is through the alkyl.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula IA or Formula IB, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula IA or Formula IB or a pharmaceutically acceptable salt, hydrate or solvate of the compound. The transformation may occur by various mechanisms (e.g., by metabolic or chemical processes), such as, for example, through hydrolysis in blood. A discussion of the use of pro-drugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula IA or Formula IB or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula IA or Formula IB contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula IA or Formula IB incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl, —C(OH)C(O)OY$^1$ wherein $Y^1$ is H, $(C_1-C_6)$alkyl or benzyl, —C(OY$^2$)Y$^3$ wherein $Y^2$ is $(C_1-C_4)$alkyl and $Y^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —C(Y$^4$)Y$^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, (2004) 93(3), pp. 601-611 describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, (2004) 5(1), article 12; and A. L. Bingham et al, *Chem. Commun.*, (2001) pp. 603-604. A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "effective" or "therapeutically effective" is used herein, unless otherwise indicated, to describe an amount of a compound or composition which, in context, is used to produce or effect an intended result or therapeutic effect as understood in the common knowledge of those skilled in the art.

The compounds of Formula IA or Formula IB can form salts which are also within the scope of this invention. Reference to a compound of Formula IA or Formula IB herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula IA or Formula IB contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula IA or Formula IB may be formed, for example, by reacting a compound of Formula IA or Formula IB with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) pp. 1-19; P. Gould, *International J. of Pharmaceutics* (1986) (2001) 33, pp. 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula IA or Formula IB, and salts, solvates, esters and prodrugs thereof, may exist in their tautomeric form (for example, as an amide or imino ether). All such tautomeric forms are contemplated herein as part of the present invention.

The compounds of Formula IA or Formula IB may contain asymmetric or chiral centers, and, therefore, exist in different stereoisomeric forms. It is intended that all stereoisomeric forms of the compounds of Formula IA or Formula IB as well as mixtures thereof, including racemic mixtures, form part of the present invention. In addition, the present invention embraces all geometric and positional isomers. For example, if a compound of Formula IA or Formula IB incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula IA or Formula IB may be atropisomers (e.g., substituted biaryls) and are considered as part of this invention. Enantiomers can also be separated by use of chiral HPLC column.

It is also possible that the compounds of Formula IA or Formula IB may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula IA or Formula IB incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula IA or Formula IB (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula IA or Formula IB can be useful for medical imaging purposes. e.g., those labeled with positron-emitting isotopes like $^{11}C$ or $^{18}F$ can be useful for application in Positron Emission Tomography (PET) and those labeled with gamma ray emitting isotopes like $^{123}$I can be useful for application in Single Photon Emission Computed Tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula IA or Formula IB, in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula IA or Formula IB, and of the salts, solvates, esters and prodrugs of the compounds of Formula IA or Formula IB, are intended to be included in the present invention.

The compounds according to the invention have pharmacological properties. The compounds of Formula IA or Formula IB are inhibitors of DGAT, particularly DGAT1, and can be useful for the therapeutic and/or prophylactic treatment of diseases that are modulated by DGAT, particularly by DGAT1, such as, for example, metabolic syndrome, diabetes (e.g., Type 2 diabetes mellitus), obesity and the like.

The invention also includes methods of treating diseases that are modulated by DGAT, particularly by DGAT1.

The invention also includes methods of treating metabolic syndrome, diabetes (e.g., Type 2 diabetes mellitus), and obesity in a patient by administering at least one compound of Formula IA or Formula IB to said patient.

Diabetes refers to a disease process derived from multiple causative factors and is characterized by elevated levels of plasma glucose, or hyperglycemia in the fasting state or after administration of glucose during an oral glucose tolerance test. Persistent or uncontrolled hyperglycemia is associated with increased and premature morbidity and mortality. Abnormal glucose homeostasis is associated with alterations of the lipid, lipoprotein and apolipoprotein metabolism and other metabolic and hemodynamic disease. As such, the diabetic patient is at especially increased risk of macrovascular and microvascular complications, including coronary heart disease, stroke, peripheral vascular disease, hypertension, nephropathy, neuropathy, and retinopathy. Accordingly, therapeutic control of glucose homeostasis, lipid metabolism and hypertension are critically important in the clinical management and treatment of diabetes mellitus.

There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissue (muscle, liver and adipose tissue), and the plasma insulin levels, while elevated, are insufficient to overcome the pronounced insulin resistance.

Insulin resistance is not associated with a diminished number of insulin receptors but rather to a post-insulin receptor binding defect that is not well understood. This resistance to insulin responsiveness results in insufficient insulin activation of glucose uptake, oxidation and storage in muscle, and inadequate insulin repression of lipolysis in adipose tissue and of glucose production and secretion in the liver.

The available treatments for Type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic [beta]-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides are a class of agents that can increase insulin sensitivity and bring about some degree of correction of hyperglycemia. However, the biguanides can induce lactic acidosis and nausea/diarrhea.

The glitazones (i.e. 5-benzylthiazolidine-2,4-diones) are a separate class of compounds with potential for the treatment of Type 2 diabetes. These agents increase insulin sensitivity in muscle, liver and adipose tissue in several animal models of Type 2 diabetes, resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type 2 diabetes are agonists of the alpha, gamma or delta subtype, or a combination of these, and in many cases are chemically different from the glitazones (i.e., they are not thiazolidinediones). Serious side effects (e.g. liver toxicity) have been noted in some patients treated with glitazone drugs, such as troglitazone.

Additional methods of treating the disease are currently under investigation. New biochemical approaches include treatment with alpha-glucosidase inhibitors (e.g. acarbose) and protein tyrosine phosphatase-1B (PTP-1B) inhibitors.

Compounds that are inhibitors of the dipeptidyl peptidase-IV (DPP-IV) enzyme are also under investigation as drugs that may be useful in the treatment of diabetes, and particularly Type 2 diabetes.

The invention includes compositions, e.g., pharmaceutical compositions, comprising at least one compound of Formula IA or Formula IB. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Other carriers include Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, or gamma-cyclodextrin or analogs thereof. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

The therapeutic agents of the present invention are preferably formulated in pharmaceutical compositions and then, in accordance with the methods of the invention, administered to a subject, such as a human subject, in a variety of forms adapted to the chosen route of administration. For example, the therapeutic agents may be formulated for intravenous administration. The formulations may, however, include those suitable for oral, rectal, vaginal, topical, nasal, ophthalmic, or other parenteral administration (including subcutaneous, intramuscular, intrathecal, intraperitoneal and intratumoral, in addition to intravenous) administration.

Formulations suitable for parenteral administration conveniently include a sterile aqueous preparation of the active agent, or dispersions of sterile powders of the active agent, which are preferably isotonic with the blood of the recipient. Parenteral administration of the therapeutic agents (e.g., through an I.V. drip) is an additional form of administration. Isotonic agents that can be included in the liquid preparation include sugars, buffers, and sodium chloride. Solutions of the active agents can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the first and/or second therapeutic agents, or as a solution or suspension in an aqueous liquor or non-aqueous liquid such as a syrup, an elixir, an emulsion, or a draught. Such compositions and preparations may contain at least about 0.1 wt-% of the active agent. The amounts of the therapeutic agents should be such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preferably the compound is administered orally, intraperitoneally, or intravenously or intrathecally or some suitable combination(s) thereof.

Methods of administering small molecule therapeutic agents are well-known in the art.

The therapeutic agents described in the present disclosure can be administered to a subject alone or together (coadministered, optionally but not necessarily, in a single formulation) with other active agents as described herein, and are preferably administered with a pharmaceutically acceptable buffer. The therapeutic agents can be combined with a variety of physiological acceptable carriers, additives for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the therapeutic agent (i.e., the active agent) into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering the therapeutic agents to a subject in an amount effective to produce the desired effect. The therapeutic agents can be administered as a single dose or in multiple doses. Useful dosages of the active agents can be determined by comparing their in vitro activity and the in vivo activity in animal models.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula IA or Formula IB, or a pharmaceutically acceptable salt, solvate, ester or prodrug of said compound and a pharmaceutically acceptable carrier, vehicle or diluent.

Another aspect of the invention includes pharmaceutical compositions comprising at least one compound of Formula IA or Formula IB and at least one other therapeutic agent in combination. Non-limiting examples of such combination agents are described below. The agents in the combination can be administered together as a joint administration (e.g., joint single pill), separately, one after the other in any order and the like as is well known in the art.

In the combination therapies of the present invention, an effective amount can refer to each individual agent or to the combination as a whole, wherein the amounts of all agents administered are together effective, but wherein the component agent of the combination may not be present individually in an effective amount.

Combination Therapy

Accordingly, in one embodiment, the present invention provides methods for treating a Condition in a patient, the method comprising administering to the patient one or more Compounds of Formula IA or Formula IB, or a pharmaceutically acceptable salt or solvate thereof and at least one additional therapeutic agent that is not a Compound of Formula IA or Formula IB, wherein the amounts administered are together effective to treat or prevent a Condition.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts).

In one embodiment, the one or more Compounds of Formula IA or Formula IB is administered during a time when the additional therapeutic agent(s) exert their prophylactic or therapeutic effect, or vice versa.

In another embodiment, the one or more Compounds of Formula IA or Formula IB and the additional therapeutic agent(s) are administered in doses commonly employed when such agents are used as monotherapy for treating a Condition.

In another embodiment, the one or more Compounds of Formula IA or Formula IB and the additional therapeutic agent(s) are administered in doses lower than the doses commonly employed when such agents are used as monotherapy for treating a Condition.

In still another embodiment, the one or more Compounds of Formula IA or Formula IB and the additional therapeutic agent(s) act synergistically and are administered in doses lower than the doses commonly employed when such agents are used as monotherapy for treating a Condition.

In one embodiment, the one or more Compounds of Formula IA or Formula IB and the additional therapeutic agent(s) are present in the same composition. In one embodiment, this composition is suitable for oral administration. In another embodiment, this composition is suitable for intravenous administration.

The one or more Compounds of Formula IA or Formula IB and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

In one embodiment, the administration of one or more Compounds of Formula IA or Formula IB and the additional therapeutic agent(s) may inhibit the resistance of a Condition to these agents.

In one embodiment, when the patient is treated for diabetes, a diabetic complication, impaired glucose tolerance or impaired fasting glucose, the other therapeutic is an antidiabetic agent which is not a Compound of Formula IA or Formula IB.

In another embodiment, the other therapeutic agent is an agent useful for reducing any potential side effect of a Compound of Formula IA or Formula IB. Such potential side effects include, but are not limited to, nausea, vomiting, headache, fever, lethargy, muscle aches, diarrhea, general pain, and pain at an injection site.

In one embodiment, the other therapeutic agent is used at its known therapeutically effective dose. In another embodiment, the other therapeutic agent is used at its normally prescribed dosage. In another embodiment, the other therapeutic agent is used at less than its normally prescribed dosage or its known therapeutically effective dose.

Examples of antidiabetic agents useful in the present methods for treating diabetes or a diabetic complication include a sulfonylurea; an insulin sensitizer (such as a PPAR agonist, a DPP-IV inhibitor, a PTP-1B inhibitor and a glucokinase activator); a glucosidase inhibitor; an insulin secretagogue; a hepatic glucose output lowering agent; an anti-obesity agent; a meglitinide; an agent that slows or blocks the breakdown of starches and sugars in vivo; an histamine $H_3$ receptor antagonist; a sodium glucose uptake transporter 2 (SGLT-2) inhibitor; a peptide that increases insulin production; and insulin or any insulin-containing composition.

In one embodiment, the antidiabetic agent is an insulin sensitizer or a sulfonylurea.

Non-limiting examples of sulfonylureas include glipizide, tolbutamide, glyburide, glimepiride, chlorpropamide, acetohexamide, gliamilide, gliclazide, glibenclamide and tolazamide.

Non-limiting examples of insulin sensitizers include PPAR activators, such as rosiglitazone, pioglitazone and englitazone; biguanidines such as metformin and phenformin; DPP-IV inhibitors; PTP-1B inhibitors; and α-glucokinase activators, such as miglitol, acarbose, and voglibose.

Non-limiting examples of DPP-IV inhibitors useful in the present methods include sitagliptin (Januvia™, Merck), saxagliptin, denagliptin, vildagliptin (Galvus™, Novartis), alogliptin, alogliptin benzoate, ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer), RO-0730699 (Roche) or a combination of sitagliptin/metformin HCl (Janumet™, Merck).

Non-limiting examples of SGLT-2 inhibitors useful in the present methods include dapagliflozin and sergliflozin, AVE2268 (Sanofi-Aventis) and T-1095 (Tanabe Seiyaku).

Non-limiting examples of hepatic glucose output lowering agents include Glucophage and Glucophage XR.

Non-limiting examples of histamine $H_3$ receptor antagonist agents include the following compound:

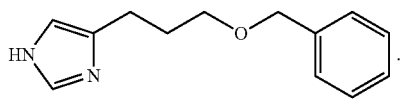 [SMILES: c1ccc(COCCCc2c[nH]cn2)cc1]

Non-limiting examples of insulin secretagogues include sulfonylurea and non-sulfonylurea drugs such as GLP-1, a GLP-1 mimetic, exendin, GIP, secretin, glipizide, chlorpropamide, nateglinide, meglitinide, glibenclamide, repaglinide and glimepiride.

Non-limiting examples of GLP-1 mimetics useful in the present methods include Byetta-Exenatide, Liraglutide, CJC-1131 (ConjuChem, Exenatide-LAR (Amylin), BIM-51077 (Ipsen/LaRoche), ZP-10 (Zealand Pharmaceuticals), and compounds disclosed in International Publication No. WO 00/07617.

The term "insulin" as used herein, includes all pyridinones of insulin, including long acting and short acting forms of insulin.

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In one embodiment, the antidiabetic agent is an anti-obesity agent.

Non-limiting examples of anti-obesity agents useful in the present methods for treating diabetes include a 5-HT2C agonist, such as lorcaserin; a neuropeptide Y antagonist; an MCR4 agonist; an MCH receptor antagonist; a protein hormone, such as leptin or adiponectin; an AMP kinase activator; and a lipase inhibitor, such as orlistat. Appetite suppressants are not considered to be within the scope of the anti-obesity agents useful in the present methods.

Non-limiting examples of meglitinides useful in the present methods for treating diabetes include repaglinide and nateglinide.

Non-limiting examples of insulin sensitizing agents include biguanides, such as metformin, metformin hydrochloride (such as GLUCOPHAGE® from Bristol-Myers Squibb), metformin hydrochloride with glyburide (such as GLUCOVANCE™ from Bristol-Myers Squibb) and buformin; glitazones; and thiazolidinediones, such as rosiglitazone, rosiglitazone maleate (AVANDIA™ from Glaxo-SmithKline), pioglitazone, pioglitazone hydrochloride (ACTOS™, from Takeda) ciglitazone and MCC-555 (Mitsubishi Chemical Co.)

In one embodiment, the insulin sensitizer is a thiazolidinedione.

In another embodiment, the insulin sensitizer is a biguanide.

In another embodiment, the insulin sensitizer is a DPP-IV inhibitor.

In a further embodiment, the antidiabetic agent is a SGLT-2 inhibitor.

Non-limiting examples of antidiabetic agents that slow or block the breakdown of starches and sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

The doses and dosage regimen of the other agents used in the combination therapies of the present invention for the treatment or prevention of a Condition can be determined by the attending clinician, taking into consideration the approved doses and dosage regimen in the package insert; the age, sex and general health of the patient; and the type and severity of the viral infection or related disease or disorder. When administered in combination, the Compound(s) of Formula IA or Formula IB and the other agent(s) for treating diseases or conditions listed above can be administered simultaneously or sequentially. This is particularly useful when the components of the combination are given on different dosing schedules, e.g., one component is administered once daily and another every six hours, or when the preferred pharmaceutical compositions are different, e.g. one is a tablet and one is a capsule. A kit comprising the separate dosage forms is therefore advantageous.

Generally, a total daily dosage of the one or more Compounds of Formula IA or Formula IB and the additional therapeutic agent(s) can, when administered as combination therapy, range from about 0.1 to about 2000 mg per day, although variations will necessarily occur depending on the target of the therapy, the patient and the route of administration. In one embodiment, the dosage is from about 0.2 to about 1000 mg/day, administered in a single dose or in 2-4 divided doses. In another embodiment, the dosage is from about 1 to about 500 mg/day, administered in a single dose or in 2-4 divided doses. In another embodiment, the dosage is from about 1 to about 200 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In a further embodiment, the dosage is from about 1 to about 20 mg/day, administered in a single dose or in 2-4 divided doses.

The compounds of the invention can be made according to the processes described below. The compounds of this invention are also exemplified in the examples below, which examples should not be construed as limiting the scope of the disclosure. Alternative mechanistic pathways and analogous structures within the scope of the invention may be apparent to those skilled in the art.

General Methods of Synthesis

The general methods described in this paragraph were used unless stated otherwise in the experimental procedures below. All solvents and reagents were used as received. Alternatively, anhydrous N,N-dimethylformamide, methylene chloride and tetrahydrofuran were obtained by drying bulk solvents purchased from Fisher Scientific on activated columns using The Pure-Solv PS-MD 3 system from Inovative Technology. Proton NMR spectra were obtained using a Varian XL-400 (400 MHz) or a Bruker Advance (500 MHz) instruments. $^1$H chemical shifts are reported in parts per million (ppm), measured relative to residual solvent peaks as an internal standard set to δ 7.26 ppm for chloroform-d, 3.34 for methanol-$d_4$ and 2.50 ppm for DMSO-$d_6$. LCMS analyses were performed using a PE SCIEX API-150EX single quadrupole mass spectrometer equipped with a Phenomenex Gemini $C_{18}$ column (5.0 μm, 50×4.6 mm); mobile phase A: 0.05% trifluoroacetic acid in water, B: 0.05% trifluoroacetic acid in acetonitrile; gradient: 90% A and 10% B to 5% A and 95% B in 5 minutes. Alternatively, LCMS analyses were performed using an Agilent 6140 quadrupole mass spectrometer equipped with a Zorbax SB-C-18 $C_{18}$ column (1.8 μm, 50×4.6 mm) heated at 50° C.; mobile phase A: 0.1% trifluoroacetic acid in water, B: 0.1% trifluoroacetic acid in acetonitrile; gradient: 90% A and 10% B to 5% A and 95% B in 3.5 minutes. Flash column chromatography was performed using Teledyne Isco RediSep silica columns and $C_{18}$ reverse phase columns. Preparative HPLC separations were performed on Gilson instruments (system 1: Gilson 322 pump, UV-vis detector 156, liquid handler 215 and injector 845Z; or system 2: pumps 333 & 334, liquid handler GX281, UV-vis detector 155) using Phenomenex columns (Gemini $C_{18}$ 5.0 μm, 100× 21.2 mm or 150×21.2 mm or 150×30.0 mm or 10 μm, 250× 50.0 mm or Gemini $C_6$-phenyl 5.0 μm, 21.2×150 mm or Synergi Fusion-RP 4.0 μm, 21.2×150 mm); mobile phase A: 0.1% trifluoroacetic (or formic acid) in water, B: 0.1% trifluoroacetic (or formic acid) in acetonitrile. Chiral resolutions of racemic mixtures were conducted on Varian HPLC systems (system 1, analytical: Varian/Dynamax pumps SD200, Varian Prostar autosampler 400 or 410, Varian Prostar PDA detector 335 and Varian Prostar CVM 500; system 2, preparative: Varian/Dynamax pumps SD200, Varian/Dynamax detector UV D-II) using Daicel Chiralpak IC columns (4.6× 150 mm or 20.0×250 mm). Microwave-mediated reactions were performed using a Biotage Initiator™ Synthesis System and using the standard 2 mL, 5 mL or 20 mL vials and lids. Preparative and analytical TLC were performed using Analtech Silica gel GF plates.

Section A

Preparation of Key Synthetic Intermediates

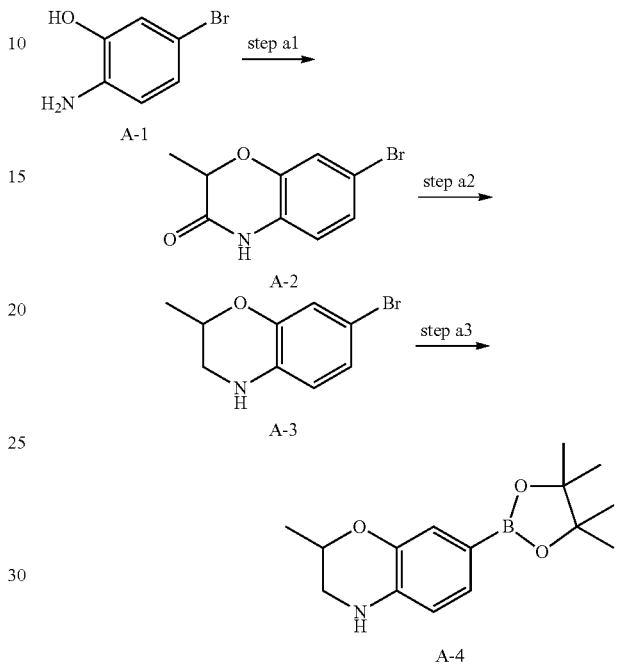

Scheme A1: Preparation of key-intermediates A-3 and A-4

Intermediate A-2

7-bromo-2-methyl-2H-benzo[b][1,4]oxazin-3(4H)-one—step a1

1,8-Diazabicyclo[5.4.0]undec-7-ene (145.0 μL, 0.975 mmol) was added at room temperature to a solution of 2-amino-5-bromophenol A-1 (200.0 mg, 1.064 mmol) and methyl 2-bromoacetate (115.0 μL, 0.886 mmol) in anhydrous 1-methylpyrrolidin-2-one (4.20 mL) under an atmosphere of argon, in a 10 mL microwave reactor vial. The sealed reaction mixture was heated at 180° C. for 3 mins under microwave irradiation and then diluted with ethyl acetate (25 mL). The organic layer was washed with brine (3×20 mL), dried over anhydrous magnesium sulfate, filtered and concentrated to dryness under reduced pressure. The crude residue was purified by flash column chromatography on silica gel (hexanes: ethyl acetate gradient) to give 7-bromo-2-methyl-2H-benzo [b][1,4]oxazin-3(4H)-one A-2 (217.0 mg, Yield=100%). MS (ESI) [M+1]$^+$ 242, 244.

Intermediate A-3

7-bromo-2-methyl-3,4-dihydro-2H-benzo[b][1,4] oxazine—step a2

Borane dimethyl sulfide complex (2 M solution in THF, 0.414 mL, 0.828 mmol) was added at room temperature to a solution of 7-bromo-2-methyl-2H-benzo[b][1,4]oxazin-3 (4H)-one A-2 (100.0 mg, 0.414 mmol) in anhydrous THF (4.10 mL) under an atmosphere of argon. The reaction mixture was heated to reflux for 2 h, cooled to room temperature, quenched with methanol (1.0 mL), stirred for 30 mins and concentrated to dryness under reduced pressure. The crude residue was purified by flash column chromatography on silica gel (hexanes:ethyl acetate gradient) to give 7-bromo-2-methyl-3,4-dihydro-2H-benzo[b][1,4]oxazine A-3 (92.9 mg, Yield=98%). MS (ESI) [M+1]+ 228, 230.

Intermediate A-4

2-methyl-7-(4,4,5,5-tetramethyl-1,3,2-dioxaborolan-2-yl)-3,4-dihydro-2H-benzo[b][1,4]oxazine—step a3

[1,1'-Bis(diphenylphosphino)ferrocene]dichloropalladium(II) complex with dichloromethane (1:1) (322.2 mg, 0.395 mmol), potassium acetate (2.32 g, 23.67 mmol), bis(pinacolato)diboron (2.40 g, 9.47 mmol) and 7-bromo-2-methyl-3,4-dihydro-2H-benzo[b][1,4]oxazine A-3 (1.80 g, 7.89 mmol) were mixed at room temperature in anhydrous dioxane (26.3 mL). The reaction was degassed several times under reduced pressure, placed under an argon atmosphere and stirred at 80° C. for 10 h. After cooling, the mixture was filtered through a celite pad, washed with ethyl acetate (60 mL) and concentrated to dryness under reduced pressure. The residue was purified by flash column chromatography on silica gel (hexanes to ethyl acetate gradient) to give 2-methyl-7-(4,4,5,5-tetramethyl-1,3,2-dioxaborolan-2-yl)-3,4-dihydro-2H-benzo[b][1,4]oxazine A-4 (1.536 g; Yield=70%). MS (ESI) [M+1]+ 276.

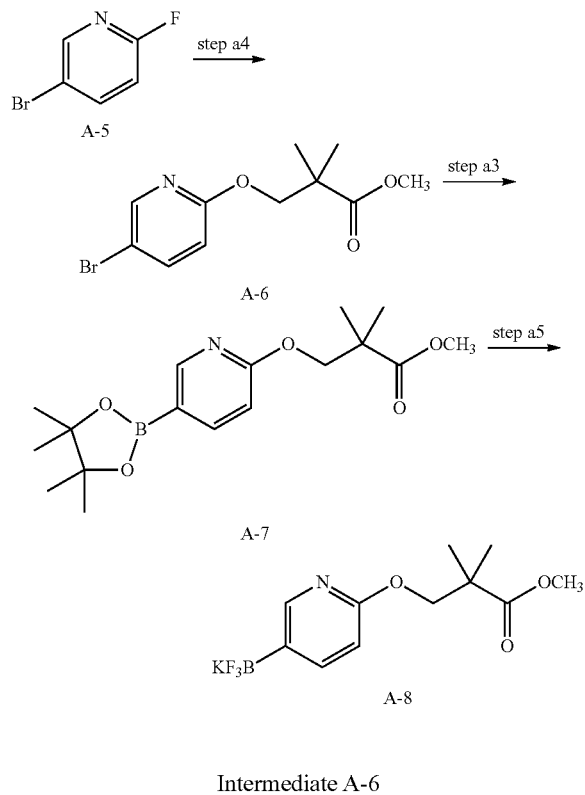

Intermediate A-6 methyl 3-(5-bromopyridin-2-yloxy)-2,2-dimethyl-propanoate—step a4

Sodium hydride (60% disp. in oil, 908.0 mg, 22.72 mmol) was added portionwise at room temperature to a solution of 5-bromo-2-fluoropyridine A-5 (1.16 mL, 11.36 mmol) and methyl 3-hydroxy-2,2-dimethylpropanoate (1.88 mL, 14.77 mmol) in anhydrous tetrahydrofuran (32.9 mL) and anhydrous 1,3-dimethyl-3,4,5,6-tetrahydro-2(1H)-pyrimidinone (5.0 mL) under an atmosphere of argon and in the presence of 4 Å molecular sieves. After 2 h of stirring at room temperature, the reaction mixture was heated at 50° C. for 10 h and then at 70° C. for 3 h. The suspension was cooled to room temperature, filtered over a thin celite pad, and the pad was rinsed with diethyl ether (150 mL). The filtrate was concentrated to a volume of ca. 5 mL, then diluted with diethyl ether (150 mL), quenched with water (90 mL) and decanted. The aqueous layer was extracted with diethyl ether (2×100 mL); the combined extracts were successively washed with water (3×70 mL), brine (70 mL), dried over anhydrous magnesium sulfate, filtered and concentrated to dryness under reduced pressure. The crude residue was purified by flash column chromatography on silica gel (100:0 to 80:20 hexanes:ethyl acetate gradient) to give methyl 3-(5-bromopyridin-2-yloxy)-2,2-dimethylpropanoate A-6 (1.796 g, Yield=55%). MS (ESI), [M+1]+ 288, 290.

Intermediate A-7 methyl 2,2-dimethyl-3-(5-(4,4,5,5-tetramethyl-1,3,2-dioxaborolan-2-yl)pyridin-2-yloxy)propanoate—step a3

Intermediate A-7 was prepared by the procedure described for step a3, using methyl 3-(5-bromopyridin-2-yloxy)-2,2-dimethylpropanoate A-6 as starting material. MS (ESI) [M+1]+ 336.

Intermediate A-8 potassium trifluoro(6-(3-methoxy-2,2-dimethyl-3-oxopropoxy)pyridin-3-yl)borate—step a5

Potassium hydrogen difluoride (150.4 mg, 1.93 mmol) was added at room temperature to a solution of methyl 2,2-dimethyl-3-(5-(4,4,5,5-tetramethyl-1,3,2-dioxaborolan-2-yl)pyridin-2-yloxy)propanoate A-7 (257.0 mg, 0.77 mmol) in a 2:1 mixture of water and methanol (3.90 mL). The reaction was stirred at room temperature in a polypropylene reactor for 4 h. The reaction mixture was concentrated to dryness under reduced pressure, the resulting solid residue was suspended in ice-cold water (150 mL), quickly filtered, washed with ice-cold diethyl ether (250 mL) and dried under high vacuum to give potassium trifluoro(6-(3-methoxy-2,2-dimethyl-3-oxopropoxy)pyridin-3-yl)borate A-8 as a white solid (242.0 mg; Yield=99%). $^1$H NMR (500 MHz, DMSO-$d_6$) δ ppm 1.22 (s, 6H), 3.60 (s, 3H), 4.20 (s, 2H), 6.50 (d, J=8.04 Hz, 1H), 7.52 (dd, J=1.58, 8.04 Hz, 1H), 7.98 (s, 1H).

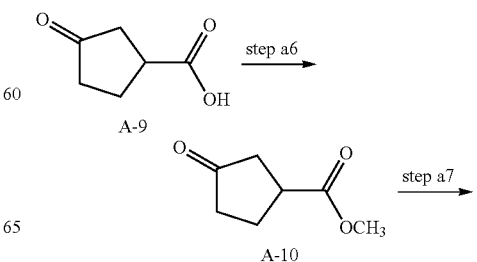

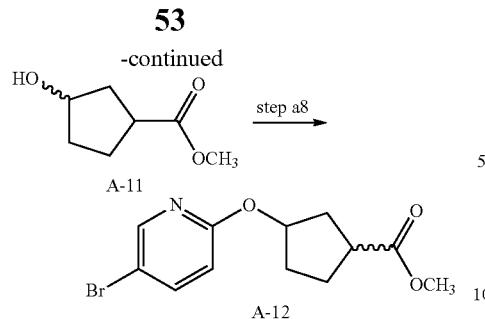

A-11

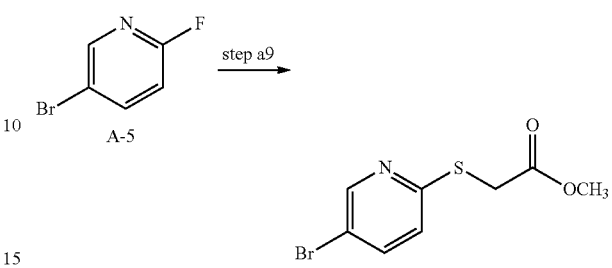

A-12

Intermediate A-10 methyl 3-oxocyclopentanecarboxylate—step a6

Methyl iodide (7.29 mL, 117.0 mmol) was added to a suspension of anhydrous potassium carbonate (2.44 g, 17.55 mmol) and 3-oxocyclopentanecarboxylic acid A-9 (1.50 g, 11.70 mmol) in dry acetone (38.0 mL) at room temperature under an atmosphere of argon. The reaction mixture was refluxed for 8.5 h, then cooled to room temperature, filtered over a celite pad, rinsed with acetone (150 mL) and concentrated to dryness under reduced pressure. The solid residue was suspended in methylene chloride (20 mL), filtered over a celite pad, and rinsed with methylene chloride (20 mL). The filtrate was concentrated to dryness under reduced pressure to give crude methyl α-oxocyclopentane-carboxylate A-10 (1.67 g, Yield=100%). This yellow oil was used for the next step without purification. MS (ESI), [M+1]$^+$ 143.

Intermediate A-11 methyl 3-hydroxycyclopentanecarboxylate—step a7

Sodium borohydride (442.6 mg, 11.70 mmol) was added portionwise to a solution of methyl 3-oxocyclopentane-carboxylate A-10 (1.66 g, 11.70 mmol) in absolute ethanol (42.0 mL) at 0° C. The reaction mixture was allowed to warm to room temperature and stirred for 90 mins, then quenched slowly with a 1 N aqueous solution of hydrogen chloride (10 mL), and concentrated to ca. 15 mL under reduced pressure. The aqueous layer was extracted with methylene chloride (3×50 mL); the combined extracts were dried over anhydrous magnesium sulfate, filtered and concentrated to dryness under reduced pressure to give crude methyl 3-hydroxycyclopentanecarboxylate A-11 as a yellow oil (1.33 g, Yield=79%). This material was used for next step without purification. MS (ESI), [M+1]$^+$ 145.

Intermediate A-12 methyl 3-(5-bromopyridin-2-yloxy)cyclopentane carboxylate—step a8

A solution of methyl 3-hydroxycyclopentanecarboxylate A-11 (500.0 mg, 3.00 mmol) in anhydrous toluene (10.0 mL) was added to a solution of 5-bromopyridin-2-ol (522.0 mg, 3.00 mmol) in anhydrous toluene (10.0 mL) at room temperature. Diisopropyl azodicarboxylate (1.57 g, 6.00 mmol) was then added dropwise, and the yellow-orange solution was stirred at room temperature for 12 h. The reaction mixture was then quenched with methanol (1.0 mL) and concentrated to dryness under reduced pressure. The residue was purified by flash column chromatography on silica gel (hexanes to ethyl acetate gradient) to give methyl 3-(5-bromopyridin-2-yloxy) cyclopentane carboxylate A-12 (462.0 mg, Yield=51%). MS (ESI), [M+Na]$^+$ 321, 323.

Scheme A4: Preparation of key-intermediate A-13

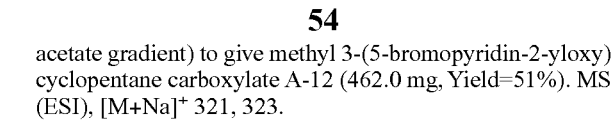

A-5

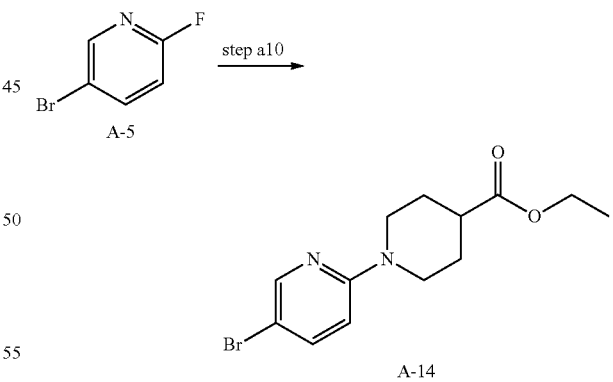

A-13

Intermediate A-13 methyl 2-(5-bromopyridin-2-ylthio)acetate—step a9

Potassium tert-butoxide (740.0 mg, 6.60 mmol) was added portionwise at room temperature to a solution of 5-bromo-2-fluoropyridine A-5 (0.31 mL, 3.00 mmol) and methyl 2-mercaptoacetate (0.55 mL, 6.00 mmol) in anhydrous 1-methylpyrrolidin-2-one (12.0 mL) under an argon atmosphere, in a 20 mL microwave reactor vial. The reaction mixture was sealed and heated at 90° C. for 3 mins under microwave irradiation, then successively cooled to room temperature, diluted with diethyl ether (150 mL), quenched with water (80 mL) and decanted. The aqueous layer was extracted with diethyl ether (2×150 mL); the combined extracts were sequentially washed with water (2×150 mL), brine (100 mL), dried over anhydrous magnesium sulfate, filtered and concentrated to dryness under reduced pressure. The crude residue was purified by flash column chromatography on silica gel (hexanes:ethyl acetate gradient) to give methyl 2-(5-bromopyridin-2-ylthio)acetate A-13 (300.0 mg, Yield=39%). MS (ESI), [M+1]$^+$ 262, 264.

Scheme A5: Preparation of key-intermediate A-14

A-5

A-14

Intermediate A-14 ethyl 1-(5-bromopyridin-2-yl)piperidine-4-carboxylate—step a10

5-Bromo-2-fluoropyridine A-5 (0.31 mL, 3.0 mmol) and ethyl piperidine-4-carboxylate (1.39 mL, 9.0 mmol) were dissolved in anhydrous pyridine (2.0 mL) at room temperature under an argon atmosphere, in a 10 mL microwave reactor vial. The reaction mixture was sealed and heated at 190°

C. for 60 mins under microwave irradiation, then successively cooled to room temperature, diluted with methylene chloride (60 mL), quenched with a 1 N aqueous solution of hydrogen chloride (40 mL) and decanted. The aqueous layer was extracted with methylene chloride (2×100 mL); the combined extracts were sequentially washed with water (70 mL), brine (70 mL), dried over anhydrous magnesium sulfate, filtered and concentrated to dryness under reduced pressure. The crude residue was purified by flash column chromatography on silica gel (hexanes:ethyl acetate gradient) to give ethyl 1-(5-bromopyridin-2-yl)piperidine-4-carboxylate A-14 (935.0 mg, Yield=99%). MS (ESI), [M+1]$^+$ 313, 315.

Scheme A6: Preparation of key-intermediate (R)-A-18

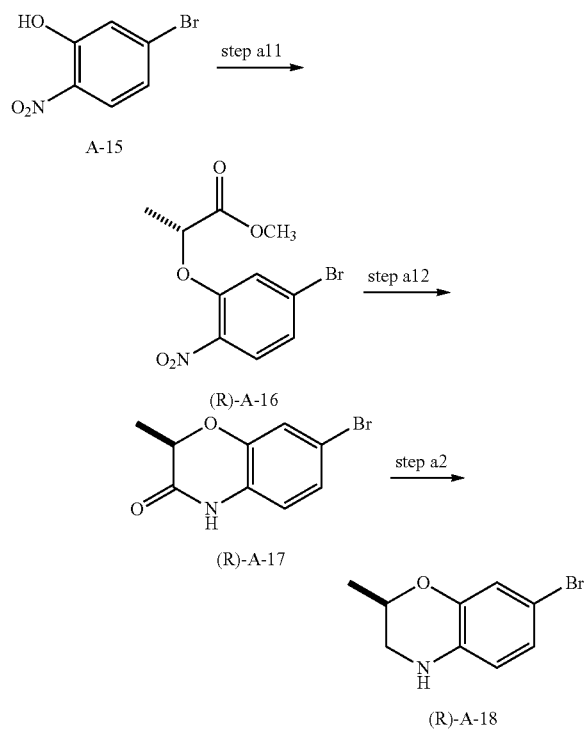

Intermediate (R)-A-16

(R)-methyl 2-(5-bromo-2-nitrophenoxy)propanoate—step a11

Triphenylphosphine (624.0 mg, 2.38 mmol) was added at room temperature to a solution of 5-bromo-2-nitrophenol A-15 (400.0 mg, 1.83 mmol) and methyl(−)—(S)-lactate (0.149 mL, 1.56 mmol) in anhydrous methylene chloride (18.3 mL) under an atmosphere of argon. After 10 mins of stirring, the reaction mixture was cooled to 0° C. and diisopropyl azodicarboxylate (0.360 mL, 1.83 mmol) was added dropwise. The orange solution was warmed to room temperature, stirred for 12 h, then concentrated to ca. 1.0 mL, diluted with pentane (7 mL) and diethyl ether (8 mL), filtered and rinsed with diethyl ether-pentane (15 mL). The filtrate was concentrated to dryness under reduced pressure, and the residue was purified by flash column chromatography on silica gel (hexanes to ethyl acetate gradient) to give (R)-methyl 2-(5-bromo-2-nitrophenoxy)propanoate (R)-A-16 as a yellow solid (525.0 mg; Yield=94%). MS (ESI) [M+1]$^+$ 304, 306.

Intermediate (R)-A-17

(R)-7-bromo-2-methyl-2H-benzo[b][1,4]oxazin-3 (4H)-one—step a12

Iron powder (1.91 g, 34.15 mmol) and (R)-methyl 2-(5-bromo-2-nitrophenoxy)propanoate (R)-A-16 (525.0 mg, 1.71 mmol) were heated at 50° C. in glacial acetic acid (10.5 mL) for 5 h. The reaction mixture was cooled to room temperature, diluted with ethyl acetate (80 mL), filtered over a pad of celite, and rinsed with ethyl acetate (80 mL). The filtrate was successively washed with water (2×30 mL), a saturated aqueous solution of sodium bicarbonate (40 mL), then dried over anhydrous magnesium sulfate, filtered and concentrated to dryness under reduced pressure. The resulting white crystalline solid (R)-7-bromo-2-methyl-2H-benzo [b][1,4]oxazin-3(4H)-one (R)-A-17 (399.4 mg, Yield=96%) was used as such for next step without purification. MS (ESI) [M+1]$^+$ 242, 244.

Intermediate (R)-A-18

(R)-7-bromo-2-methyl-3,4-dihydro-2H-benzo[b][1,4]oxazine—step a2

Intermediate (R)-A-18 was prepared by the procedure described for step a2, using (R)-7-bromo-2-methyl-2H-benzo[b][1,4]oxazin-3(4H)-one (R)-A-17 as starting material. MS (ESI) [M+1]$^+$ 228, 230; ee=96% (rt=5.195 min for (R)-A-18, rt=6.283 min for (S)-A-18; using Daicel Chiralpak AD column (4.6×150 mm) on Varian HPLC system 1 and eluting with 10% ethanol in hexanes:diethylamine 99.5:0.5, isocratic gradient at 1 mL/min).

Scheme A7: Preparation of key-intermediate A-20

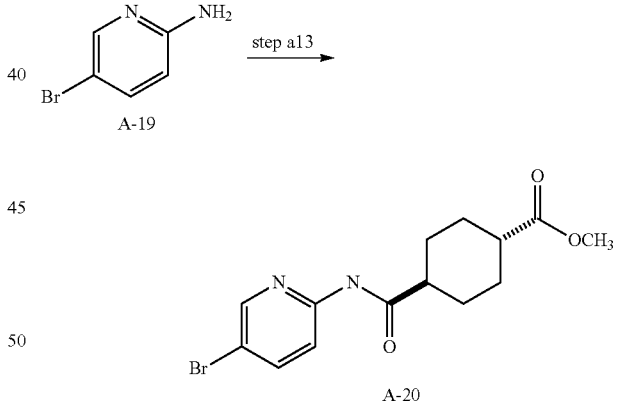

Intermediate A-20

(1r,4r)-methyl 4-(5-bromopyridin-2-ylcarbamoyl) cyclohexanecarboxylate—step a13

(1r,4r)-4-(Methoxycarbonyl)cyclohexanecarboxylic acid (538.3 mg, 2.89 mmol), N,N,N',N'-tetramethyl-O-(7-azabenzotriazol-1-yl)uronium hexafluorophosphate (1.6 g, 4.21 mmol) and N-ethyl-N,N-diisopropylamine (1.5 mL, 8.61 mmol) were successively added at room temperature to a solution of 5-bromopyridin-2-amine A-19 (500.0 mg, 2.89 mmol) in methylene chloride (40.0 mL) under an atmosphere of nitrogen. The reaction mixture was stirred at room temperature for 17 h and then concentrated to dryness under reduced pressure. The crude residue was purified by flash column chromatography on silica gel (hexanes to ethyl acetate gradient) to give (1r,4r)-methyl 4-(5-bromopyridin-2-ylcarbamoyl)cyclohexanecarboxylate A-20 as a beige solid (525.0 mg; Yield=94%). $^1$H NMR (500 MHz, CHLOROFORM-d) δ ppm 1.46-1.54 (m, 2H), 1.57-1.66 (m, 2H), 2.05-2.14 (m, 4H), 2.26-2.38 (m, 2H), 3.70 (s, 3H), 7.80 (dd, J=2.00, 8.50 Hz, 1H), 8.17 (d, J=8.50 Hz, 1H), 8.21 (br s, 1H), 8.31 (d, J=2.00 Hz, 1H).

Section B

Preparation of Example Compounds

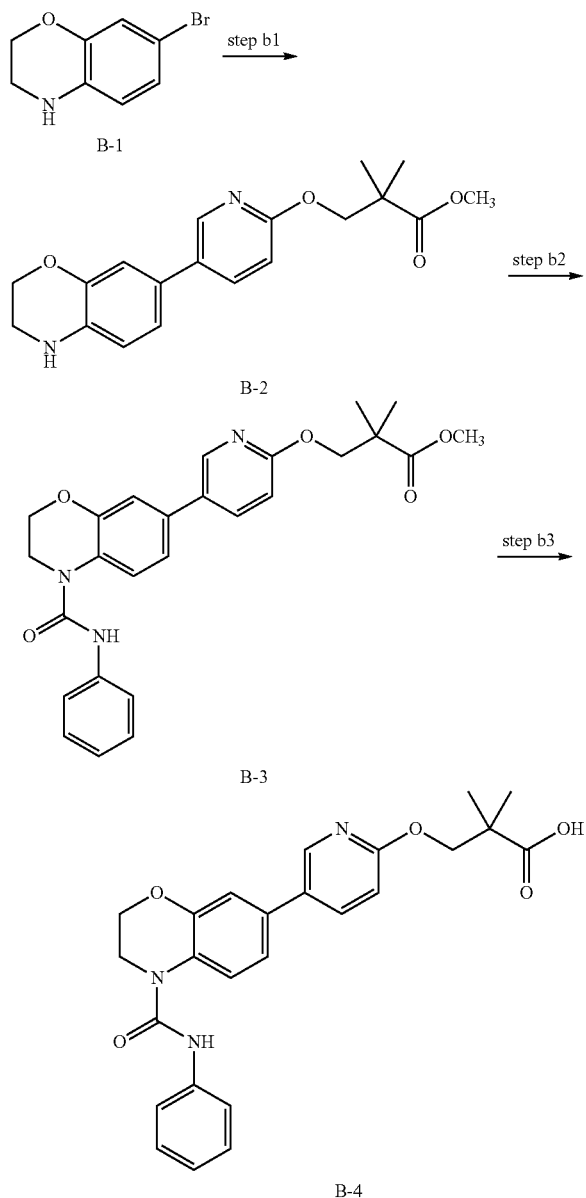

Intermediate B-2 methyl 3-(5-(3,4-dihydro-2H-benzo[b][1,4]oxazin-7-yl)pyridin-2-yloxy)-2,2-dimethylpropanoate—step b1

7-Bromo-3,4-dihydro-2H-benzo[b][1,4]oxazine B-1 (44.9 mg, 0.197 mmol), potassium trifluoro(6-(3-methoxy-2,2-dimethyl-3-oxopropoxy)pyridin-3-yl)borate A-8 (80.0 mg, 0.256 mmol), anhydrous potassium carbonate (68.3 mg, 0.492 mmol) and [1,3-bis(2,6-diisopropylphenyl)imidazol-2-ylidene](3-chloropyridyl)palladium(II) dichloride (PEPPSI-iPr, 13.6 mg, 0.020 mmol) were mixed in 1:1 ethanol:water (1.97 mL) in a 5 mL microwave reactor vial, evacuated several times and placed under an argon atmosphere. The reaction mixture was sealed, heated at 70° C. for 45 mins under microwave irradiation, then cooled to room temperature and concentrated to dryness under reduced pressure. The crude residue was purified by flash column chromatography on silica gel (hexanes:ethyl acetate gradient) to give methyl 3-(5-(3,4-dihydro-2H-benzo[b][1,4]oxazin-7-yl)pyridin-2-yloxy)-2,2-dimethylpropanoate B-2 (39.2 mg, Yield=58%). MS (ESI) [M+1]$^+$ 343.

Intermediate B-3 methyl 2,2-dimethyl-3-(5-(4-(phenylcarbamoyl)-3,4-dihydro-2H-benzo[b][1,4]oxazin-7-yl)pyridin-2-yloxy)propanoate—step b2

Phenyl isocyanate (16.1 μL, 0.148 mmol) was added at room temperature to a solution of methyl 3-(5-(3,4-dihydro-2H-benzo[b][1,4]oxazin-7-yl)pyridin-2-yloxy)-2,2-dimethylpropanoate B-2 (39.2 mg, 0.114 mmol) in anhydrous methylene chloride (0.57 mL) under an atmosphere of argon. The reaction mixture was stirred overnight, then concentrated to dryness under reduced pressure to give crude methyl 2,2-dimethyl-3-(5-(4-(phenylcarbamoyl)-3,4-dihydro-2H-benzo[b][1,4]oxazin-7-yl)pyridin-2-yloxy)propanoate B-3 (62.0 mg), which was sufficiently pure to be used for the next step without additional purification. MS (ESI), [M+1]$^+$ 462.

Example B-4

2,2-dimethyl-3-(5-(4-(phenylcarbamoyl)-3,4-dihydro-2H-benzo[b][1,4]oxazin-7-yl)pyridin-2-yloxy)propanoic acid—step b3

Lithium hydroxide monohydrate (14.3 mg, 0.342 mmol) was added to a solution of methyl 2,2-dimethyl-3-(5-(4-(phenylcarbamoyl)-3,4-dihydro-2H-benzo[b][1,4]oxazin-7-yl)pyridin-2-yloxy)propanoate B-3 (ca. 62.0 mg, 0.114 mmol) in 1:1:1 tetrahydrofuran:water:methanol (1.14 mL) at room temperature. After 12 h of vigorous stirring at room temperature, lithium hydroxide monohydrate (14.3 mg, 0.342 mmol) was added, and the reaction mixture was heated at 65° C. under microwave irradiation for 30 mins. The clear solution was then quenched with a 1 N aqueous solution of hydrogen chloride (1.0 mL) and concentrated to dryness under reduced pressure. The crude residue was purified by flash column chromatography on C$_{18}$ reverse phase (water:acetonitrile gradient with 0.05% formic acid) to give white crystalline 2,2-dimethyl-3-(5-(4-(phenylcarbamoyl)-3,4-dihydro-2H-benzo[b][1,4]oxazin-7-yl)pyridin-2-yloxy)propanoic acid B-4 (36.6 mg, Yield=72% over 2 steps). $^1$H NMR (500 MHz, DMSO-d$_6$) δ ppm 1.23 (s, 6H), 3.88 (t, J=4.10 Hz, 2H), 4.28 (s, 2H), 4.30 (t, J=4.10 Hz, 2H), 6.86 (d, J=8.51 Hz, 1H), 7.01

(dt, J=1.10, 7.41 Hz, 1H), 7.16-7.21 (m, 2H), 7.29 (t, J=7.72 Hz, 2H), 7.50 (d, J=8.20 Hz, 2H), 7.60 (d, J=8.51 Hz, 1H), 7.98 (br d, J=8.51 Hz, 1H), 8.44 (s, 1H), 9.16 (s, 1H), 12.37 (br s, 1H); MS (ESI) [M+1]$^+$ 448.

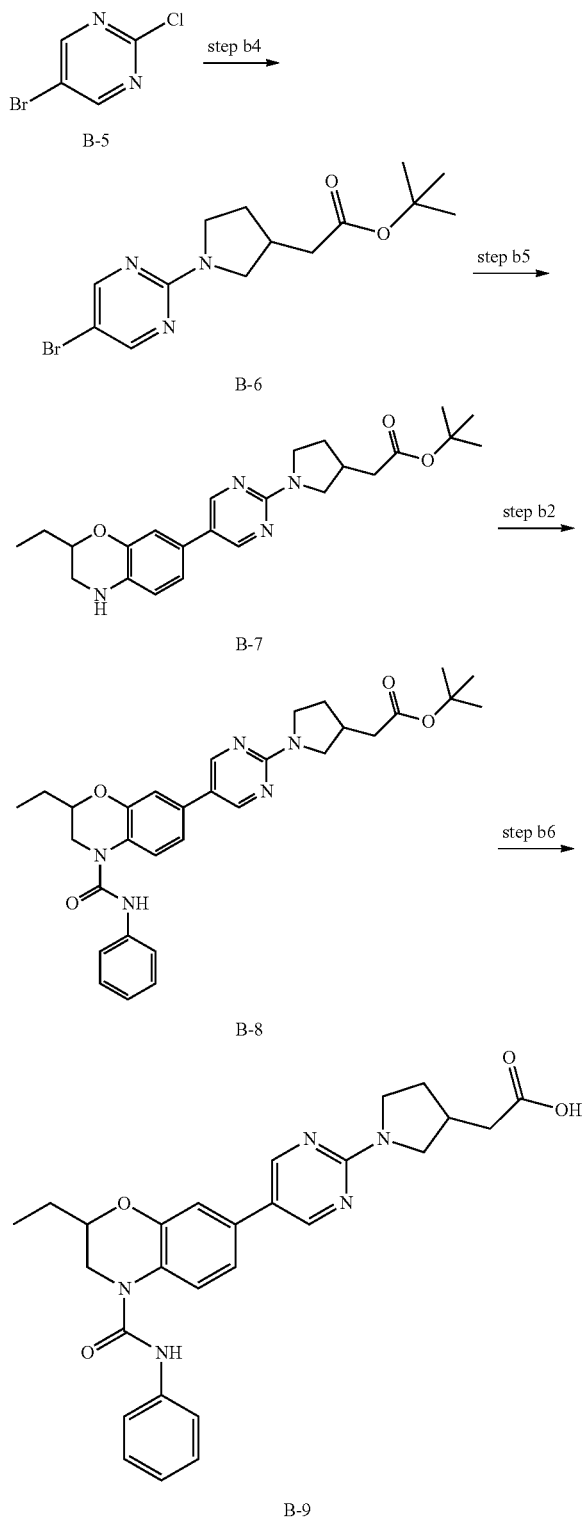

Intermediate B-6 tert-butyl 2-(1-(5-bromopyrimidin-2-yl)pyrrolidin-3-yl)acetate—step b4

N-Ethyl-N,N-diisopropylamine (1.80 mL, 10.34 mmol) was added dropwise at room temperature to a solution of 5-bromo-2-chloropyrimidine B-5 (1.00 g, 5.17 mmol) and tert-butyl 2-(pyrrolidin-3-yl)acetate (1.00 g, 5.40 mmol) in anhydrous α,α,α-trifluorotoluene (10.2 mL) under an argon atmosphere, in a 20 mL microwave reactor vial. The reaction mixture was sealed and heated at 120° C. for 30 mins under microwave irradiation, then successively cooled to room temperature, diluted with methylene chloride (100 mL), quenched with a 1 N aqueous solution of hydrogen chloride (30 mL) and decanted. The aqueous layer was extracted with methylene chloride (2×150 mL); the combined extracts were sequentially washed with brine (100 mL), dried over anhydrous magnesium sulfate, filtered and concentrated to dryness under reduced pressure. The crude residue was purified by flash column chromatography on silica gel (hexanes to ethyl acetate gradient) to give tert-butyl 2-(1-(5-bromopyrimidin-2-yl)pyrrolidin-3-yl)acetate B-6 (1.22 g, Yield=69%). MS (ESI), [M+1]$^+$ 342, 344.

Intermediate B-7 tert-butyl 2-(1-(5-(2-ethyl-3,4-dihydro-2H-benzo[b][1,4]oxazin-7-yl)pyrimidin-2-yl)pyrrolidin-3-yl)acetate—step b5

[1,1'-Bis(diphenylphosphino)ferrocene]dichloropalladium(II) complex with dichloromethane (1:1) (20.4 mg, 0.025 mmol), potassium carbonate (174.7 mg, 1.258 mmol), 2-ethyl-7-(4,4,5,5-tetramethyl-1,3,2-dioxaborolan-2-yl)-3,4-dihydro-2H-benzo[b][1,4]oxazine (prepared according to the procedure indicated in Scheme A1, 160.0 mg, 0.553 mmol) and tert-butyl 2-(1-(5-bromopyrimidin-2-yl)pyrrolidin-3-yl)acetate B-6 (172.1 mg, 0.503 mmol) were mixed in a 4:1 dioxane:water mixture (5.55 mL) at room temperature. The reaction mixture was degassed several times under reduced pressure and stirred for 12 h under an atmosphere of argon. The mixture was then filtered through a celite pad, washed with ethyl acetate (30 mL) and concentrated to dryness under reduced pressure. The residue was adsorbed on silica (1.0 g) and purified by flash column chromatography on silica gel (hexanes to ethyl acetate gradient) to give tert-butyl 2-(1-(5-(2-ethyl-3,4-dihydro-2H-benzo[b][1,4]oxazin-7-yl)pyrimidin-2-yl)pyrrolidin-3-yl)acetate B-7 as a light yellow oil (140.0 mg; Yield=60%). MS (ESI) [M+1]$^+$ 425.

Intermediate B-8 tert-butyl 2-(1-(5-(2-ethyl-4-(phenylcarbamoyl)-3,4-dihydro-2H-benzo[b][1,4]oxazin-7-yl)pyrimidin-2-yl)pyrrolidin-3-yl)acetate—step b2

Intermediate B-8 was prepared by the procedure described for step b2, using tert-butyl 2-(1-(5-(2-ethyl-3,4-dihydro-2H-benzo[b][1,4]oxazin-7-yl)pyrimidin-2-yl)pyrrolidin-3-yl)acetate B-7 as starting material. MS (ESI) [M+1]$^+$ 544.

Example B-9

2-(1-(5-(2-ethyl-4-(phenylcarbamoyl)-3,4-dihydro-2H-benzo[b][1,4]oxazin-7-yl)pyrimidin-2-yl)pyrrolidin-3-yl)acetic acid—step b6

Trifluoroacetic acid (0.109 mL, 1.43 mmol) and triethylsilane (44 μL, 0.28 mmol) were successively added at room temperature to a solution of crude ted-butyl 2-(1-(5-(2-ethyl-4-(phenylcarbamoyl)-3,4-dihydro-2H-benzo[b][1,4]oxazin-7-yl)pyrimidin-2-yl)pyrrolidin-3-yl)acetate B-8 (59.0 mg, 0.11 mmol) in anhydrous methylene chloride (0.25 mL) under an atmosphere of argon. The reaction mixture was stirred at room temperature for 12 h, then concentrated to dryness under reduced pressure. The crude residue was purified by flash column chromatography on $C_{18}$ reverse phase (water:acetonitrile gradient with 0.05% formic acid) to give 2-(1-(5-(2-ethyl-4-(phenylcarbamoyl)-3,4-dihydro-2H-benzo[b][1,4]oxazin-7-yl)pyrimidin-2-yl)pyrrolidin-3-yl)acetic acid B-9 (22.3 mg, Yield=42% over 2 steps). $^1$H NMR (500 MHz, DMSO-$d_6$) δ ppm 1.01 (t, J=Hz, 3H), 1.63-1.74 (m, 3H), 2.12-2.18 (m, 1H), 2.42 (d, J=7.25 Hz, 2H), 2.52-2.64 (m, 1H), 3.15 (dd, J=7.88, 10.88 Hz, 1H), 3.46 (dd, J=7.88, 12.60 Hz, 1H), 3.48 (t, J=7.56 Hz, 1H), 3.63-3.69 (m, 1H), 3.80 (dd, J=7.41, 11.35 Hz, 1H), 4.03 (br d, J=13.08 Hz, 1H), 4.16 (q, J=6.69 Hz, 1H), 7.00 (t, J=7.41 Hz, 1H), 7.15 (br d, J=8.67 Hz, 1H), 7.18 (s, 1H), 7.29 (t, J=7.41 Hz, 2H), 7.50 (d, J=8.36 Hz, 2H), 7.51 (d, J=8.83 Hz, 1H), 8.66 (s, 2H), 9.14 (s, 1H), 12.22 (br s, 1H); MS (ESI) [M+1]$^+$ 488.

Scheme B3: Preparation of example B-13

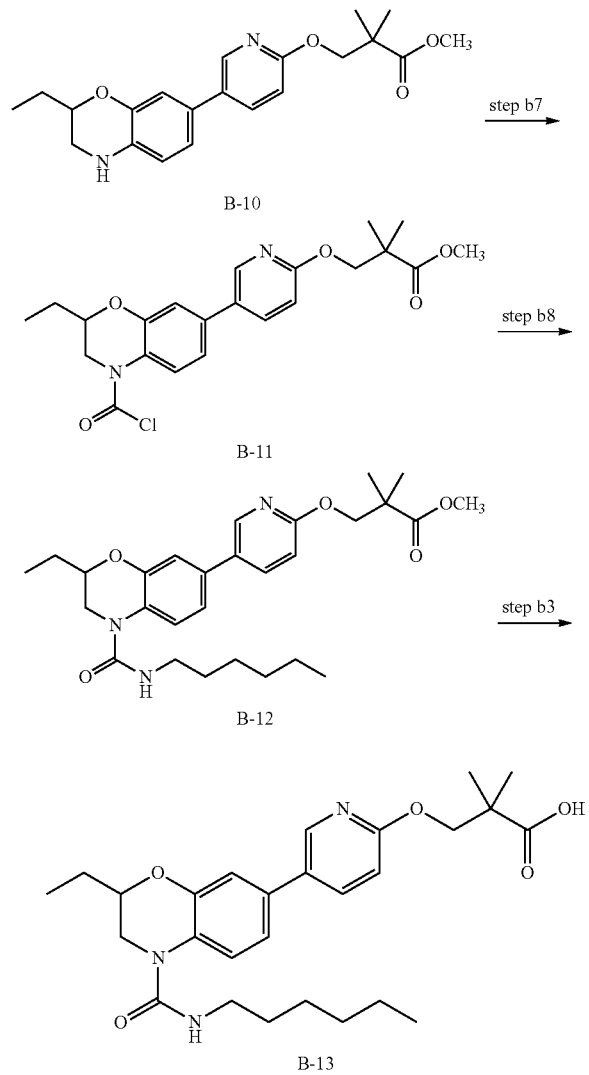

Intermediate B-11 methyl 3-(5-(4-(chlorocarbonyl)-2-ethyl-3,4-dihydro-2H-benzo[b][1,4]oxazin-7-yl)pyridin-2-yloxy)-2,2-dimethylpropanoate—step b7

A solution of methyl 3-(5-(2-ethyl-3,4-dihydro-2H-benzo[b][1,4]oxazin-7-yl)pyridin-2-yloxy)-2,2-dimethylpropanoate B-10 (248.0 mg, 0.60 mmol) and dry pyridine (97.0 μL, 1.20 mmol) in anhydrous methylene chloride (3.0 mL) was added dropwise to a solution of triphosgene (71.2 mg, 0.24 mmol) in anhydrous methylene chloride (3.0 mL) at −20° C. under an atmosphere of argon. The reaction mixture was allowed to warm to room temperature over 30 mins and was stirred for 3 h at room temperature. It was then successively diluted with methylene chloride (25 mL), quenched with a 1 N aqueous solution of hydrogen chloride (1.0 mL), diluted with water (10 mL) and decanted. The aqueous layer was extracted with methylene chloride (3×30 mL); the combined extracts were washed with a 1 N aqueous solution of hydrogen chloride (20 mL), brine (20 mL), dried over anhydrous magnesium sulfate, filtered and concentrated to dryness under reduced pressure. The light pink solid methyl 3-(5-(4-(chlorocarbonyl)-2-ethyl-3,4-dihydro-2H-benzo[b][1,4]oxazin-7-yl)pyridin-2-yloxy)-2,2-dimethylpropanoate B-11 (265.0 mg, Yield=100%) was used for the next step without purification and stored at −20° C. under an atmosphere of nitrogen. MS (ESI) [M+1]$^+$ 433.

Intermediate B-12 methyl 3-(5-(2-ethyl-4-(hexylcarbamoyl)-3,4-dihydro-2H-benzo[b][1,4]oxazin-7-yl)pyridin-2-yloxy)-2,2-dimethylpropanoate—step b8 n-Hexylamine (23.0 μL, 0.173 mmol) was added dropwise to a solution of methyl 3-(5-(4-(chlorocarbonyl)-2-ethyl-3,4-dihydro-2H-benzo[b][1,4]oxazin-7-yl)pyridin-2-yloxy)-2,2-dimethylpropanoate B-11 (50.0 mg, 0.115 mmol) and N-ethyl-N,N-diisopropylamine (40.2 μL, 0.231 mmol) in anhydrous methylene chloride (1.10 mL) at 0° C. under an atmosphere of argon. The reaction mixture was slowly warmed to room temperature and stirred for 8 h, then sequentially diluted with methylene chloride (30 mL), quenched with an aqueous pH 7 phosphate buffer solution (15 mL) and decanted. The aqueous layer was extracted with methylene chloride (3×30 mL); the combined extracts were successively washed with an aqueous pH 7 phosphate buffer solution (20 mL), brine (20 mL), dried over anhydrous magnesium sulfate, filtered and concentrated to dryness under reduced pressure. Crude methyl 3-(5-(2-ethyl-4-(hexylcarbamoyl)-3,4-dihydro-2H-benzo[b][1,4]oxazin-7-yl)pyridin-2-yloxy)-2,2-dimethylpropanoate B-12 (55.2 mg, Yield=96%) was obtained as a light tan solid and was used for the next step without further purification. MS (ESI) [M+1]$^+$ 498.

Example B-13

3-(5-(2-ethyl-4-(hexylcarbamoyl)-3,4-dihydro-2H-benzo[b][1,4]oxazin-7-yl)pyridin-2-yloxy)-2,2-dimethylpropanoic acid—step b3

Example B-13 was prepared by the procedure described for step b3, using methyl 3-(5-(2-ethyl-4-(hexylcarbamoyl)-3,4-dihydro-2H-benzo[b][1,4]oxazin-7-yl)pyridin-2-yloxy)-2,2-dimethylpropanoate B-12 as starting material. $^1$H NMR (500 MHz, DMSO-$d_6$) δ ppm 0.88 (t, J=6.78 Hz, 3H), 1.00 (t, J=7.41 Hz, 3H), 1.22 (s, 6H), 1.25-1.32 (m, 6H), 1.44-1.50 (m, 2H), 1.57-1.69 (m, 2H), 3.07-3.14 (m, 2H), 3.31 (dd, J=7.41, 13.57 Hz, 1H), 3.93 (br d, J=13.24 Hz, 1H), 4.00-4.06 (m, 1H), 4.28 (s, 2H), 6.85 (d, J=8.51 Hz, 1H), 6.97 (t, J=4.89 Hz, 1H), 7.12-7.16 (m, 2H), 7.59 (d, J=8.83 Hz, 1H), 7.97 (dd, J=1.89, 8.51 Hz, 1H), 8.20 (s, 1H), 12.35 (br s, 1H); MS (ESI) [M+1]⁺ 484.

Scheme B4: Preparation of example B-16 and B-17

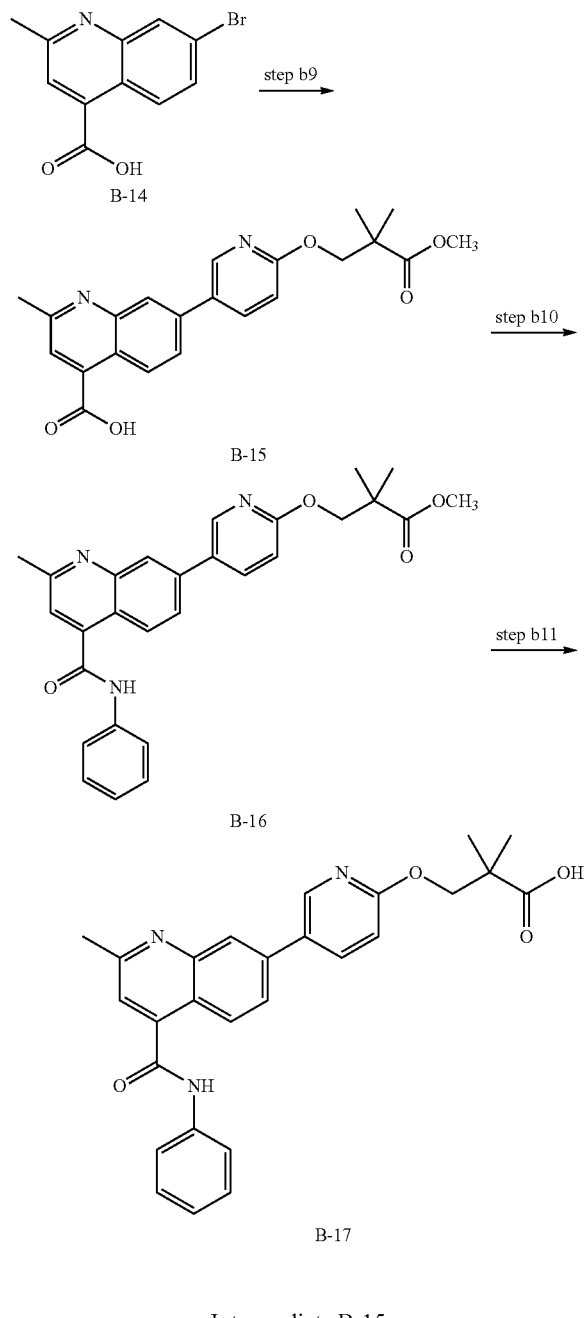

Intermediate B-15

7-(6-(3-methoxy-2,2-dimethyl-3-oxopropoxy)pyridin-3-yl)-2-methylquinoline-4-carboxylic acid—step b9

[1,1'-Bis(diphenylphosphino)ferrocene]dichloropalladium(II) complex with dichloromethane (1:1) (40.8 mg, 0.05 mmol) and an aqueous solution of potassium carbonate (0.72 g, 4 mmol in 1.0 mL of water) were successively added to a solution of 7-bromo-2-methylquinoline-4-carboxylic acid B-14 (0.26 g, 1.00 mmol) and methyl 2,2-dimethyl-3-(5-(4,4,5,5-tetramethyl-1,3,2-dioxaborolan-2-yl)pyridin-2-yloxy)propanoate A-7 (0.43 g, 1.50 mmol) in isopropanol (5.0 mL) and 1,4-dioxane (20 mL). The reaction was degassed several times under reduced pressure, placed under a nitrogen atmosphere and stirred at room temperature for 24 h. After quenching with a 1 N aqueous hydrogen chloride solution (2.0 mL), the mixture was filtered through a celite pad, washed with ethyl acetate (100 mL) and concentrated to dryness under reduced pressure. The residue was purified by flash column chromatography on silica gel (20:1 CH₂Cl₂:MeOH) to give 7-(6-(3-methoxy-2,2-dimethyl-3-oxopropoxy)pyridin-3-yl)-2-methylquinoline-4-carboxylic acid B-15 as a brown solid (0.32 g, Yield=82%). MS (ESI), [M+1]⁺ 395.

Example B-16 methyl 2,2-dimethyl-3-(5-(2-methyl-4-(phenylcarbamoyl)quinolin-7-yl)pyridin-2-yloxy)propanoate—step b10

N-Ethyl-N,N-diisopropylamine (64.5 mg, 0.50 mmol) was added at room temperature to a solution of aniline (465.0 mg, 0.50 mmol), 7-(6-(3-methoxy-2,2-dimethyl-3-oxopropoxy)pyridin-3-yl)-2-methylquinoline-4-carboxylic acid B-15 (98.8 mg, 0.25 mmol) and N,N,N'N-tetramethyl-O-(7-azabenzotriazol-1-yl)uronium hexafluorophosphate (190.0 mg, 0.50 mmol) in anhydrous N,N-dimethylformamide (5.0 mL) under an atmosphere of nitrogen. The reaction mixture was stirred overnight, then partitioned between methylene chloride (30 mL) and an aqueous solution of pH 7 phosphate buffer (30 mL). The aqueous layer was extracted with methylene chloride (3×30 mL); the combined extracts were successively washed with water (30 mL), brine (30 mL), then dried over anhydrous magnesium sulfate, filtered and concentrated to dryness under reduced pressure. The crude residue was purified by flash column chromatography on silica gel (hexanes:ethyl acetate gradient) to give methyl 2,2-dimethyl-3-(5-(2-methyl-4-(phenylcarbamoyl)quinolin-7-yl)pyridin-2-yloxy)propanoate B-16 (103.4 mg, Yield=88%). ¹H NMR (500 MHz, CHLOROFORM-d) δ ppm 1.37 (s, 6H), 2.83 (s, 3H), 3.73 (s, 3H), 4.42 (s, 2H), 6.90 (d, J=8.5 Hz, 1H), 7.26-7.29 (m, 1H), 7.45-7.48 (m, 3H), 7.73-7.77 (m, 2H), 7.88 (s, 1H), 7.95 (q, J=6.0 Hz, 1H), 8.23 (s, 1H), 8.32 (d, J=8.5 Hz, 1H), 8.54 (s, 1H); MS (ESI) [M+1]⁺ 470.

Example B-17

2,2-dimethyl-3-(5-(2-methyl-4-(phenylcarbamoyl)quinolin-7-yl)pyridin-2-yloxy)propanoic acid—step b11

A 1 N aqueous solution of sodium hydroxide (2.0 mL) was added to a solution of methyl 2,2-dimethyl-3-(5-(2-methyl-4-(phenylcarbamoyl)quinolin-7-yl)pyridin-2-yloxy)propanoate B-16 (94.0 mg, 0.20 mmol) in a 1:1 mixture of tetrahydrofuran:methanol (5.0 mL) at room temperature. After 12 h of stirring, the aqueous layer was acidified to pH 0 with a 1 N aqueous hydrogen chloride solution and concentrated to dryness under reduced pressure. The crude residue was purified by flash column chromatography on $C_{18}$ reverse phase (water:acetonitrile gradient with 0.05% formic acid) to give 2,2-dimethyl-3-(5-(2-methyl-4-(phenylcarbamoyl)quinolin-7-yl)pyridin-2-yloxy)propanoic acid B-17 (54.7 mg, Yield=60%). $^1$H NMR (500 MHz, DMSO-$d_6$) δ ppm 1.17 (s, 6H), 2.75 (s, 3H), 4.30 (s, 2H), 6.93 (d, J=8.5 Hz, 1H), 7.19 (t, J=7.5 Hz, 1H), 7.41 (t, J=9.5 Hz, 1H), 7.64 (s, 1H), 7.81 (d, J=8.0 Hz, 1H), 7.97 (d, J=9.0 Hz, 1H), 8.16 (d, J=8.5 Hz, 1H), 8.21 (d, J=8.5 Hz, 1H), 8.29 (s, 1H), 8.51 (s, 2H), 8.67 (m, 1H), 10.86 (s, 1H); MS (ESI) [M+1]$^+$ 456.

Scheme B5: Preparation of example B-22

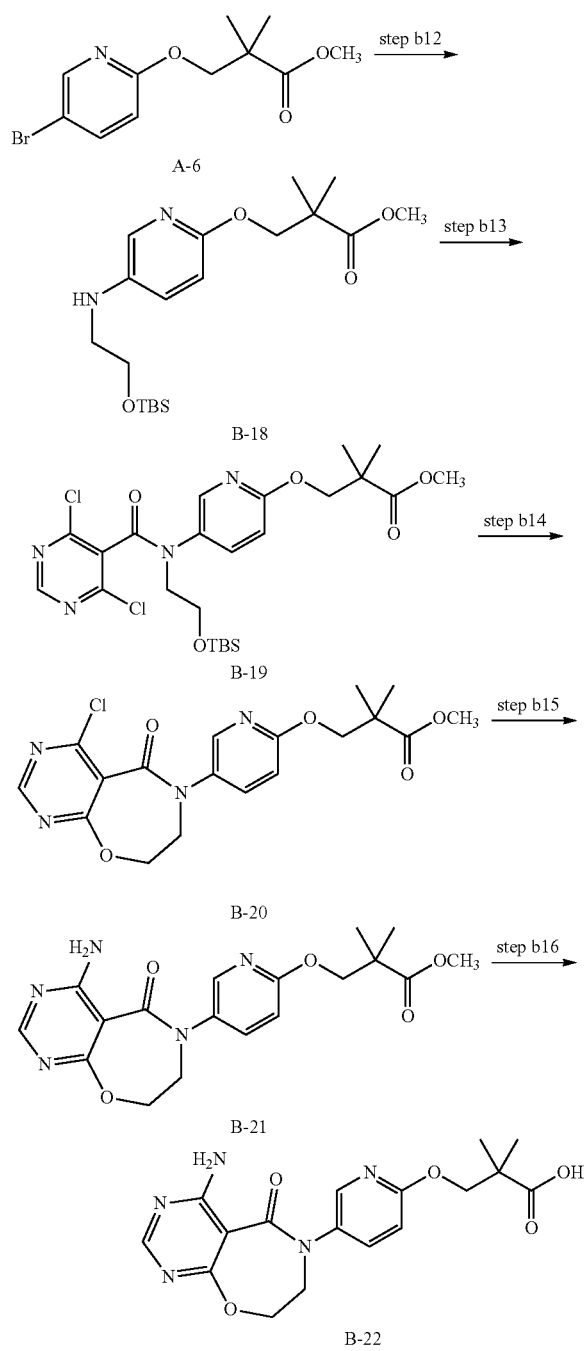

Intermediate B-18 methyl 3-(5-(2-(tert-butyldimethylsilyloxy)ethylamino)pyridin-2-yloxy)-2,2-dimethylpropanoate—step b12

Methyl 3-(5-bromopyridin-2-yloxy)-2,2-dimethylpropanoate A-6 (576.3 mg, 2.00 mmol), 2-(tert-butyldimethylsilyloxy)ethanamine (420.8 mg, 2.40 mmol), palladium (II) acetate (44.8 mg, 0.20 mmol), X-phos (95.4 mg, 0.20 mmol) and potassium tert-butoxide (313.6 mg, 2.80 mmol) were mixed in anhydrous toluene (10.0 mL) at room temperature. The reaction mixture was degassed several times, heated at 90° C. for 20 h under an atmosphere of nitrogen, then cooled to room temperature and concentrated to dryness under reduced pressure. The crude residue was purified by flash column chromatography on silica gel (hexanes:ethyl acetate gradient) to give methyl 3-(5-(2-(tert-butyldimethylsilyloxy)ethylamino)pyridin-2-yloxy)-2,2-dimethylpropanoate B-18 (67.0 mg, Yield=9%). MS (ESI) [M+1]$^+$ 383.

Intermediate B-19 methyl 3-(5-(N-(2-(tert-butyldimethylsilyloxy)ethyl)-4,6-dichloropyrimidine-5-carboxamido)pyridin-2-yloxy)-2,2-dimethylpropanoate—step b13

A solution of 4,6-dichloropyrimidine-5-carbonyl chloride (130.5 mg, 0.617 mmol) in anhydrous tetrahydrofuran (1.5 mL) was added dropwise to a solution of methyl 3-(5-(2-(tert-butyldimethylsilyloxy)ethylamino)pyridin-2-yloxy)-2,2-dimethylpropanoate B-18 (157.2 mg, 0.411 mmol) and triethylamine (124.5 mg, 1.233 mmol) in anhydrous tetrahydrofuran (5.0 mL) at 0° C. The reaction mixture was stirred for 30 mins, then allowed to warm to room temperature, stirred for an additional 2 h period and then concentrated to dryness under reduced pressure. The crude residue was purified by flash column chromatography on silica gel (hexanes:ethyl acetate gradient) to give methyl 3-(5-(N-(2-(tert-butyldimethylsilyloxy)ethyl)-4,6-dichloropyrimidine-5-carboxamido)pyridin-2-yloxy)-2,2-dimethylpropanoate B-19 (150 mg, Yield=66%). MS (ESI) [M+1]$^+$ 558.

Intermediate B-20 methyl 3-(5-(4-chloro-5-oxo-7,8-dihydropyrimido[5,4-f][1,4]oxazepin-6(5H)-yl)pyridin-2-yloxy)-2,2-dimethylpropanoate—step b14

A concentrated aqueous solution of hydrogen chloride (34-37.5%, 0.1 mL) was added at room temperature to a solution of methyl 3-(5-(N-(2-(tert-butyldimethylsilyloxy)ethyl)-4,6-dichloropyrimidine-5-carboxamido)pyridin-2-yloxy)-2,2-dimethylpropanoate B-19 (139.4 mg, 0.25 mmol) in methanol (2.0 mL). The reaction mixture was stirred for 30 mins at room temperature and concentrated to dryness under reduced pressure. The residue was dissolved in ethyl acetate, successively washed with a saturated aqueous solution of sodium bicarbonate and brine, dried over anhydrous sodium sulfate, filtered and concentrated to dryness under reduced pressure to give crude intermediate methyl 3-(5-(4,6-dichloro-N-(2-hydroxyethyl)pyrimidine-5-carboxamido)pyridin-2-yloxy)-2,2-dimethylpropanoate (MS (ESI) [M+1]$^+$ 444), which was then dissolved in acetonitrile (2.0 mL). Triethylamine (0.14 mL, 1.0 mmol) was then added at room temperature, and the reaction mixture was heated at 100° C. for 3 h then concentrated to dryness under reduced pressure. The residue was dissolved in ethyl acetate, successively washed with water and brine, dried over anhydrous sodium sulfate, filtered and concentrated to dryness under reduced pressure to give methyl 3-(5-(4-chloro-5-oxo-7,8-dihydropyrimido[5,4-f][1,4]oxazepin-6(5H)-yl)pyridin-2-yloxy)-2,2-dimethylpropanoate B-20. This material was used for the next step without purification. MS (ESI) [M+1]⁺ 407.

Intermediate B-21 methyl 3-(5-(4-amino-5-oxo-7,8-dihydropyrimido[5,4-f][1,4]oxazepin-6(5H)-yl)pyridin-2-yloxy)-2,2-dimethylpropanoate—step b15

Methyl 3-(5-(4-chloro-5-oxo-7,8-dihydropyrimido[5,4-f][1,4]oxazepin-6(5H)-yl)pyridin-2-yloxy)-2,2-dimethylpropanoate B-20 was dissolved in a 0.5 M solution of ammonia in 1,4-dioxane and stirred at room temperature for 20 h. The reaction mixture was then concentrated to dryness under reduced pressure. The residue was purified by flash column chromatography on silica gel (7 N ammonia solution in methanol:CH$_2$Cl$_2$ gradient) to give methyl 3-(5-(4-amino-5-oxo-7,8-dihydropyrimido[5,4-f][1,4]oxazepin-6(5H)-yl)pyridin-2-yloxy)-2,2-dimethylpropanoate B-21 (55.0 mg, Yield=57% from B-19). MS (ESI) [M+1]⁺ 388.

Example B-22

3-(5-(4-amino-5-oxo-7,8-dihydropyrimido[5,4-f][1,4]oxazepin-6(5H)-yl)pyridin-2-yloxy)-2,2-dimethylpropanoic acid—step b16

Lithium hydroxide monohydrate (16.4 mg, 0.39 mmol) was added at room temperature to a solution of methyl 3-(5-(4-amino-5-oxo-7,8-dihydropyrimido[5,4-f][1,4]oxazepin-6(5H)-yl)pyridin-2-yloxy)-2,2-dimethylpropanoate B-21 (50.4 mg, 0.13 mmol) in 1,4-dioxane (2.0 mL) and water (1.0 mL). The reaction mixture was heated at 60° C. for 2 h and then concentrated to dryness under reduced pressure. The residue was purified by flash column chromatography on C$_{18}$ reverse phase (water:acetonitrile gradient with 0.05% formic acid) to give 3-(5-(4-amino-5-oxo-7,8-dihydropyrimido[5,4-f][1,4]oxazepin-6(5H)-yl)pyridin-2-yloxy)-2,2-dimethylpropanoic acid B-22 (27.0 mg, Yield=56%). ¹H NMR (500 MHz, METHANOL-d$_4$) δ ppm 1.33 (s, 6H), 4.13 (m, 2H), 4.35 (s, 2H), 4.85 (m, 2H), 6.90 (d, J=8.83 Hz, 1H), 7.71 (d, J=8.83 Hz, 1H), 8.16 (s, 1H), 8.29 (s, 1H); MS (ESI) [M+1]⁺ 374.

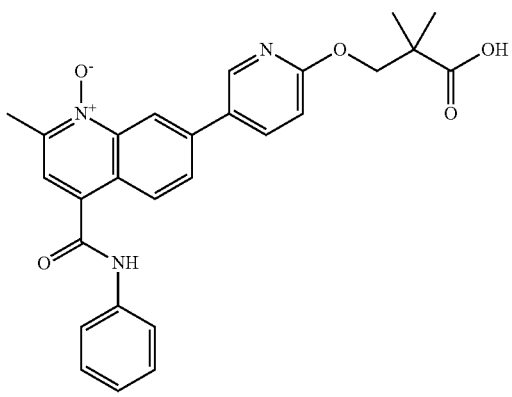

B-23

Example B-23

7-(6-(2-carboxy-2-methylpropoxy)pyridin-3-yl)-2-methyl-4-(phenylcarbamoyl)quinoline 1-oxide—step b17 m-Chloroperoxybenzoic acid (30.0 mg, 0.20 mmol) was added at room temperature to a solution of 2,2-dimethyl-3-(5-(2-methyl-4-(phenylcarbamoyl)quinolin-7-yl)pyridin-2-yloxy)propanoic acid B-17 (45.5 mg, 0.10 mmol) in methylene chloride (7 mL). The reaction mixture was stirred at room temperature overnight, then concentrated to dryness under reduced pressure. The residue was purified by flash column chromatography on C$_{18}$ reverse phase (water:acetonitrile gradient with 0.05% formic acid) to give 7-(6-(2-carboxy-2-methylpropoxy)pyridin-3-yl)-2-methyl-4-(phenylcarbamoyl)quinoline 1-oxide B-23 (16.0 mg, Yield=40%). ¹H NMR (500 MHz, DMSO-d$_6$) δ ppm 1.28 (s, 6H), 2.66 (s, 3H), 4.34 (s, 2H), 7.17 (d, J=6.0 Hz, 1H), 7.40-7.46 (m, 3H), 7.80 (d, J=8.0 Hz, 2H), 7.93 (d, J=8.5 Hz, 1H), 7.99 (s, 1H), 8.14 (d, J=8.5 Hz, 1H), 8.41 (d, J=8.5 Hz, 1H), 8.83 (s, 1H), 8.87 (s, 1H), 10.78 (s, 1H). MS (ESI) [M+1]⁺ 474.

Scheme B6: Preparation of example B-23

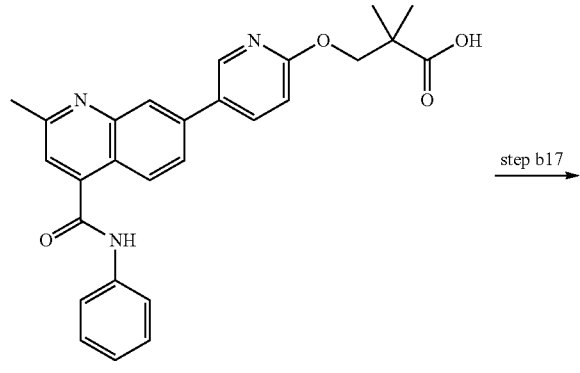

B-17 step b17
→

Scheme B7: Preparation of example B-24

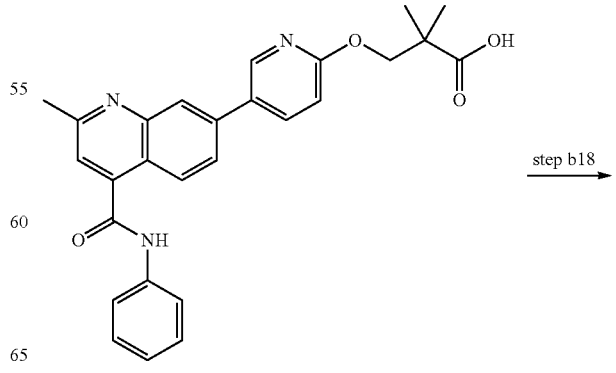

B-17 step b18
→

-continued

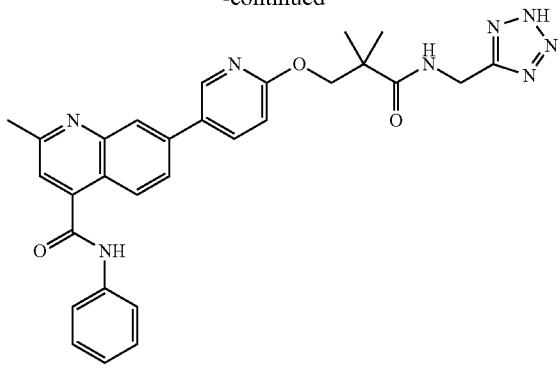

B-24

Example B-24

7-(6-(3-((2H-tetrazol-5-yl)methylamino)-2,2-dimethyl-3-oxopropoxy)pyridin-3-yl)-2-methyl-N-phenylquinoline-4-carboxamide—step b18

N-Ethyl-N,N-diisopropylamine (50.0 µL, 0.300 mmol) was added at room temperature to a solution of 2,2-dimethyl-3-(5-(2-methyl-4-(phenylcarbamoyl)quinolin-7-yl)pyridin-2-yloxy)propanoic acid B-17 (45.5 mg, 0.10 mmol), (2H-tetrazol-5-yl)methanamine hydrobromide (27.7 mg, 0.154 mmol) and (benzotriazol-1-yloxy)tripyrrolidinophosphonium hexafluorophosphate (64.0 mg, 0.123 mmol) in anhydrous N,N-dimethylformamide (5.0 mL) under an atmosphere of nitrogen. The reaction mixture was stirred overnight, then partitioned between methylene chloride (30 mL) and an aqueous solution of pH 7 phosphate buffer (30 mL). The aqueous layer was extracted with methylene chloride (3×30 mL); the combined extracts were successively washed with water (30 mL), brine (30 mL), then dried over anhydrous magnesium sulfate, filtered and concentrated to dryness under reduced pressure. The crude residue was purified by flash column chromatography on silica gel (hexanes:ethyl acetate gradient) to give 7-(6-(3-((2H-tetrazol-5-yl)methylamino)-2,2-dimethyl-3-oxopropoxy)pyridin-3-yl)-2-methyl-N-phenylquinoline-4-carboxamide B-24 (34.9 mg, Yield=65%). $^1$H NMR (500 MHz, CHLOROFORM-d) δ ppm 1.35 (s, 6H), 2.77 (s, 3H), 3.71-3.74 (m, 2H), 4.75 (d, J=5.5 Hz, 2H), 6.86 (d, J=8.5 Hz, 1H), 7.23-7.30 (m, 2H), 7.45 (t, J=6.5 Hz, 3H), 7.87 (d, J=8.0 Hz, 2H), 7.87 (d, J=8.5 Hz, 1H), 8.24 (d, J=8.5 Hz, 1H), 8.47 (s, 1H), 8.45 (d, J=9.5 Hz, 1H), 8.59 (s, 1H); MS (ESI) [M+1]$^+$ 537.

Section C

Example Compounds

Preparation of Examples C-1 to C-93

The following examples were prepared using the general procedures outlined in section B, using reagents from commercial sources or intermediates either prepared with procedures outlined in section A or section B or published literature procedures.

Example C-1

2,2-dimethyl-3-(5-(2-methyl-4-(phenylcarbamoyl)-3,4-dihydro-2H-benzo[b][1,4]oxazin-7-yl)pyridin-2-yloxy)propanoic acid

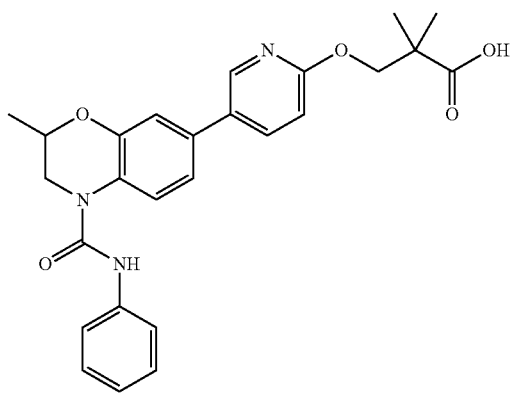 [SMILES: CC1CN(C(=O)Nc2ccccc2)c2ccc(-c3ccc(OCC(C)(C)C(=O)O)nc3)cc2O1]

$^1$H NMR (500 MHz, DMSO-d$_6$) δ ppm 1.22 (s, 6H), 1.36 (d, J=5.99 Hz, 3H), 4.10 (d, J=11.98 Hz, 1H), 4.27-4.28 (m, 1H), 4.28 (s, 2H), 4.36 (br t, J=7.09 Hz, 1H), 6.86 (d, J=8.51 Hz, 1H), 7.01 (t, J=7.25 Hz, 1H), 7.16-7.20 (m, 2H), 7.29 (t, J=7.72 Hz, 2H), 7.50 (d, J=8.20 Hz, 2H), 7.57 (d, J=8.20 Hz, 1H), 7.98 (dd, J=8.35, 1.73 Hz, 1H), 8.44 (d, J=2.30 Hz, 1H), 9.18 (s, 1H), 12.37 (br s, 1H); MS (ESI) [M+1]$^+$ 462. The R enantiomer obtained by enantioselective synthesis was characterized by chiral HPLC (isocratic mode, 1 mL/min on Varian system 1; 90:10 hexanes:isopropanol): rt=27.19 min.

Example C-2

2,2-dimethyl-3-(5-(1-(phenylcarbamoyl)indolin-5-yl)pyridin-2-yloxy)propanoic acid

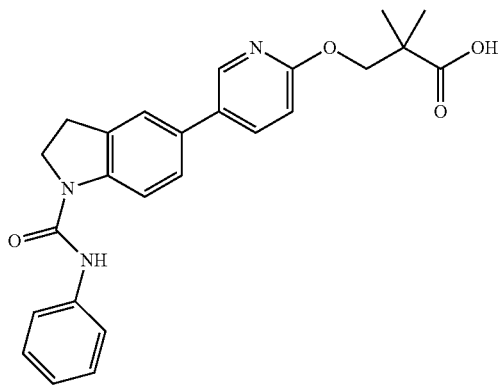 [SMILES: CC(C)(COc1ccc(-c2ccc3c(c2)CCN3C(=O)Nc2ccccc2)cn1)C(=O)O]

$^1$H NMR (500 MHz, DMSO-d$_6$) δ ppm 1.22 (s, 6H), 3.24 (t, J=8.51 Hz, 2H), 4.18 (t, J=8.51 Hz, 2H), 4.28 (s, 2H), 6.86 (d, J=8.83 Hz, 1H), 7.03 (t, J=7.25 Hz, 1H), 7.31 (t, J=7.88 Hz, 2H), 7.44 (d, J=8.51 Hz, 1H), 7.51 (s, 1H), 7.58 (d, J=8.51 Hz, 2H), 7.93 (d, J=8.51 Hz, 1H), 7.96 (dd, J=2.68, 8.67 Hz, 1H), 8.42 (d, J=2.52 Hz, 1H), 8.56 (s, 1H), 12.49 (br s, 1H); MS (ESI) [M+1]$^+$ 432.

Example C-3

3-(5-(2-ethyl-4-(phenylcarbamoyl)-3,4-dihydro-2H-benzo[b][1,4]oxazin-7-yl)pyridin-2-yloxy)-2,2-dimethylpropanoic acid

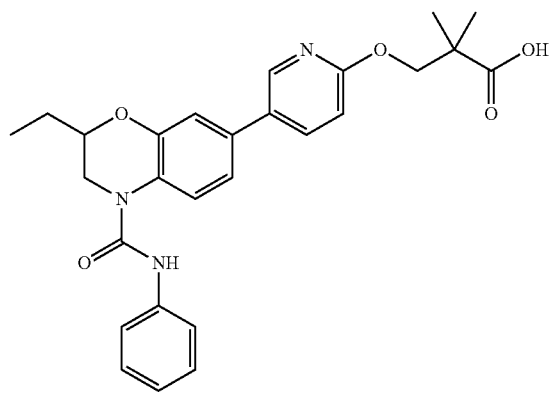 [SMILES: CCC1CN(C(=O)Nc2ccccc2)c2ccc(-c3ccc(OCC(C)(C)C(=O)O)nc3)cc2O1]

$^1$H NMR (500 MHz, DMSO-d$_6$) δ ppm 1.02 (t, J=7.41 Hz, 3H), 1.23 (s, 6H), 1.57-1.78 (m, 2H), 3.47 (dd, J=7.26, 13.30 Hz, 1H), 4.04 (dd, J=2.05, 13.30 Hz, 1H), 4.17 (br q, J=7.26 Hz, 1H), 4.28 (s, 2H), 6.86 (d, J=8.83 Hz, 1H), 7.01 (t, J=7.41 Hz, 1H), 7.18 (d, J=8.67 Hz, 1H), 7.20 (s, 1H), 7.29 (t, J=7.88 Hz, 2H), 7.50 (d, J=8.20 Hz, 2H), 7.55 (d, J=8.20 Hz, 1H), 7.99 (dd, J=2.68, 8.67 Hz, 1H), 8.45 (d, J=2.21 Hz, 1H), 9.17 (s, 1H), 12.37 (br s, 1H); MS (ESI) [M+1]$^+$ 476.

Example C-4

3-(5-(4-(2,4-dimethylphenylcarbamoyl)-2-ethyl-3,4-dihydro-2H-benzo[b][1,4]oxazin-7-yl)pyridin-2-yloxy)-2,2-dimethylpropanoic acid

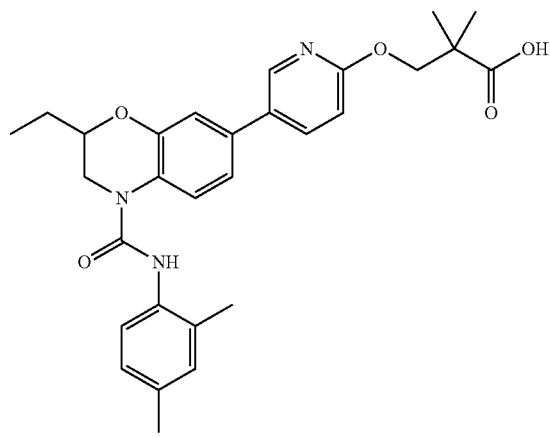 [SMILES: CCC1CN(C(=O)Nc2ccc(C)cc2C)c2ccc(-c3ccc(OCC(C)(C)C(=O)O)nc3)cc2O1]

$^1$H NMR (500 MHz, DMSO-d$_6$) δ ppm 1.04 (t, J=7.41 Hz, 3H), 1.23 (s, 6H), 1.63-1.77 (md, 2H), 2.18 (s, 3H), 2.26 (s, 3H), 3.49 (dd, J=7.25, 13.71 Hz, 1H), 4.05 (br d, J=13.40 Hz, 1H), 4.11-4.22 (m, 1H), 4.28 (s, 2H), 6.85 (d, J=8.51 Hz, 1H), 6.97 (d, J=8.20 Hz, 1H), 7.03 (s, 1H), 7.15-7.20 (m, 3H), 7.68 (m, J=8.51 Hz, 1H), 7.98 (dd, J=8.51, 1.89 Hz, 1H), 8.44 (d, J=2.21 Hz, 1H), 8.56 (s, 1H), 12.37 (br s, 1H); MS (ESI) [M+1]$^+$ 504.

Example C-5

3-(5-(4-(4-chloro-2-fluorophenylcarbamoyl)-2-ethyl-3,4-dihydro-2H-benzo[b][1,4]oxazin-7-yl)pyridin-2-yloxy)-2,2-dimethylpropanoic acid

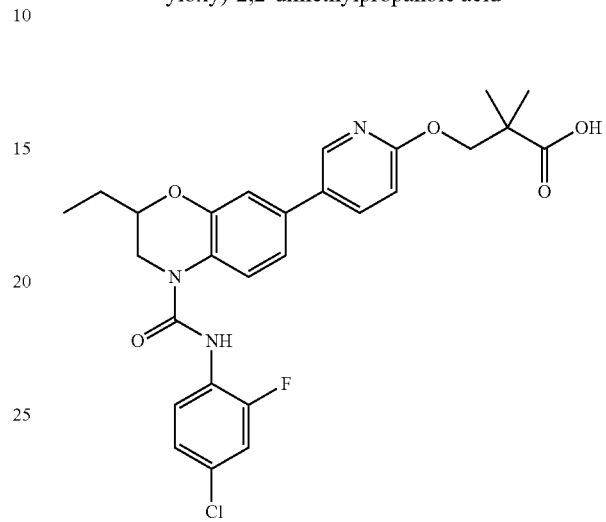

$^1$H NMR (500 MHz, DMSO-d$_6$) δ ppm 1.03 (t, J=7.41 Hz, 3H), 1.22 (s, 6H), 1.59-1.78 (m, 2H), 3.49 (dd, J=7.56, 13.56 Hz, 1H), 4.06 (br d, J=13.40 Hz, 1H), 4.13-4.23 (m, 1H), 4.28 (s, 2H), 6.86 (d, J=8.83 Hz, 1H), 7.19 (d, J=9.30 Hz, 1H), 7.21 (s, 1H), 7.26 (d, J=8.51 Hz, 1H), 7.48 (dd, J=1.73, 10.40 Hz, 1H), 7.55 (t, J=8.51 Hz, 1H), 7.64 (d, J=8.51 Hz, 1H), 7.99 (dd, J=2.21, 8.67 Hz, 1H), 8.45 (d, J=2.52 Hz, 1H), 9.01 (s, 1H), 12.38 (br s, 1H); MS (ESI) [M+1]$^+$ 528.

Example C-6

3-(5-(4-(2-chlorophenylcarbamoyl)-2-ethyl-3,4-dihydro-2H-benzo[b][1,4]oxazin-7-yl)pyridin-2-yloxy)-2,2-dimethylpropanoic acid

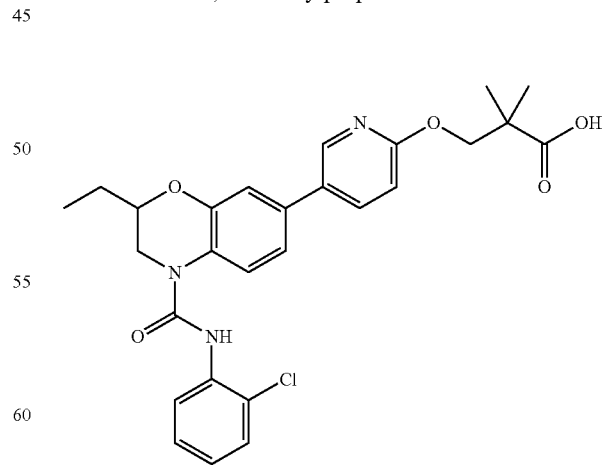

$^1$H NMR (500 MHz, DMSO-d$_6$) δ ppm 1.04 (t, J=7.41 Hz, 3H), 1.23 (s, 6H), 1.70 (tt, J=14.46, 7.13 Hz, 2H), 3.48 (dd, J=7.40, 13.57 Hz, 1H), 4.11 (dd, J=2.21, 13.40 Hz, 1H), 4.17-4.22 (m, 1H), 4.28 (s, 2H), 6.86 (d, J=8.83 Hz, 1H), 7.18-7.23 (m, 3H), 7.34 (t, J=7.88 Hz, 1H), 7.50 (d, J=8.04 Hz, 1H), 7.64 (d, J=7.88 Hz, 1H), 7.70 (d, J=8.20 Hz, 1H), 8.00 (dd, J=8.67, 2.68 Hz, 1H), 8.45 (d, J=2.52 Hz, 1H), 8.81 (s, 1H), 12.38 (br s, 1H); MS (ESI) [M+1]⁺ 510.

Example C-7

3-(5-(2-ethyl-4-(2-ethylphenylcarbamoyl)-3,4-dihydro-2H-benzo[b][1,4]oxazin-7-yl)pyridin-2-yloxy)-2,2-dimethylpropanoic acid

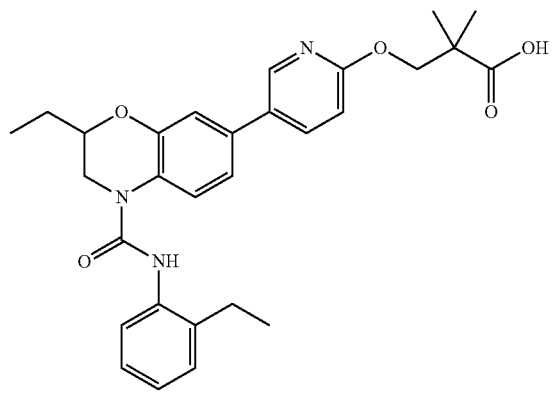 [SMILES: CCc1ccccc1NC(=O)N1CC(CC)Oc2cc(-c3ccc(OCC(C)(C)C(=O)O)nc3)ccc21]

¹H NMR (500 MHz, DMSO-d₆) δ ppm 1.04 (t, J=7.41 Hz, 3H), 1.16 (t, J=7.57 Hz, 3H), 1.23 (s, 6H), 1.65-1.77 (m, 2H), 2.60 (q, J=7.57 Hz, 2H), 3.51 (dd, J=13.40, 7.41 Hz, 1H), 4.07 (d, J=13.40 Hz, 1H), 4.14-4.21 (m, 1H), 4.28 (s, 2H), 6.86 (d, J=8.51 Hz, 1H), 7.14-7.20 (m, 4H), 7.26 (d, J=7.41 Hz, 1H), 7.29 (d, J=7.41 Hz, 1H), 7.67 (d, J=8.51 Hz, 1H), 7.98 (dd, J=2.21, 8.51 Hz, 1H), 8.44 (d, J=2.52 Hz, 1H), 8.59 (s, 1H), 12.39 (br s, 1H); MS (ESI) [M+1]⁺ 504.

Example C-8

3-(5-(4-(3-chloro-4-fluorophenylcarbamoyl)-2-ethyl-3,4-dihydro-2H-benzo[b][1,4]oxazin-7-yl)pyridin-2-yloxy)-2,2-dimethylpropanoic acid

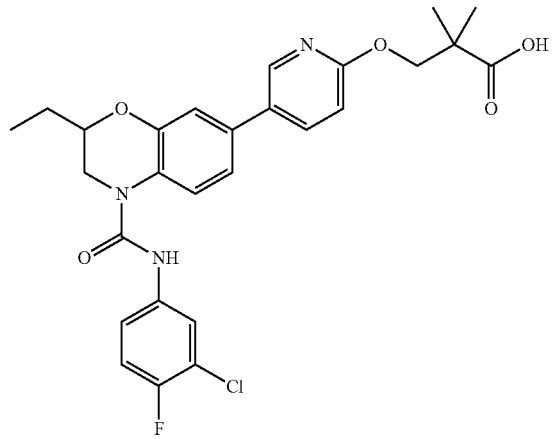 [SMILES: CCC1CN(C(=O)Nc2ccc(F)c(Cl)c2)c2ccc(-c3ccc(OCC(C)(C)C(=O)O)nc3)cc2O1]

¹H NMR (500 MHz, DMSO-d₆) δ ppm 1.02 (t, J=7.41 Hz, 3H), 1.23 (s, 6H), 1.64-1.75 (m, 2H), 3.46 (dd, J=13.56, 7.57 Hz, 1H), 4.05 (br d, J=13.57 Hz, 1H), 4.15-4.20 (m, 1H), 4.28 (s, 2H), 6.86 (d, J=8.83 Hz, 1H), 7.19 (d, J=8.67 Hz, 1H), 7.21 (s, 1H), 7.36 (t, J=8.99 Hz, 1H), 7.44-7.48 (m, 1H), 7.56 (d, J=8.51 Hz, 1H), 7.76 (dd, J=6.78, 2.99 Hz, 1H), 7.99 (dd, J=2.21, 8.36 Hz, 1H), 8.45 (d, J=2.84 Hz, 1H), 9.35 (s, 1H), 12.40 (br s, 1H); MS (ESI) [M+1]⁺ 528.

Example C-9

3-(5-(4-(2-ethylphenylcarbamoyl)-3,4-dihydro-2H-benzo[b][1,4]oxazin-7-yl)pyridin-2-yloxy)cyclopentanecarboxylic acid

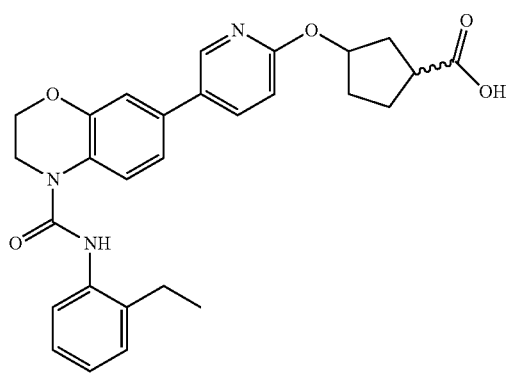 [SMILES: CCc1ccccc1NC(=O)N1CCOc2cc(-c3ccc(OC4CCC(C(=O)O)C4)nc3)ccc21]

¹H NMR (500 MHz, DMSO-d₆) δ ppm 1.16 (t, J=7.57 Hz, 3H), 1.75-1.85 (m, 2H), 1.89-1.96 (m, 1H), 1.98-2.17 (m, 3H), 2.60 (q, J=7.57 Hz, 2H), 2.93 (quin, J=8.12 Hz, 1H), 3.90 (t, J=4.41 Hz, 2H), 4.32 (t, J=4.41 Hz, 2H), 5.34-5.37 (m, 0.35H), 5.43-5.48 (m, 0.65H), 6.80 (d, J=8.51 Hz, 0.35H), 6.83 (d, J=8.67 Hz, 0.65H), 7.14-7.20 (m, 4H), 7.25 (d, J=7.25 Hz, 1H), 7.31 (d, J=7.23 Hz, 1H), 7.71 (d, J=8.20 Hz, 1H), 7.94-7.98 (m, 1H), 8.44 (d, J=2.52 Hz, 0.35H), 8.45 (d, J=2.52 Hz, 0.65H), 8.57 (s, 1H), 12.21 (br s, 1H); MS (ESI) [M+1]⁺ 488.

Example C-10

3-(5-(4-(phenylcarbamoyl)-3,4-dihydro-2H-benzo[b][1,4]oxazin-7-yl)pyridin-2-yloxy)cyclopentanecarboxylic acid

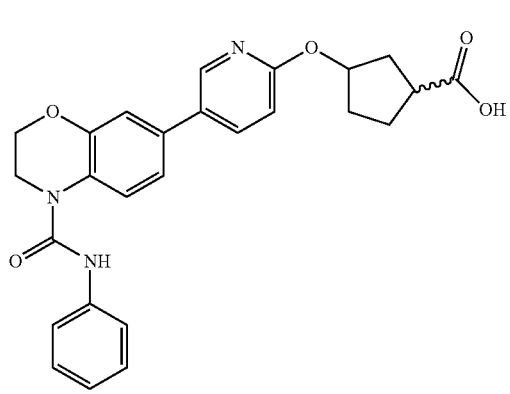 [SMILES: O=C(O)C1CCC(Oc2ccc(-c3ccc4c(c3)OCCN4C(=O)Nc3ccccc3)cn2)C1]

¹H NMR (500 MHz, DMSO-d₆) δ ppm 1.75-1.85 (m, 2H), 1.89-1.96 (m, 1H), 1.97-2.17 (m, 3H), 2.93 (quin, J=7.88 Hz, 1H), 3.87 (t, J=4.41 Hz, 2H), 4.30 (t, J=4.41 Hz, 2H), 5.33-5.37 (m, 0.35H), 5.45 (m, 0.65H), 6.81 (d, J=8.51 Hz, 0.35H), 6.83 (d, J=8.51 Hz, 0.65H), 7.00 (t, J=7.41 Hz, 1H), 7.16-7.20 (m, 2H), 7.29 (t, J=7.88 Hz, 2H), 7.50 (d, J=8.51 Hz, 2H), 7.59 (d, J=8.51 Hz, 1H), 7.95-7.98 (m, 1H), 8.44 (d, J=2.36 Hz, 0.35H), 8.45 (d, J=2.36 Hz, 0.65H), 9.17 (s, 1H), 12.15 (br s, 1H); MS (ESI) [M+1]$^+$ 460.

Example C-11

1-(5-(4-(phenylcarbamoyl)-3,4-dihydro-2H-benzo[b][1,4]oxazin-7-yl)pyrimidin-2-yl)pyrrolidine-3-carboxylic acid

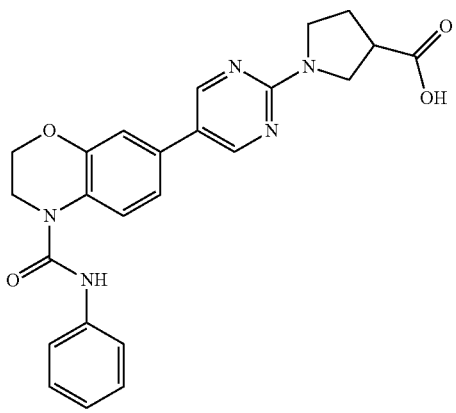 [SMILES: O=C(O)C1CCN(c2ncc(-c3ccc4c(c3)OCCN4C(=O)Nc3ccccc3)cn2)C1]

$^1$H NMR (500 MHz, DMSO-d$_6$) δ ppm 2.12-2.25 (m, 2H), 3.17 (t, J=6.55 Hz, 1H), 3.52-3.63 (m, 2H), 3.68-3.74 (m, 2H), 3.86 (t, J=4.57 Hz, 2H), 4.29 (t, J=4.41 Hz, 2H), 7.01 (t, J=7.41 Hz, 1H), 7.16 (d, J=9.14 Hz, 1H), 7.19 (s, 1H), 7.29 (t, J=7.88 Hz, 2H), 7.50 (d, J=8.20 Hz, 2H), 7.56 (d, J=8.51 Hz, 1H), 8.68 (s, 2H), 9.14 (s, 1H), 12.59 (br s, 1H); MS (ESI) [M+1]$^+$ 446.

Example C-12

1-(5-(2-methyl-4-(phenylcarbamoyl)-3,4-dihydro-2H-benzo[b][1,4]oxazin-7-yl)pyrimidin-2-yl)pyrrolidine-3-carboxylic acid

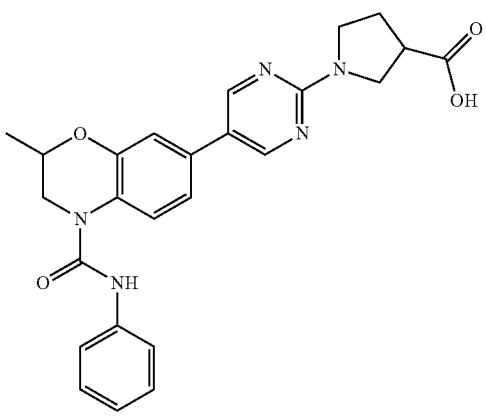 [SMILES: CC1CN(C(=O)Nc2ccccc2)c2ccc(-c3cnc(N4CCC(C(=O)O)C4)nc3)cc2O1]

$^1$H NMR (500 MHz, DMSO-d$_6$) δ ppm 1.35 (d, J=6.31 Hz, 3H), 2.12-2.26 (m, 2H), 3.19 (quin, J=7.01 Hz, 1H), 3.34-3.37 (m, 1H), 3.52-3.63 (m, 2H), 3.69-3.76 (m, 2H), 4.10 (br d, J=13.24 Hz, 1H), 4.32-4.38 (m, 1H), 7.00 (t, J=7.57 Hz, 1H), 7.16 (d, J=8.67 Hz, 1H), 7.18 (s, 1H), 7.29 (t, J=8.04 Hz, 2H), 7.50 (d, J=8.51 Hz, 2H), 7.54 (d, J=8.36 Hz, 1H), 8.68 (s, 2H), 9.15 (s, 1H), 12.54 (br s, 1H); MS (ESI) [M+1]$^+$ 460.

Example C-13

1-(5-(2-ethyl-4-(phenylcarbamoyl)-3,4-dihydro-2H-benzo[b][1,4]oxazin-7-yl)pyrimidin-2-yl)pyrrolidine-3-carboxylic acid

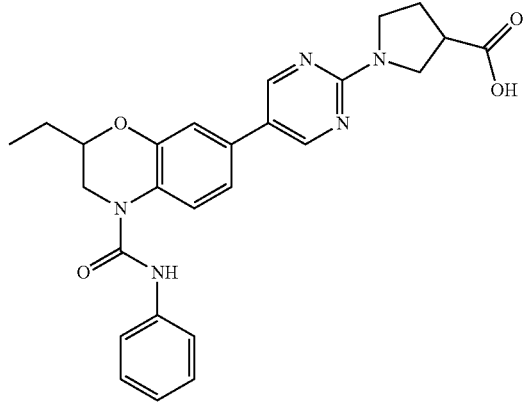 [SMILES: CCC1CN(C(=O)Nc2ccccc2)c2ccc(-c3cnc(N4CCC(C(=O)O)C4)nc3)cc2O1]

$^1$H NMR (500 MHz, DMSO-d$_6$) δ ppm 1.02 (t, J=7.41 Hz, 3H), 1.62-1.75 (m, 2H), 2.13-2.26 (m, 2H), 3.20 (quin, J=7.09 Hz, 1H), 3.46 (dd, J=13.56, 7.25 Hz, 1H), 3.53-3.63 (m, 2H), 3.69-3.76 (m, 2H), 4.03 (br d, J=13.24 Hz, 1H), 4.13-4.18 (m, 1H), 7.00 (t, J=7.57 Hz, 1H), 7.16 (dd, J=2.05, 8.51 Hz, 1H), 7.19 (d, J=2.05 Hz, 1H), 7.29 (t, J=7.88 Hz, 2H), 7.49 (d, J=8.20 Hz, 2H), 7.52 (d, J=8.67 Hz, 1H), 8.68 (s, 2H), 9.15 (s, 1H), 12.54 (br s, 1H); MS (ESI) [M+1]$^+$ 474.

Example C-14

(1s,2s)-2-((5-(2-ethyl-4-(phenylcarbamoyl)-3,4-dihydro-2H-benzo[b][1,4]oxazin-7-yl)pyridin-2-yloxy)methyl)cyclopropanecarboxylic acid

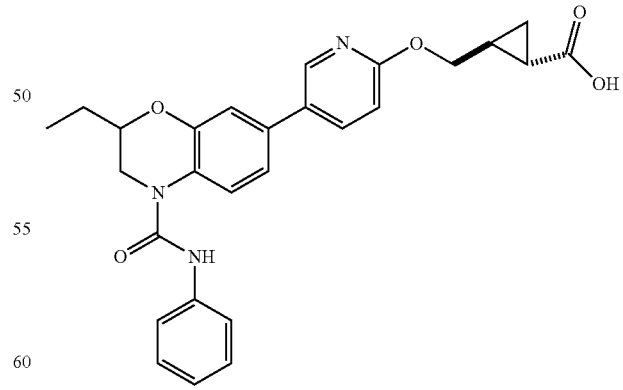

$^1$H NMR (500 MHz, DMSO-d$_6$) δ ppm 0.95-1.00 (m, 1H), 1.02 (t, J=7.41 Hz, 3H), 1.05-1.10 (m, 1H), 1.61-1.80 (m, 4H), 3.47 (dd, J=13.56, 7.25 Hz, 1H), 4.04 (dd, J=2.05, 13.57 Hz, 1H), 4.12 (dd, J=6.31, 11.35 Hz, 1H), 4.17 (dq, J=2.21, 6.35 Hz, 1H), 4.30 (dd, J=6.31, 11.35 Hz, 1H), 6.90 (d, J=8.51

Hz, 1H), 7.01 (t, J=7.41 Hz, 1H), 7.18 (dd, J=2.05, 8.36 Hz, 1H), 7.20 (d, J=2.05 Hz, 1H), 7.29 (t, J=7.88 Hz, 2H), 7.50 (d, J=8.36 Hz, 2H), 7.55 (d, J=8.51 Hz, 1H), 8.00 (dd, J=8.51, 2.52 Hz, 1H), 8.44 (d, J=2.52 Hz, 1H), 9.17 (s, 1H), 12.29 (br s, 1H); MS (ESI) [M+1]$^+$ 474.

Example C-15

1-(5-(4-(2-ethylphenylcarbamoyl)-3,4-dihydro-2H-benzo[b][1,4]oxazin-7-yl)pyrimidin-2-yl)pyrrolidine-3-carboxylic acid

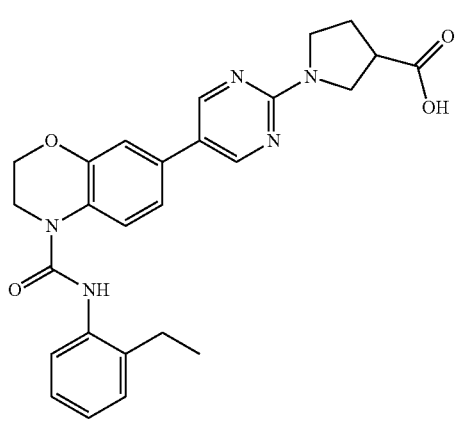 [SMILES: CCc1ccccc1NC(=O)N1CCOc2cc(-c3cnc(N4CCC(C(=O)O)C4)nc3)ccc21]

$^1$H NMR (500 MHz, DMSO-d$_6$) δ ppm 1.16 (t, J=7.41 Hz, 3H), 2.13-2.23 (m, 2H), 2.60 (q, J=7.41 Hz, 2H), 3.16 (br t, J=7.09 Hz, 1H), 3.51-3.62 (m, 2H), 3.71 (d, J=6.94 Hz, 2H), 3.89 (t, J=4.57 Hz, 2H), 4.31 (t, J=4.41 Hz, 2H), 7.14-7.20 (m, 4H), 7.25 (d, J=6.46 Hz, 1H), 7.30 (d, J=7.57 Hz, 1H), 7.68 (d, J=8.98 Hz, 1H), 8.55 (s, 1H), 8.67 (s, 2H), 12.60 (br s, 1H); MS (ESI) [M+1]$^+$474.

Example C-16 methyl 1-(5-(4-(2-ethylphenylcarbamoyl)-2-methyl-3,4-dihydro-2H-benzo[b][1,4]oxazin-7-yl)pyrimidin-2-yl)pyrrolidine-3-carboxylate

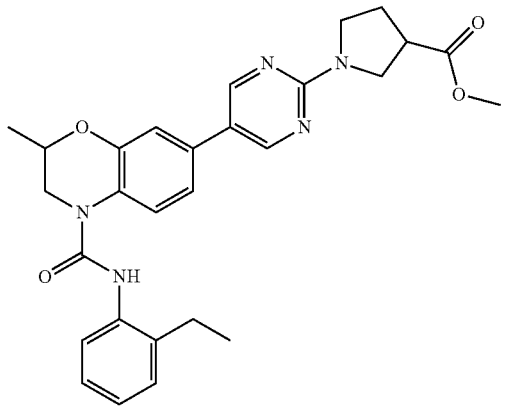

$^1$H NMR (500 MHz, DMSO-d$_6$) δ ppm 1.16 (t, J=7.62 Hz, 3H), 1.36 (d, J=6.31 Hz, 3H), 2.13-2.20 (m, 1H), 2.22-2.29 (m, 1H), 2.60 (q, J=7.62 Hz, 2H), 3.29-3.32 (m, 1H), 3.40 (dd, J=13.40, 7.41 Hz, 1H), 3.53-3.67 (m, 2H), 3.66 (s, 3H), 3.71 (dd, J=6.15, 11.51 Hz, 1H), 3.78 (dd, J=7.88, 11.51 Hz, 1H), 4.09 (dd, J=2.20, 13.57 Hz, 1H), 4.36-4.42 (m, 1H), 7.14-7.20 (m, 4H), 7.26 (dd, J=2.36, 13.57 Hz, 1H), 7.27 (dd, J=1.85, 13.57 Hz, 1H), 7.66 (d, J=8.51 Hz, 1H), 8.57 (s, 1H), 8.68 (s, 2H); MS (ESI) [M+1]$^+$ 502.

Example C-17

1-(5-(4-(2-ethylphenylcarbamoyl)-2-methyl-3,4-dihydro-2H-benzo[b][1,4]oxazin-7-yl)pyrimidin-2-yl)pyrrolidine-3-carboxylic acid

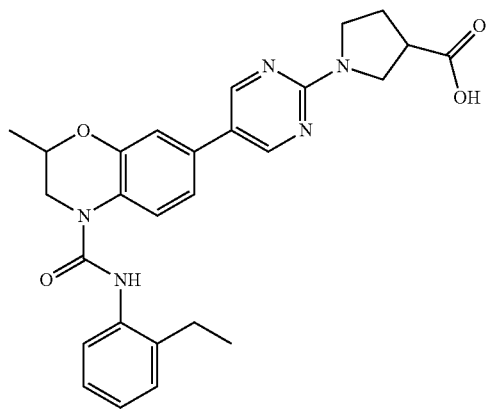 [SMILES: CCc1ccccc1NC(=O)N1CC(C)Oc2cc(-c3cnc(N4CCC(C(=O)O)C4)nc3)ccc21]

$^1$H NMR (500 MHz, DMSO-d$_6$) δ ppm 1.16 (t, J=7.57 Hz, 3H), 1.36 (d, J=6.46 Hz, 3H), 2.12-2.25 (m, 2H), 2.60 (q, J=7.57 Hz, 2H), 3.16-3.22 (m, 1H), 3.40 (dd, J=13.56, 7.57 Hz, 1H), 3.52-3.63 (m, 2H), 3.69-3.76 (m, 2H), 4.09 (d, J=13.40 Hz, 1H), 4.36-4.41 (m, 1H), 7.14-7.20 (m, 4H), 7.26 (d, J=13.57 Hz, 1H), 7.27 (d, J=13.57 Hz, 1H), 7.65 (d, J=8.20 Hz, 1H), 8.57 (s, 1H), 8.68 (s, 2H), 12.56 (br s, 1H); MS (ESI) [M+1]$^+$ 488.

Example C-18

1-(5-(2-ethyl-4-(2-ethylphenylcarbamoyl)-3,4-dihydro-2H-benzo[b][1,4]oxazin-7-yl)pyrimidin-2-yl)pyrrolidine-3-carboxylic acid

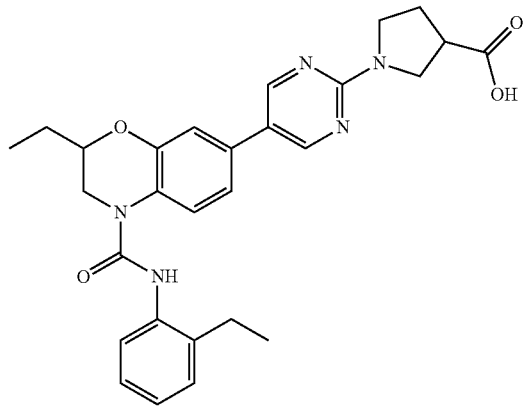 [SMILES: CCc1ccccc1NC(=O)N1CC(CC)Oc2cc(-c3cnc(N4CCC(C(=O)O)C4)nc3)ccc21]

$^1$H NMR (500 MHz, DMSO-d$_6$) δ ppm 1.04 (t, J=7.41 Hz, 3H), 1.15 (t, J=7.57 Hz, 3H), 1.63-1.77 (m, 2H), 2.12-2.26 (m, 2H), 2.60 (q, J=7.72 Hz, 2H), 3.20 (quin, J=7.01 Hz, 1H), 3.49 (dd, J=7.09, 13.57 Hz, 1H), 3.52-3.63 (m, 2H), 3.69-3.76 (m, 2H), 4.06 (dd, J=2.21, 13.57 Hz, 1H), 4.16 (qd, J=6.78, 2.68 Hz, 1H), 7.14-7.20 (m, 4H), 7.26 (dd, J=2.05, 14.35 Hz, 1H), 7.27 (dd, J=2.05, 14.35 Hz, 1H), 7.64 (d, J=8.51 Hz, 1H), 8.57 (s, 1H), 8.68 (s, 2H), 12.54 (br s, 1H); MS (ESI) [M+1]$^+$ 502.

Example C-19

(1s,2s)-2-((5-(2-ethyl-4-(2-ethylphenylcarbamoyl)-3,4-dihydro-2H-benzo[b][1,4]oxazin-7-yl)pyridin-2-yloxy)methyl)cyclopropanecarboxylic acid

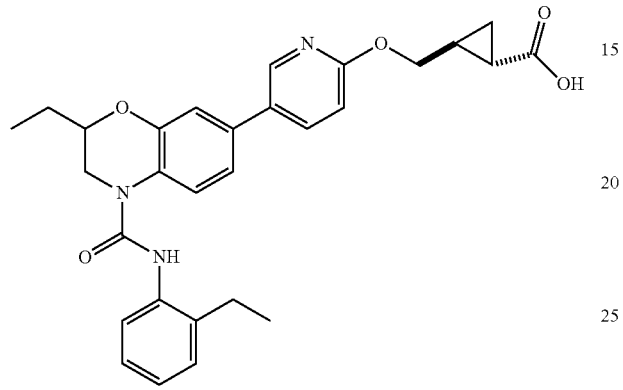

$^1$H NMR (500 MHz, DMSO-d$_6$) δ ppm 0.97-1.02 (m, 1H), 1.03-1.09 (m, 1H), 1.04 (t, J=7.41 Hz, 3H), 1.16 (t, J=7.57 Hz, 3H), 1.61-1.80 (m, 4H), 2.60 (q, J=7.41 Hz, 2H), 3.51 (dd, J=13.71, 7.09 Hz, 1H), 4.07 (d, J=13.08 Hz, 1H), 4.12 (dd, J=7.72, 11.35 Hz, 1H), 4.17 (br q, J=6.62 Hz, 1H), 4.30 (dd, J=11.35, 6.31 Hz, 1H), 6.90 (d, J=8.83 Hz, 1H), 7.13-7.21 (m, 4H), 7.25 (d, J=6.62 Hz, 1H), 7.29 (d, J=7.72 Hz, 1H), 7.67 (d, J=8.20 Hz, 1H), 8.00 (dd, J=2.52, 8.67 Hz, 1H), 8.44 (d, J=2.84 Hz, 1H), 8.59 (s, 1H), 12.24 (br s, 1H); MS (ESI) [M+1]$^+$ 502.

Example C-20

1-(5-(4-(4-chloro-2-fluorophenylcarbamoyl)-3,4-dihydro-2H-benzo[b][1,4]oxazin-7-yl)pyrimidin-2-yl)pyrrolidine-3-carboxylic acid

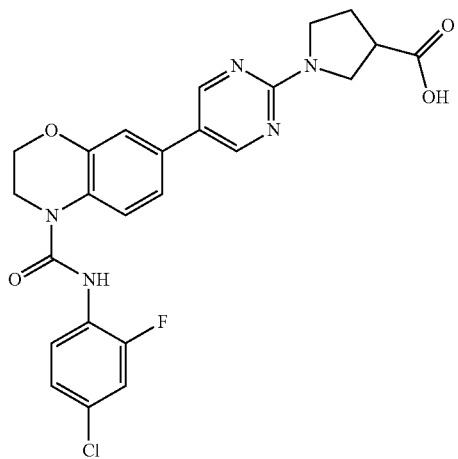 [SMILES: O=C(O)C1CCN(c2ncc(-c3ccc4c(c3)OCCN4C(=O)Nc3ccc(Cl)cc3F)cn2)C1]

$^1$H NMR (500 MHz, DMSO-d$_6$) δ ppm 2.12-2.25 (m, 2H), 3.15-3.21 (m, 1H), 3.52-3.63 (m, 2H), 3.69-3.75 (m, 2H), 3.88 (t, J=4.25 Hz, 2H), 4.30 (t, J=4.25 Hz, 2H), 7.18 (d, J=8.83 Hz, 1H), 7.20 (s, 1H), 7.26 (d, J=8.50 Hz, 1H), 7.48 (dd, J=2.05, 10.25 Hz, 1H), 7.57 (t, J=8.51 Hz, 1H), 7.65 (d, J=8.20 Hz, 1H), 8.68 (s, 2H), 8.96 (s, 1H), 12.60 (br s, 1H); MS (ESI) [M+1]$^+$ 498.

Example C-21

1-(5-(4-(4-chloro-2-fluorophenylcarbamoyl)-2-methyl-3,4-dihydro-2H-benzo[b][1,4]oxazin-7-yl)pyrimidin-2-yl)pyrrolidine-3-carboxylic acid

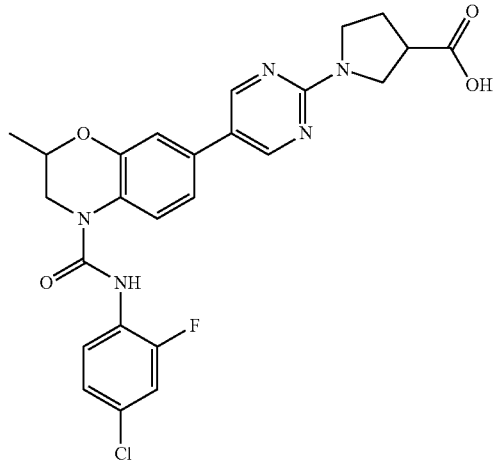 [SMILES: CC1CN(C(=O)Nc2ccc(Cl)cc2F)c2ccc(-c3cnc(N4CCC(C(=O)O)C4)nc3)cc2O1]

$^1$H NMR (500 MHz, DMSO-d$_6$) δ ppm 1.35 (d, J=6.15 Hz, 3H), 2.12-2.26 (m, 2H), 3.16-3.22 (m, 1H), 3.37 (dd, J=7.57, 13.24 Hz, 1H), 3.52-3.63 (m, 2H), 3.69-3.76 (m, 2H), 4.10 (d, J=13.71 Hz, 1H), 4.34-4.40 (m, 1H), 7.17 (d, J=8.83 Hz, 1H), 7.19 (s, 1H), 7.26 (d, J=8.83 Hz, 1H), 7.48 (d, J=10.56 Hz, 1H), 7.55 (t, J=8.67 Hz, 1H), 7.62 (d, J=8.20 Hz, 1H), 8.67 (s, 2H), 8.99 (s, 1H), 12.59 (br s, 1H); MS (ESI) [M+1]$^+$ 512.

Example C-22

1-(5-(4-(4-chloro-2-fluorophenylcarbamoyl)-2-ethyl-3,4-dihydro-2H-benzo[b][1,4]oxazin-7-yl)pyrimidin-2-yl)pyrrolidine-3-carboxylic acid

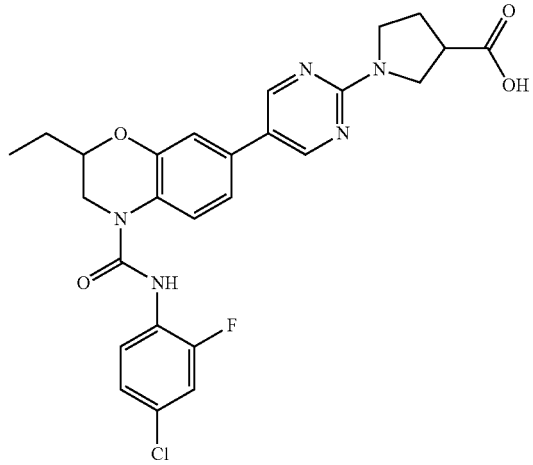 [SMILES: CCC1CN(C(=O)Nc2ccc(Cl)cc2F)c2ccc(-c3cnc(N4CCC(C(=O)O)C4)nc3)cc2O1]

$^1$H NMR (500 MHz, DMSO-d$_6$) δ ppm 1.02 (t, J=7.41 Hz, 3H), 1.63-1.74 (m, 2H), 2.08-2.25 (m, 2H), 3.18 (quin, J=6.94 Hz, 1H), 3.47 (dd, J=13.24, 7.25 Hz, 1H), 3.52-3.63 (m, 2H), 3.69-3.75 (m, 2H), 4.05 (d, J=13.57 Hz, 1H), 4.17 (qd, J=6.88, 2.68 Hz, 1H), 7.17 (d, J=8.51 Hz, 1H), 7.19 (s, 1H), 7.26 (d, J=8.99 Hz, 1H), 7.48 (br d, J=10.56 Hz, 1H), 7.55 (t, J=8.35 Hz, 1H), 7.60 (d, J=8.67 Hz, 1H), 8.68 (s, 2H), 8.98 (s, 1H), 12.65 (br s, 1H); MS (ESI) [M+1]+ 526.

Example C-23

(1s,2s)-2-((5-(4-(4-chloro-2-fluorophenylcarbamoyl)-2-ethyl-3,4-dihydro-2H-benzo[b][1,4]oxazin-7-yl)pyridin-2-yloxy)methyl)cyclopropanecarboxylic acid

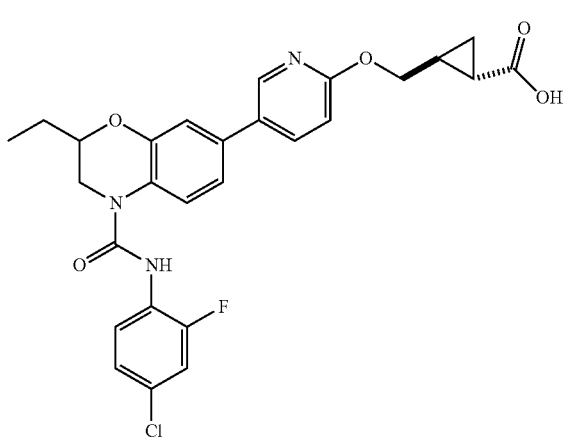

$^1$H NMR (500 MHz, DMSO-d$_6$) δ ppm 0.97-1.00 (m, 1H), 1.02 (t, J=7.41 Hz, 3H), 1.05-1.10 (m, 1H), 1.61-1.80 (m, 4H), 3.49 (dd, J=13.56, 7.25 Hz, 1H), 4.06 (d, J=13.08 Hz, 1H), 4.12 (dd, J=7.57, 11.19 Hz, 1H), 4.18 (qd, J=2.05, 6.94 Hz, 1H), 4.30 (dd, J=6.31, 11.67 Hz, 1H), 6.90 (d, J=8.51 Hz, 1H), 7.19 (d, J=8.67 Hz, 1H), 7.21 (s, 1H), 7.26 (d, J=8.99 Hz, 1H), 7.48 (br d, J=10.40 Hz, 1H), 7.55 (t, J=8.67 Hz, 1H), 7.64 (d, J=8.51 Hz, 1H), 8.00 (dd, J=2.50, 8.83 Hz, 1H), 8.45 (d, J=2.21 Hz, 1H), 9.01 (s, 1H), 12.27 (br s, 1H); MS (ESI) [M+1]+ 526.

Example C-24

2,2-dimethyl-3-(5-(2-methyl-4-(phenylcarbamoyl)-3,4-dihydro-2H-benzo[b][1,4]oxazin-7-yl)pyrimidin-2-yloxy)propanoic acid

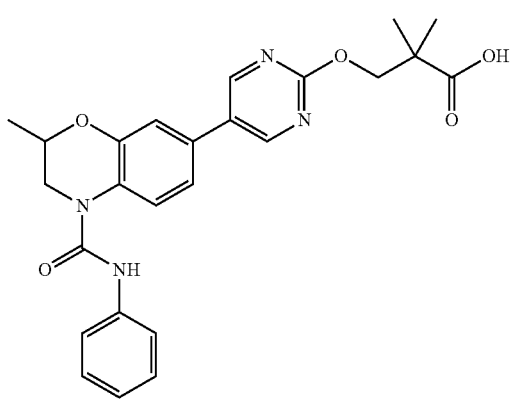

$^1$H NMR (500 MHz, DMSO-d$_6$) δ ppm 1.24 (s, 6H), 1.36 (d, J=6.31 Hz, 3H), 3.34-3.40 (m, 1H), 4.12 (br d, J=13.24 Hz, 1H), 4.33 (s, 2H), 4.37 (dt, J=2.52, 7.09 Hz, 1H), 7.01 (t, J=7.25 Hz, 1H), 7.26 (dd, J=2.05, 8.67 Hz, 1H), 7.28-7.32 (m, 3H), 7.50 (d, J=8.51 Hz, 2H), 7.61 (d, J=8.51 Hz, 1H), 8.91 (s, 2H), 9.20 (s, 1H), 12.49 (br s, 1H); MS (ESI) [M+1]+ 463.

Example C-25

3-(5-(4-(2-ethylphenylcarbamoyl)-2-methyl-3,4-dihydro-2H-benzo[b][1,4]oxazin-7-yl)pyrimidin-2-yloxy)-2,2-dimethylpropanoic acid

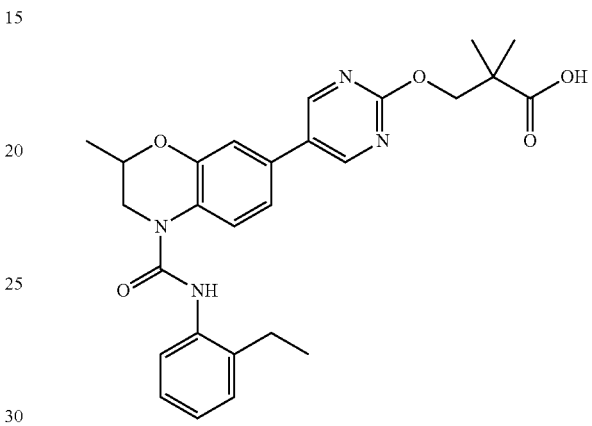

$^1$H NMR (500 MHz, DMSO-d$_6$) δ ppm 1.16 (t, J=7.41 Hz, 3H), 1.24 (s, 6H), 1.37 (d, J=6.15 Hz, 3H), 2.60 (q, J=7.41 Hz, 2H), 3.43 (dd, J=13.40, 7.41 Hz, 1H), 4.11 (d, J=13.24 Hz, 1H), 4.34 (s, 2H), 4.38-4.43 (m, 1H), 7.15-7.21 (m, 2H), 7.24-7.31 (m, 4H), 7.72 (d, J=8.51 Hz, 1H), 8.62 (s, 1H), 8.90 (s, 2H), 12.47 (br s, 1H); MS (ESI) [M+1]+ 491.

Example C-26

3-(5-(4-(4-chloro-2-fluorophenylcarbamoyl)-2-methyl-3,4-dihydro-2H-benzo[b][1,4]oxazin-7-yl)pyrimidin-2-yloxy)-2,2-dimethylpropanoic acid

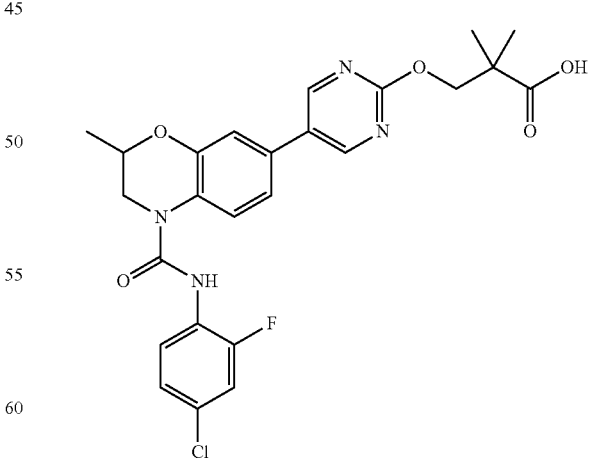

$^1$H NMR (500 MHz, DMSO-d$_6$) δ ppm 1.23 (s, 6H), 1.36 (d, J=6.15 Hz, 3H), 3.39 (dd, J=7.88, 13.57 Hz, 1H), 4.12 (d, J=13.08 Hz, 1H), 4.33 (s, 2H), 4.36-4.42 (m, 1H), 7.27 (d, J=8.51 Hz, 2H), 7.32 (s, 1H), 7.49 (d, J=10.40 Hz, 1H), 7.56

(t, J=8.67 Hz, 1H), 7.69 (d, J=8.67 Hz, 1H), 8.91 (d, J=1.10 Hz, 2H), 9.04 (s, 1H), 12.48 (br s, 1H); MS (ESI) [M+1]$^+$ 515.

Example C-27

3-(5-(2-ethyl-4-(phenylcarbamoyl)-3,4-dihydro-2H-benzo[b][1,4]oxazin-7-yl)pyrimidin-2-yloxy)-2,2-dimethylpropanoic acid

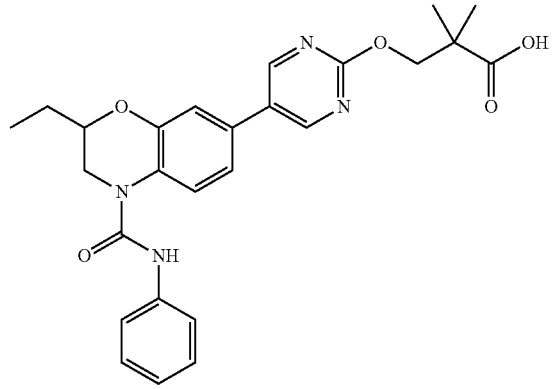

$^1$H NMR (500 MHz, DMSO-d$_6$) δ ppm 1.03 (t, J=7.57 Hz, 3H), 1.24 (s, 6H), 1.65-1.75 (m, 2H), 3.48 (dd, J=13.56, 7.25 Hz, 1H), 4.05 (d, J=12.93 Hz, 1H), 4.15-4.20 (m, 1H), 4.33 (s, 2H), 7.02 (t, J=7.25 Hz, 1H), 7.24-7.32 (m, 4H), 7.50 (d, J=8.51 Hz, 2H), 7.59 (d, J=8.36 Hz, 1H), 8.91 (d, J=0.95 Hz, 2H), 9.20 (s, 1H), 12.48 (br s, 1H); MS (ESI) [M+1]$^+$ 477.

Example C-28

3-(5-(2-ethyl-4-(2-ethylphenylcarbamoyl)-3,4-dihydro-2H-benzo[b][1,4]oxazin-7-yl)pyrimidin-2-yloxy)-2,2-dimethylpropanoic acid

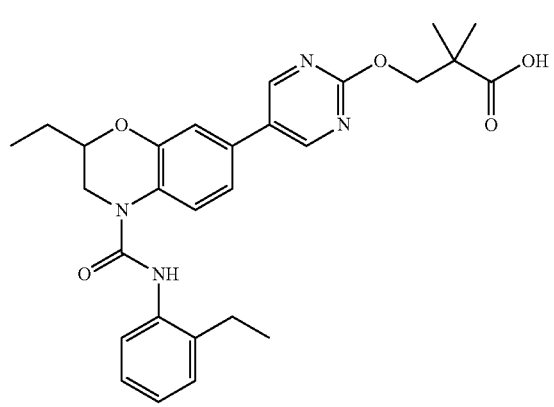

$^1$H NMR (500 MHz, DMSO-d$_6$) δ ppm 1.05 (t, J=7.57 Hz, 3H), 1.16 (t, J=7.25 Hz, 3H), 1.24 (s, 6H), 1.65-1.77 (m, 2H), 2.60 (q, J=7.57 Hz, 2H), 3.51 (dd, J=13.56, 7.25 Hz, 1H), 4.08 (dd, J=2.05, 13.56 Hz, 1H), 4.18 (qd, J=6.73, 3.15 Hz, 1H), 4.33 (s, 2H), 7.15-7.21 (m, 2H), 7.24-7.32 (m, 4H), 7.71 (d, J=8.51 Hz, 1H), 8.62 (s, 1H), 8.91 (s, 2H), 12.48 (br s, 1H); MS (ESI) [M+1]$^+$ 505.

Example C-29 methyl 3-(5-(4-(4-chloro-2-fluorophenylcarbamoyl)-2-ethyl-3,4-dihydro-2H-benzo[b][1,4]oxazin-7-yl)pyrimidin-2-yloxy)-2,2-dimethylpropanoate

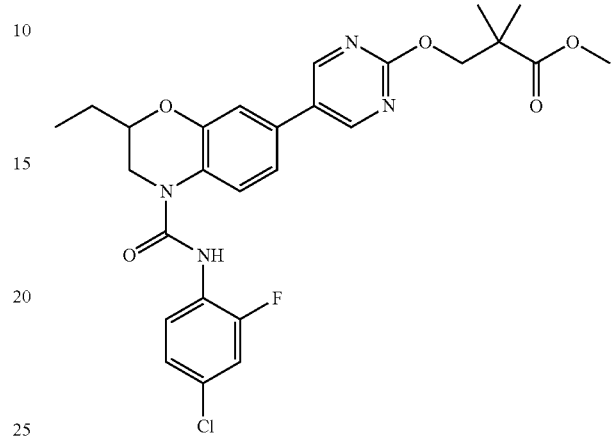

$^1$H NMR (500 MHz, DMSO-d$_6$) δ ppm 1.03 (t, J=7.41 Hz, 3H), 1.27 (s, 6H), 1.64-1.74 (m, 2H), 3.49 (dd, J=13.56, 7.57 Hz, 1H), 3.63 (s, 3H), 4.07 (d, J=13.56 Hz, 1H), 4.19 (br q, J=6.62 Hz, 1H), 4.37 (s, 2H), 7.27 (d, J=8.51 Hz, 2H), 7.33 (s, 1H), 7.49 (dd, J=2.05, 10.56 Hz, 1H), 7.55 (t, J=8.67 Hz, 1H), 7.68 (d, J=8.51 Hz, 1H), 8.91 (s, 2H), 9.04 (s, 1H); MS (ESI) [M+1]$^+$ 543.

Example C-30

3-(5-(4-(4-chloro-2-fluorophenylcarbamoyl)-2-ethyl-3,4-dihydro-2H-benzo[b][1,4]oxazin-7-yl)pyrimidin-2-yloxy)-2,2-dimethylpropanoic acid

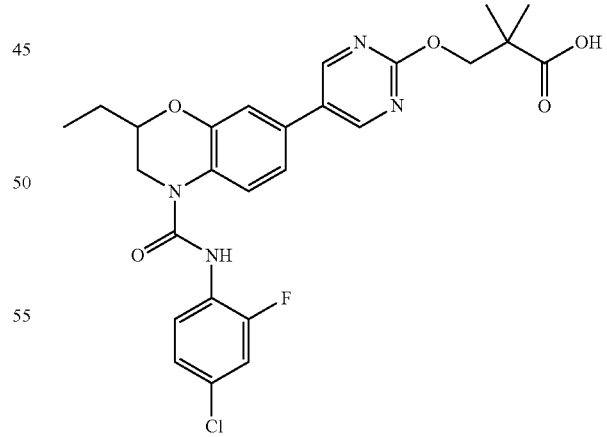

$^1$H NMR (500 MHz, DMSO-d$_6$) δ ppm 1.03 (t, J=7.41 Hz, 3H), 1.23 (s, 6H), 1.49-1.90 (m, 2H), 3.50 (dd, J=7.25, 13.40 Hz, 1H), 4.07 (d, J=12.78 Hz, 1H), 4.19 (br q, J=7.09 Hz, 1H), 4.33 (s, 2H), 7.27 (d, J=8.67 Hz, 2H), 7.33 (s, 1H), 7.49 (dd, J=2.05, 10.26 Hz, 1H), 7.55 (t, J=8.51 Hz, 1H), 7.67 (d, J=8.83 Hz, 1H), 8.91 (s, 2H), 9.04 (s, 1H), 12.50 (br s, 1H); MS (ESI) [M+1]$^+$ 529.

Example C-31

2-(5-(2-methyl-4-(phenylcarbamoyl)-3,4-dihydro-2H-benzo[b][1,4]oxazin-7-yl)pyridin-2-ylthio)acetic acid

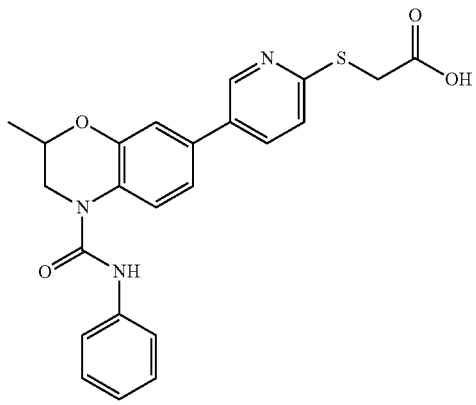 [SMILES: CC1CN(C(=O)Nc2ccccc2)c2ccc(-c3ccc(SCC(=O)O)nc3)cc2O1]

$^1$H NMR (500 MHz, DMSO-d$_6$) δ ppm 1.36 (d, J=6.31 Hz, 3H), 3.37 (dd, J=7.72, 13.24 Hz, 1H), 3.99 (s, 2H), 4.10 (d, J=12.93 Hz, 1H), 4.34-4.39 (m, 1H), 7.01 (t, J=Hz, 1H), 7.22-7.27 (m, 2H), 7.30 (t, J=7.57 Hz, 2H), 7.39 (d, J=8.51 Hz, 1H), 7.50 (d, J=8.51 Hz, 2H), 7.59 (d, J=8.20 Hz, 1H), 7.95 (dd, J=1.90, 8.36 Hz 1H), 8.73 (s, 1H), 9.20 (s, 1H), 12.80 (br s, 1H); MS (ESI) [M+1]$^+$ 436.

Example C-32

2-(5-(2-ethyl-4-(phenylcarbamoyl)-3,4-dihydro-2H-benzo[b][1,4]oxazin-7-yl)pyridin-2-ylthio)acetic acid

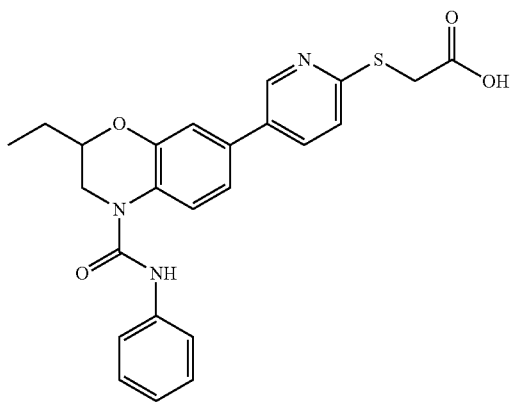 [SMILES: CCC1CN(C(=O)Nc2ccccc2)c2ccc(-c3ccc(SCC(=O)O)nc3)cc2O1]

$^1$H NMR (500 MHz, DMSO-d$_6$) δ ppm 1.02 (t, J=7.41 Hz, 3H), 1.64-1.75 (m, 2H), 3.48 (dd, J=13.24, 7.25 Hz, 1H), 3.97 (s, 2H), 4.04 (dd, J=13.40, 2.68 Hz, 1H), 4.15-4.20 (m, 1H), 7.01 (t, J=7.41 Hz, 1H), 7.22-7.31 (m, 4H), 7.38 (d, J=8.51 Hz, 1H), 7.50 (d, J=7.72 Hz, 2H), 7.56 (d, J=8.51 Hz, 1H), 7.96 (dd, J=8.51, 2.52 Hz, 1H), 8.72 (d, J=2.21 Hz, 1H), 9.20 (s, 1H), 12.79 (br s, 1H); MS (ESI) [M+1]$^+$ 450.

Example C-33 methyl 2-(5-(2-ethyl-4-(phenylcarbamoyl)-3,4-dihydro-2H-benzo[b][1,4]oxazin-7-yl)pyridin-2-yl)thio)acetate

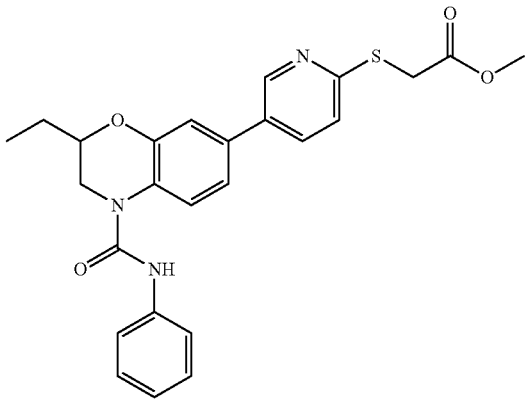 [SMILES: CCC1CN(C(=O)Nc2ccccc2)c2ccc(-c3ccc(SCC(=O)OC)nc3)cc2O1]

$^1$H NMR (500 MHz, DMSO-d$_6$) δ ppm 1.02 (t, J=7.41 Hz, 3H), 1.64-1.75 (m, 2H), 3.48 (dd, J=7.72, 13.71 Hz, 1H), 3.67 (s, 3H), 4.04 (d, J=13.71 Hz, 1H), 4.10 (s, 2H), 4.17 (q, J=6.66 Hz, 1H), 7.01 (t, J=7.41 Hz, 1H), 7.24 (br d, J=8.36 Hz, 1H), 7.26-7.32 (m, 3H), 7.41 (d, J=8.51 Hz, 1H), 7.50 (d, J=8.20 Hz, 2H), 7.57 (dd, J=8.51, 1.58 Hz, 1H), 7.96 (br d, J=8.43 Hz, 1H), 8.72 (s, 1H), 9.19 (s, 1H); MS (ESI) [M+1]$^+$ 464.

Example C-34

2-methyl-3-(5-(2-methyl-4-(phenylcarbamoyl)-3,4-dihydro-2H-benzo[b][1,4]oxazin-7-yl)pyridin-2-ylthio)propanoic acid

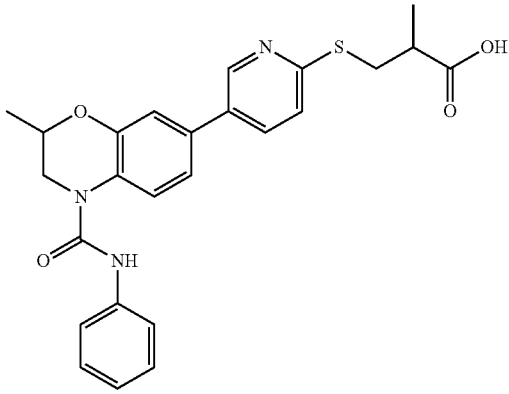 [SMILES: CC1CN(C(=O)Nc2ccccc2)c2ccc(-c3ccc(SCC(C)C(=O)O)nc3)cc2O1]

$^1$H NMR (500 MHz, DMSO-d$_6$) δ ppm 1.21 (d, J=6.94 Hz, 3H), 1.36 (d, J=6.31 Hz, 3H), 2.69-2.76 (m, 1H), 3.28-3.40 (m, 3H), 4.11 (br d, J=12.61 Hz, 1H), 4.34-4.40 (m, 1H), 7.01 (t, J=7.25 Hz, 1H), 7.22-7.27 (m, 2H), 7.30 (t, J=7.57 Hz, 2H), 7.35 (d, J=8.20 Hz, 1H), 7.50 (d, J=8.51 Hz, 2H), 7.59 (d, J=8.51 Hz, 1H), 7.93 (dd, J=2.21, 8.51 Hz, 1H), 8.76 (d, J=2.05 Hz, 1H), 9.20 (s, 1H), 12.44 (br s, J=1.58 Hz, 1H); MS (ESI) [M+1]$^+$ 464.

Example C-35

3-(5-(2-ethyl-4-(phenylcarbamoyl)-3,4-dihydro-2H-benzo[b][1,4]oxazin-7-yl)pyridin-2-ylthio)-2-methylpropanoic acid

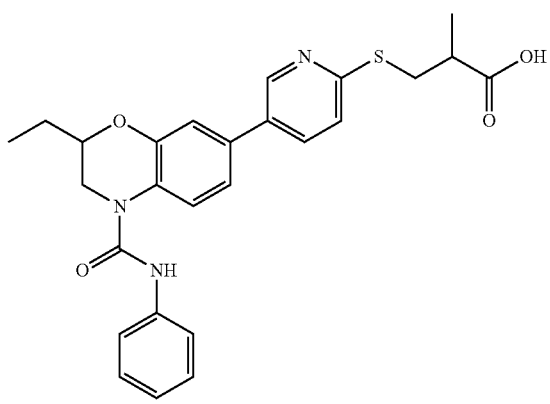 [SMILES: CCC1CN(C(=O)Nc2ccccc2)c2ccc(-c3ccc(SCC(C)C(=O)O)nc3)cc2O1]

$^1$H NMR (500 MHz, DMSO-d$_6$) δ ppm 1.03 (t, J=7.41 Hz, 3H), 1.21 (d, J=6.94 Hz, 3H), 1.64-1.75 (m, 2H), 2.72 (sxt, J=7.00 Hz, 1H), 3.28-3.40 (m, 2H), 3.48 (dd, J=13.56, 7.25 Hz, 1H), 4.04 (dd, J=13.40, 2.68 Hz, 1H), 4.15-4.20 (m, 1H), 7.01 (t, J=7.41 Hz, 1H), 7.24 (dd, J=2.05, 8.51 Hz, 1H), 7.26 (d, J=1.89 Hz, 1H), 7.30 (t, J=7.88 Hz, 2H), 7.35 (d, J=8.36 Hz, 1H), 7.50 (d, J=7.88 Hz, 2H), 7.58 (d, J=8.51 Hz, 1H), 7.93 (dd, J=2.36, 8.36 Hz, 1H), 8.76 (d, J=2.52 Hz, 1H), 9.20 (s, 1H), 12.47 (br s, 1H); MS (ESI) [M+1]$^+$ 478.

Example C-36

1-(5-(2-methyl-4-(phenylcarbamoyl)-3,4-dihydro-2H-benzo[b][1,4]oxazin-7-yl)pyrimidin-2-yl)piperidine-4-carboxylic acid

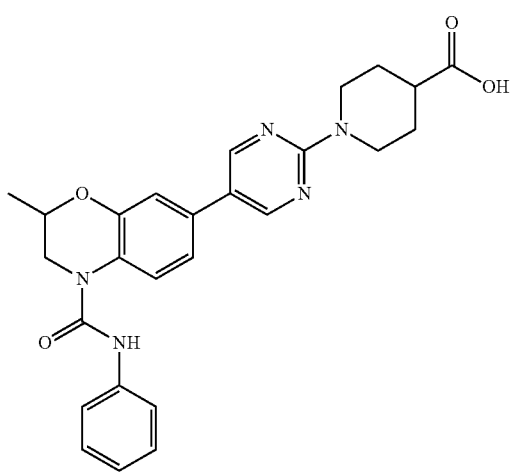 [SMILES: CC1CN(C(=O)Nc2ccccc2)c2ccc(-c3cnc(N4CCC(C(=O)O)CC4)nc3)cc2O1]

$^1$H NMR (500 MHz, DMSO-d$_6$) δ ppm 1.35 (d, J=6.31 Hz, 3H), 1.50 (dq, J=3.31, 11.35 Hz, 2H), 1.89 (br d, J=12.77 Hz, 2H), 2.52-2.59 (m, 1H), 3.10 (t, J=11.85 Hz, 2H), 3.34 (dd, J=7.56, 13.36 Hz, 1H), 4.10 (d, J=13.08 Hz, 1H), 4.32-4.38 (m, 1H), 4.55 (dt, J=13.24, 4.10 Hz, 2H), 7.00 (t, J=7.57 Hz, 1H), 7.16 (d, J=8.76 Hz, 1H), 7.19 (s, 1H), 7.29 (t, J=7.41 Hz, 2H), 7.50 (d, J=8.20 Hz, 2H), 7.54 (d, J=8.20 Hz, 1H), 8.68 (s, 2H), 9.16 (s, 1H), 12.36 (br s, 1H); MS (ESI) [M+1]$^+$ 474.

Example C-37

1-(5-(4-(2-ethylphenylcarbamoyl)-2-methyl-3,4-dihydro-2H-benzo[b][1,4]oxazin-7-yl)pyrimidin-2-yl)piperidine-4-carboxylic acid

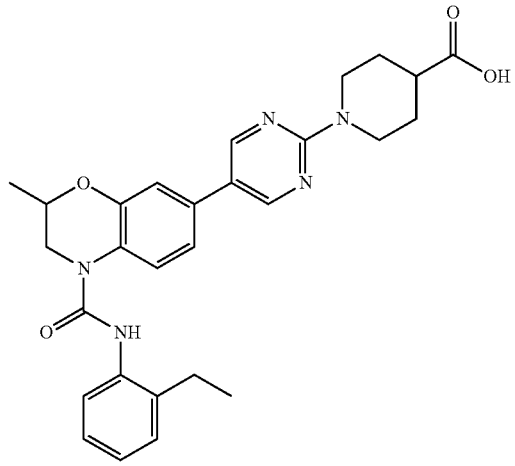 [SMILES: CCc1ccccc1NC(=O)N1CC(C)Oc2cc(-c3cnc(N4CCC(C(=O)O)CC4)nc3)ccc21]

$^1$H NMR (500 MHz, DMSO-d$_6$) δ ppm 1.16 (t, J=7.57 Hz, 3H), 1.36 (d, J=6.31 Hz, 3H), 1.50 (dq, J=3.78, 12.20 Hz, 2H), 1.89 (dd, J=2.99, 13.56 Hz, 2H), 2.54-2.63 (m, 1H), 2.60 (t, J=7.72 Hz, 2H), 3.10 (t, J=11.82 Hz, 2H), 3.40 (dd, J=13.56, 7.57 Hz, 1H), 4.09 (d, J=13.56 Hz, 1H), 4.36-4.41 (m, 1H), 4.55 (dt, J=13.24, 4.10 Hz, 2H), 7.14-7.20 (m, 4H), 7.25 (d, J=7.09 Hz, 1H), 7.28 (d, J=7.41 Hz, 1H), 7.66 (d, J=8.51 Hz, 1H), 8.56 (s, 1H), 8.68 (s, 2H), 12.29 (br s, 1H); MS (ESI) [M+1]$^+$ 502.

Example C-38

1-(5-(4-(4-chloro-2-fluorophenylcarbamoyl)-2-methyl-3,4-dihydro-2H-benzo[b][1,4]oxazin-7-yl)pyrimidin-2-yl)piperidine-4-carboxylic acid

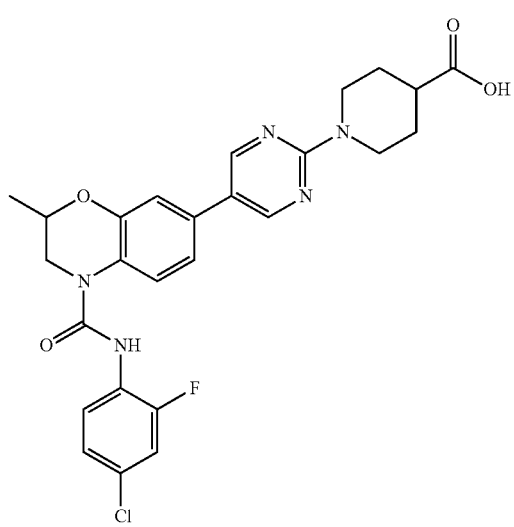 [SMILES: CC1CN(C(=O)Nc2ccc(Cl)cc2F)c2ccc(-c3cnc(N4CCC(C(=O)O)CC4)nc3)cc2O1]

$^1$H NMR (500 MHz, DMSO-d$_6$) δ ppm 1.35 (d, J=6.31 Hz, 3H), 1.50 (dq, J=4.14, 12.30 Hz, 2H), 1.89 (br d, J=13.40 Hz, 2H), 2.52-2.59 (m, 1H), 3.10 (dt, J=2.20, 12.45 Hz, 2H), 3.37 (dd, J=7.88, 13.51 Hz, 1H), 4.11 (dd, J=2.21, 13.24 Hz, 1H), 4.34-4.40 (m, 1H), 4.55 (dt, J=13.32, 4.06 Hz, 2H), 7.17 (d, J=8.99 Hz, 1H), 7.20 (s, 1H), 7.26 (br d, J=8.67 Hz, 1H), 7.48

(dd, J=1.90, 10.40 Hz, 1H), 7.56 (t, J=8.67 Hz, 1H), 7.63 (d, J=8.20 Hz, 1H), 8.68 (s, 2H), 8.99 (s, 1H), 12.32 (br s, 1H); MS (ESI) [M+1]+ 526.

Example C-39

2-(1-(5-(2-methyl-4-(phenylcarbamoyl)-3,4-dihydro-2H-benzo[b][1,4]oxazin-7-yl)pyrimidin-2-yl)pyrrolidin-3-yl)acetic acid

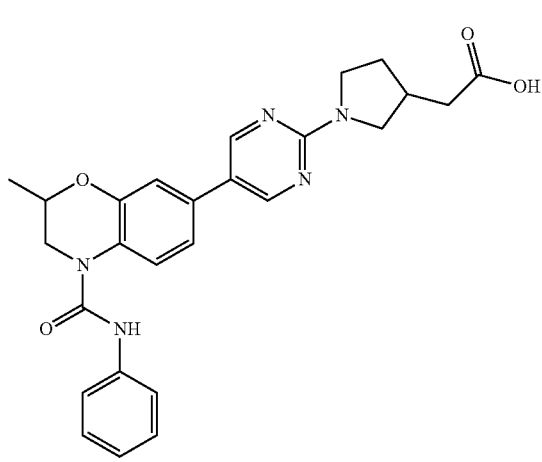 [SMILES: CC1CN(C(=O)Nc2ccccc2)c2ccc(-c3cnc(N4CCC(CC(=O)O)C4)nc3)cc2O1]

$^1$H NMR (500 MHz, DMSO-d$_6$) δ ppm 1.35 (d, J=6.31 Hz, 3H), 1.64-1.71 (m, 1H), 2.11-2.19 (m, 1H), 2.42 (d, J=7.41 Hz, 2H), 2.54-2.61 (m, 1H), 3.15 (dd, J=7.88, 11.03 Hz, 1H), 3.30-3.33 (m, 1H), 3.43-3.50 (m, 1H), 3.63-3.68 (m, 1H), 3.81 (dd, J=7.25, 11.19 Hz, 1H), 4.10 (br d, J=13.56 Hz, 1H), 4.32-4.38 (m, 1H), 7.00 (t, J=7.41 Hz, 1H), 7.15 (br d, J=8.67 Hz, 1H), 7.17 (s, 1H), 7.29 (t, J=7.72 Hz, 2H), 7.49 (d, J=8.20 Hz, 2H), 7.54 (d, J=8.67 Hz, 2H), 8.66 (s, 2H), 9.15 (s, 1H), 12.23 (br s, 1H); MS (ESI) [M+1]+ 474.

Example C-40

1-(5-(2-methyl-4-(phenylcarbamoyl)-3,4-dihydro-2H-benzo[b][1,4]oxazin-7-yl)pyridin-2-yl)piperidine-4-carboxylic acid

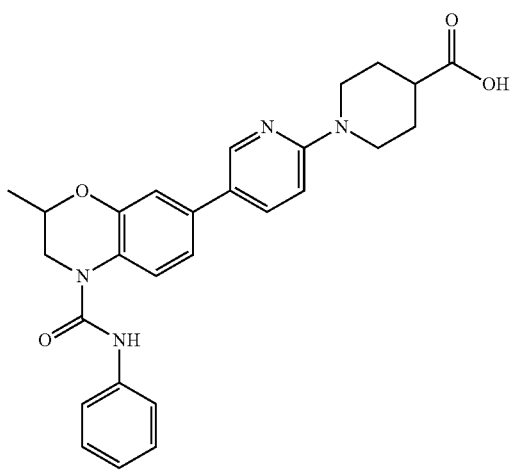 [SMILES: CC1CN(C(=O)Nc2ccccc2)c2ccc(-c3ccc(N4CCC(C(=O)O)CC4)nc3)cc2O1]

$^1$H NMR (500 MHz, DMSO-d$_6$) δ ppm 1.35 (d, J=6.31 Hz, 3H), 1.54 (dq, J=3.78, 12.45 Hz, 2H), 1.88 (br d, J=13.08 Hz, 2H), 2.52-2.56 (m, 1H), 2.98 (t, J=12.25 Hz, 2H), 3.34 (dd, J=13.40, 7.72 Hz, 1H), 4.09 (dd, J=2.05, 13.40 Hz, 1H), 4.24 (dt, J=13.24, 4.10 Hz, 2H), 4.32-4.38 (m, 1H), 6.90 (d, J=9.14 Hz, 1H), 7.00 (t, J=7.41 Hz, 1H), 7.12-7.15 (m, 2H), 7.29 (t, J=7.88 Hz, 2H), 7.50 (d, J=8.36 Hz, 2H), 7.52 (d, J=9.30 Hz, 1H), 7.81 (dd, J=2.36, 8.83 Hz, 1H), 8.42 (d, J=2.36 Hz, 1H), 9.15 (s, 1H), 12.53 (br s, 1H); MS (ESI) [M+1]+ 473.

Example C-41

1-(5-(4-(4-chloro-2-fluorophenylcarbamoyl)-2-methyl-3,4-dihydro-2H-benzo[b][1,4]oxazin-7-yl)pyridin-2-yl)piperidine-4-carboxylic acid

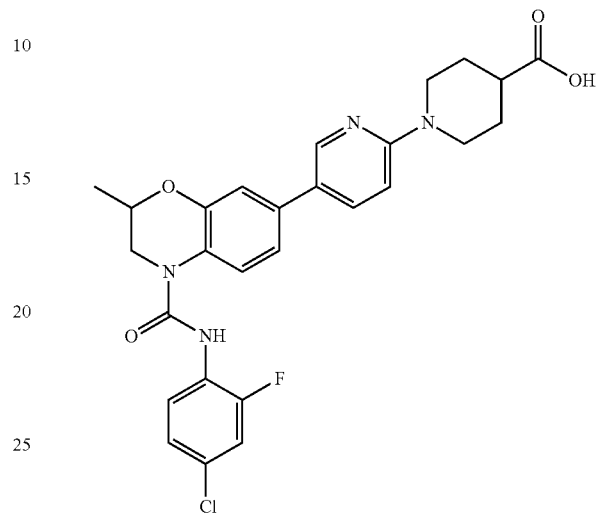

$^1$H NMR (500 MHz, DMSO-d$_6$) δ ppm 1.35 (d, J=6.31 Hz, 3H), 1.54 (dq, J=4.10, 12.45 Hz, 2H), 1.88 (br d, J=13.24 Hz, 2H), 2.52-2.56 (m, 1H), 2.98 (t, J=12.30 Hz, 2H), 3.36 (dd, J=8.20, 14.20 Hz, 1H), 4.10 (br d, J=13.40 Hz, 1H), 4.24 (td, J=3.94, 13.40 Hz, 2H), 4.34-4.40 (m, 1H), 6.90 (d, J=9.14 Hz, 1H), 7.13-7.16 (m, 2H), 7.26 (br d, J=8.51 Hz, 1H), 7.48 (dd, J=2.52, 10.40 Hz, 1H), 7.56 (t, J=8.51 Hz, 1H), 7.61 (d, J=9.30 Hz, 1H), 7.82 (dd, J=2.52, 8.82 Hz, 1H), 8.42 (d, J=2.52 Hz, 1H), 9.14 (s, 1H), 12.44 (br s, 1H); MS (ESI) [M+1]+ 525.

Example C-42

1-(5-(2-ethyl-4-(phenylcarbamoyl)-3,4-dihydro-2H-benzo[b][1,4]oxazin-7-yl)pyrimidin-2-yl)piperidine-4-carboxylic acid

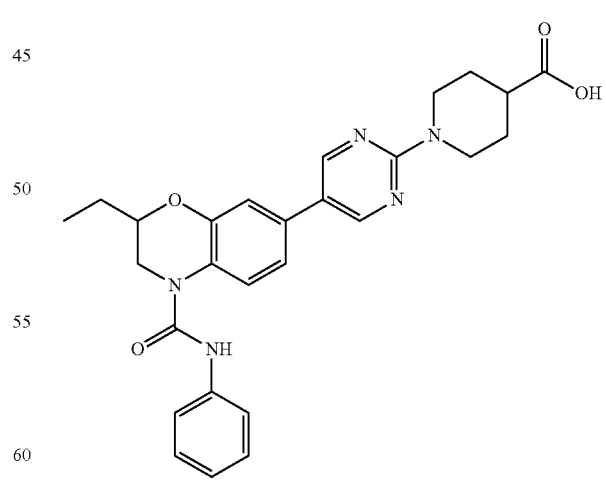

$^1$H NMR (500 MHz, DMSO-d$_6$) δ ppm 1.02 (t, J=7.41 Hz, 3H), 1.50 (dq, J=3.95, 12.14 Hz, 2H), 1.63-1.74 (m, 2H), 1.90 (br d, J=13.40 Hz, 2H), 2.53-2.60 (m, 1H), 3.10 (t, J=12.45 Hz, 2H), 3.46 (dd, J=13.56, 7.57 Hz, 1H), 4.04 (br d, J=2.05, 13.56 Hz, 1H), 4.16 (dq, J=2.05, 6.46 Hz, 1H), 4.56 (dt, J=13.56, 4.22 Hz, 2H), 7.01 (t, J=7.41 Hz, 1H), 7.16 (dd, J=1.73, 8.51 Hz, 1H), 7.18-7.20 (m, 1H), 7.29 (t, J=7.88 Hz, 2H), 7.49 (d, J=8.20 Hz, 2H), 7.52 (d, J=8.36 Hz, 1H), 8.68 (s, 2H), 9.15 (s, 1H), 12.32 (br s, 1H); MS (ESI) [M+1]+ 488.

Example C-43

1-(5-(4-(4-chloro-2-fluorophenylcarbamoyl)-2-ethyl-3,4-dihydro-2H-benzo[b][1,4]oxazin-7-yl)pyrimidin-2-yl)piperidine-4-carboxylic acid

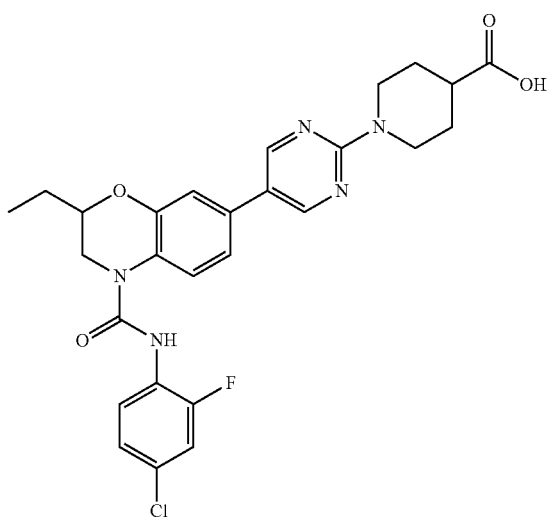 [SMILES: CCC1CN(C(=O)Nc2ccc(Cl)cc2F)c2ccc(-c3cnc(N4CCC(C(=O)O)CC4)nc3)cc2O1]

$^1$H NMR (500 MHz, DMSO-d$_6$) δ ppm 1.02 (t, J=7.41 Hz, 3H), 1.50 (dq, J=4.01, 12.45 Hz, 2H), 1.62-1.75 (m, 2H), 1.89 (dd, J=2.99, 13.08 Hz, 2H), 2.53-2.60 (m, 1H), 3.10 (t, J=12.61 Hz, 2H), 3.47 (dd, J=13.71, 7.41 Hz, 2H), 4.05 (dd, J=2.21, 13.40 Hz, 1H), 4.17 (dq, J=2.36, 6.62 Hz, 1H), 4.55 (dt, J=13.32, 4.06 Hz, 2H), 7.17 (dd, J=1.89, 8.51 Hz, 1H), 7.20 (d, J=1.89 Hz, 1H), 7.26 (br d, J=8.51 Hz, 1H), 7.48 (dd, J=2.52, 10.71 Hz, 1H), 7.55 (t, J=8.67 Hz, 1H), 7.61 (d, J=8.51 Hz, 1H), 8.68 (s, 2H), 8.98 (s, 1H), 12.34 (br s, 1H); MS (ESI) [M+1]+ 540.

Example C-44

2-(1-(5-(2-ethyl-4-(2-ethylphenylcarbamoyl)-3,4-dihydro-2H-benzo[b][1,4]oxazin-7-yl)pyrimidin-2-yl)pyrrolidin-3-yl)acetic acid

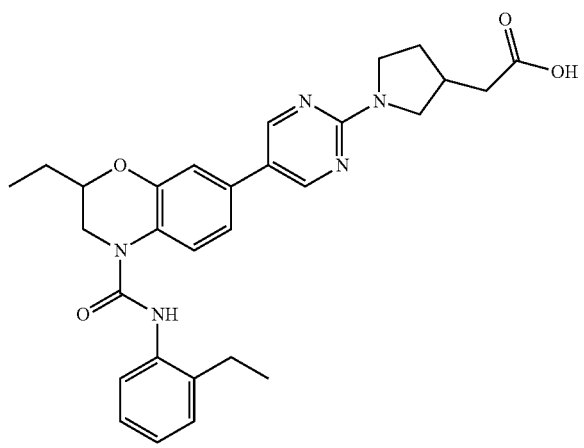 [SMILES: CCc1ccccc1NC(=O)N1CC(CC)Oc2cc(-c3cnc(N4CCC(CC(=O)O)C4)nc3)ccc21]

$^1$H NMR (500 MHz, DMSO-d$_6$) δ ppm 1.04 (t, J=7.41 Hz, 3H), 1.15 (t, J=7.41 Hz, 3H), 1.64-1.76 (m, 3H), 2.12-2.18 (m, 1H), 2.42 (d, J=7.25 Hz, 2H), 2.53-2.62 (m, 1H), 2.59 (q, J=7.41 Hz, 2H), 3.15 (dd, J=7.88, 11.20 Hz, 1H), 3.42-3.51 (m, 2H), 3.63-3.68 (m, 1H), 3.81 (dd, J=7.25, 11.20 Hz, 1H), 4.06 (dd, J=13.56, 2.52 Hz, 1H), 4.17 (br q, J=6.62 Hz, 1H), 7.14-7.20 (m, 4H), 7.24-7.29 (m, 2H), 7.64 (d, J=8.20 Hz, 1H), 8.56 (s, 1H), 8.66 (s, 2H), 12.22 (br s, 1H); MS (ESI) [M+1]+ 516.

Example C-45

2-(1-(5-(4-(4-chloro-2-fluorophenylcarbamoyl)-2-ethyl-3,4-dihydro-2H-benzo[b][1,4]oxazin-7-yl)pyrimidin-2-yl)pyrrolidin-3-yl)acetic acid

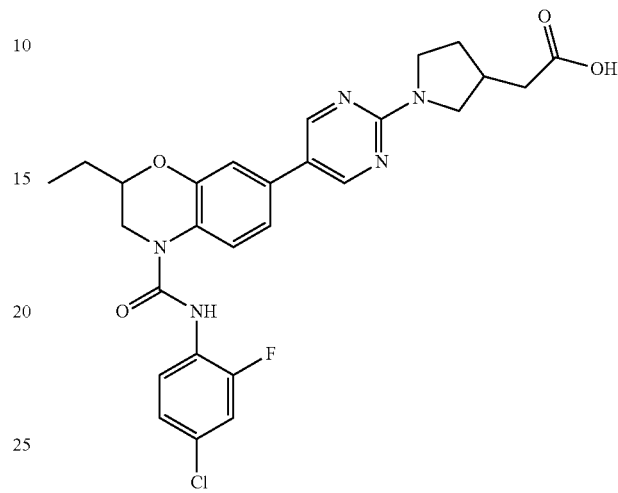

$^1$H NMR (500 MHz, DMSO-d$_6$) δ ppm 1.02 (t, J=7.41 Hz, 3H), 1.63-1.74 (m, 3H), 2.12-2.18 (m, 1H), 2.42 (d, J=7.25 Hz, 2H), 2.54-2.64 (m, 1H), 3.15 (dd, J=11.03, 7.57 Hz, 1H), 3.44-3.50 (m, 2H), 3.63-3.68 (m, 1H), 3.81 (dd, J=11.03, 7.25 Hz, 1H), 4.05 (dd, J=13.56, 2.84 Hz, 1H), 4.17 (dq, J=2.36, 6.78 Hz, 1H), 7.16 (dd, J=1.89, 8.51 Hz, 1H), 7.19 (d, J=1.89 Hz, H), 7.26 (br d, J=8.51 Hz, 1H), 7.48 (dd, J=2.52, 10.51 Hz, 1H), 7.55 (t, J=8.51 Hz, 1H), 7.60 (d, J=8.51 Hz, 1H), 8.66 (s, 2H), 8.97 (s, 1H), 12.22 (br s, 1H); MS (ESI) [M+1]+ 540.

Example C-46

1-(5-(2-ethyl-4-(phenylcarbamoyl)-3,4-dihydro-2H-benzo[b][1,4]oxazin-7-yl)pyridin-2-yl)piperidine-4-carboxylic acid

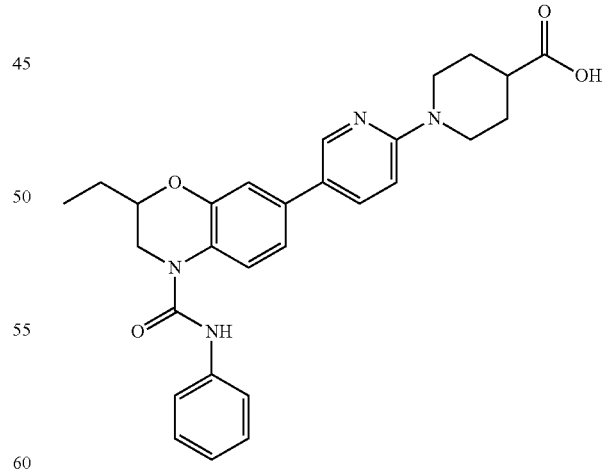

$^1$H NMR (500 MHz, DMSO-d$_6$) δ ppm 1.02 (t, J=7.41 Hz, 3H), 1.54 (dq, J=3.48, 12.30 Hz, 2H), 1.63-1.74 (m, 2H), 1.87 (br d, J=12.30 Hz, 2H), 2.47 (br s, 1H), 2.97 (t, J=12.29 Hz, 2H), 3.46 (dd, J=13.40, 7.09 Hz, 1H), 4.03 (dd, J=2.05, 13.40 Hz, 1H), 4.16 (br q, J=6.62 Hz, 1H), 4.24 (dt, J=13.30, 4.05 Hz, 2H), 6.90 (d, J=8.83 Hz, 1H), 7.00 (dt, J=0.95, 7.57 Hz, 1H), 7.12-7.15 (m, 2H), 7.29 (t, J=7.88 Hz, 2H), 7.49 (d, J=8.04 Hz, 2H), 7.50 (d, J=8.99 Hz, 1H), 7.82 (dd, J=2.52, 8.99 Hz, 1H), 8.42 (d, J=2.84 Hz, 1H), 9.13 (s, 1H), 12.37 (br s, 1H); MS (ESI) [M+1]+ 487.

Example C-47 methyl 1-(5-(2-ethyl-4-(phenylcarbamoyl)-3,4-dihydro-2H-benzo[b][1,4]oxazin-7-yl)pyridin-2-yl)piperidine-4-carboxylate

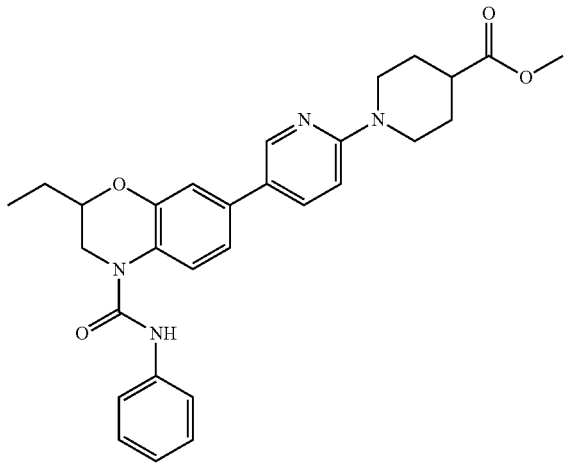 [SMILES: CCC1CN(C(=O)Nc2ccccc2)c2ccc(-c3ccc(N4CCC(C(=O)OC)CC4)nc3)cc2O1]

1H NMR (500 MHz, DMSO-d6) δ ppm 1.02 (t, J=7.41 Hz, 3H), 1.56 (br q, J=12.14 Hz, 2H), 1.62-1.73 (m, 2H), 1.89 (br d, J=12.93 Hz, 2H), 2.61-2.70 (m, 1H), 2.99 (t, J=12.30 Hz, 2H), 3.46 (dd, J=13.71, 7.09 Hz, 1H), 3.63 (s, 3H), 4.03 (br d, J=13.40 Hz, 1H), 4.16 (br q, J=6.70 Hz, 1H), 4.22-4.27 (m, 2H), 6.90 (d, J=9.14 Hz, 1H), 7.00 (t, J=7.41 Hz, 1H), 7.13 (d, J=7.10 Hz, 1H), 7.14 (s, 1H), 7.29 (t, J=7.41 Hz, 2H), 7.48-7.52 (m, 3H), 7.82 (dd, J=2.52, 8.67 Hz, 1H), 8.43 (d, J=2.36 Hz, 1H), 9.13 (s, 1H); MS (ESI) [M+1]+ 501.

Example C-48

1-(5-(2-methyl-4-(phenylcarbamoyl)-3,4-dihydro-2H-benzo[b][1,4]oxazin-7-yl)pyridin-2-yl)pyrrolidine-3-carboxylic acid

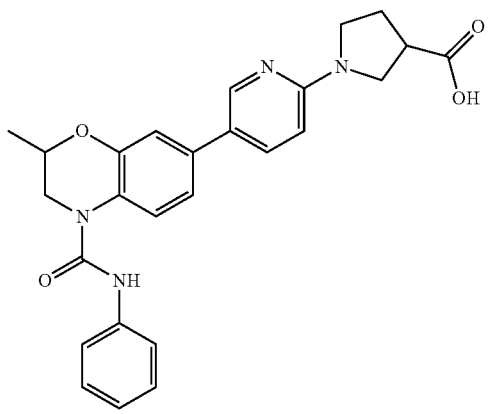 [SMILES: CC1CN(C(=O)Nc2ccccc2)c2ccc(-c3ccc(N4CCC(C(=O)O)C4)nc3)cc2O1]

1H NMR (500 MHz, DMSO-d6) δ ppm 1.35 (d, J=6.31 Hz, 3H), 2.15-2.30 (m, 2H), 3.22-3.28 (m, 1H), 3.35 (dd, J=7.88, 13.57 Hz, 1H), 3.43-3.57 (m, 2H), 3.64-3.73 (m, 2H), 4.11 (dd, J=2.36, 13.57 Hz, 1H), 4.32-4.38 (m, 1H), 6.76 (br s, 1H), 7.01 (t, J=7.41 Hz, 1H), 7.14-7.20 (m, 2H), 7.29 (t, J=7.88 Hz, 2H), 7.50 (d, J=8.20 Hz, 2H), 7.55 (d, J=8.36 Hz, 1H), 8.00 (br s, 1H), 8.33 (s, 1H), 9.16 (s, 1H), 12.63 (br s, 1H); MS (ESI) [M+1]+ 459.

Example C-49 methyl 1-(5-(2-methyl-4-(phenylcarbamoyl)-3,4-dihydro-2H-benzo[b][1,4]oxazin-7-yl)pyridin-2-yl)pyrrolidine-3-carboxylate

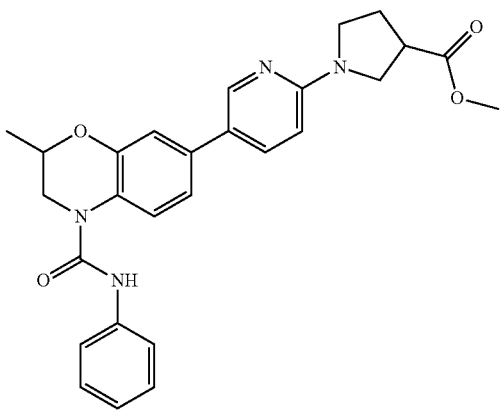

1H NMR (500 MHz, DMSO-d6) δ ppm 1.35 (d, J=6.31 Hz, 3H), 2.15-2.21 (m, 1H), 2.22-2.29 (m, 1H), 3.28-3.32 (m, 2H), 3.42-3.54 (m, 2H), 3.61 (dd, J=6.31, 10.72; H, 1H), 3.66 (s, 3H), 3.69 (dd, J=8.20, 10.72 Hz, 1H), 4.09 (dd, J=1.89, 13.57 Hz, 1H), 4.33-4.38 (m, 1H), 6.54 (d, J=8.83 Hz, 1H), 7.00 (t, J=7.41 Hz, 1H), 7.11 (s, 1H), 7.12 (d, J=7.57 Hz, 1H), 7.29 (t, J=7.72 Hz, 2H), 7.48-7.53 (m, 3H), 7.81 (dd, J=2.36, 8.99 Hz, 1H), 8.40 (d, J=2.36 Hz, 1H), 9.13 (s, 1H); MS (ESI) [M+1]+ 473.

Example C-50

2-(1-(5-(2-methyl-4-(phenylcarbamoyl)-3,4-dihydro-2H-benzo[b][1,4]oxazin-7-yl)pyridin-2-yl)pyrrolidin-3-yl)acetic acid

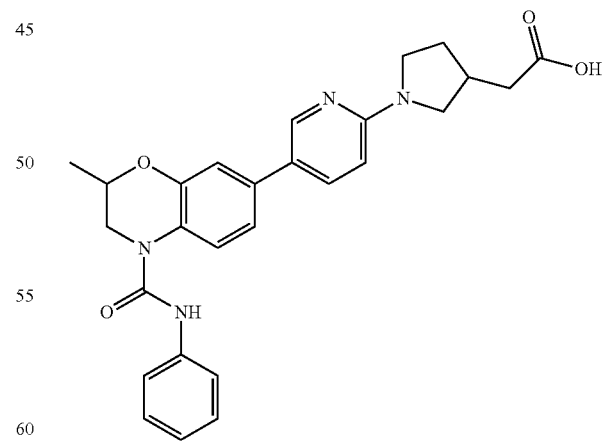

1H NMR (500 MHz, DMSO-d6) δ ppm 1.35 (d, J=6.31 Hz, 3H), 1.69-1.74 (m, 1H), 2.15-2.21 (m, 1H), 2.44 (d, J=7.25 Hz, 2H), 2.56-2.65 (m, 1H), 3.12-3.16 (m, 1H), 3.36-3.48 (m, 2H), 3.54-3.62 (m, 1H), 3.73 (t, J=9.77 Hz, 1H), 4.11 (br d, J=13.40 Hz, 1H), 4.33-4.38 (m, 1H), 6.58-6.79 (br s, 1H), 7.00 (t, J=7.41 Hz, 1H), 7.14-7.18 (m, 2H), 7.29 (t, J=7.72 Hz, 2H), 7.50 (d, J=8.51 Hz, 2H), 7.55 (d, J=8.51 Hz, 1H), 7.88-8.09 (br s, 1H), 8.31 (s, 1H), 9.15 (s, 1H), 12.26 (br s, 1H); MS (ESI) [M+1]⁺ 473.

Example C-51

2-(1-(5-(4-(2-ethylphenylcarbamoyl)-2-methyl-3,4-dihydro-2H-benzo[b][1,4]oxazin-7-yl)pyridin-2-yl)pyrrolidin-3-yl)acetic acid

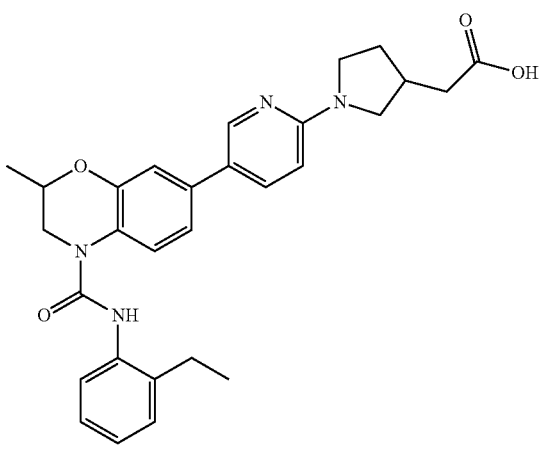 [SMILES: CCc1ccccc1NC(=O)N1CC(C)Oc2cc(-c3ccc(N4CCC(CC(=O)O)C4)nc3)ccc21]

¹H NMR (500 MHz, DMSO-d₆) δ ppm 1.16 (t, J=7.57 Hz, 3H), 1.36 (d, J=6.31 Hz, 3H), 1.64-1.74 (m, 1H), 2.13-2.19 (m, 1H), 2.42 (d, J=7.25 Hz, 2H), 2.55-2.65 (m, 1H), 2.60 (q, J=7.57 Hz, 2H), 3.07 (dd, J=10.40, 7.57 Hz, 1H), 3.36-3.43 (m, 2H), 3.50-3.56 (m, 1H), 3.69 (dd, J=10.40, 7.25 Hz, 1H), 4.09 (dd, J=2.52, 11.35 Hz, 1H), 4.35-4.40 (m, 1H), 6.48 (d, J=9.14 Hz, 1H), 7.09-7.20 (m, 4H), 7.25 (dd, J=2.05, 7.10 Hz, 1H), 7.29 (dd, J=1.75, 7.41 Hz, 1H), 7.63 (d, J=8.36 Hz, 1H), 7.77-7.81 (m, 1H), 8.37 (d, J=2.52 Hz, 1H), 8.52 (s, 1H), 12.21 (br s, 1H); MS (ESI) [M+1]⁺ 501.

Example C-52

2-(1-(5-(4-(4-chloro-2-fluorophenylcarbamoyl)-2-methyl-3,4-dihydro-2H-benzo[b][1,4]oxazin-7-yl)pyridin-2-yl)pyrrolidin-3-yl)acetic acid

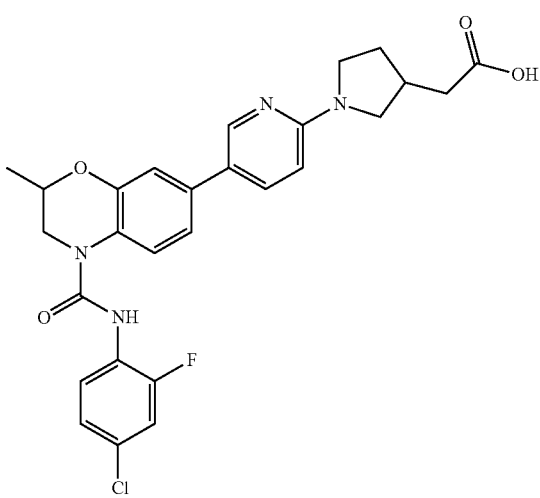 [SMILES: CC1CN(C(=O)Nc2ccc(Cl)cc2F)c2ccc(-c3ccc(N4CCC(CC(=O)O)C4)nc3)cc2O1]

¹H NMR (500 MHz, DMSO-d₆) δ ppm 1.35 (d, J=6.31 Hz, 3H), 1.64-1.72 (m, 1H), 2.13-2.19 (m, 1H), 2.42 (d, J=7.57 Hz, 2H), 2.52-2.65 (m, 1H), 3.06 (dd, J=10.72, 7.57 Hz, 1H), 3.35-3.40 (m, 2H), 3.50-3.55 (m, 1H), 3.69 (dd, J=7.57, 10.25 Hz, 1H), 4.10 (dd, J=2.05, 13.40 Hz, 1H), 4.34-4.39 (m, 1H), 6.48 (d, J=9.14 Hz, 1H), 7.12 (s, 1H), 7.13 (br d, J=10.50 Hz, 1H), 7.26 (br d, J=8.51 Hz, 1H), 7.48 (dd, J=2.52, 10.56 Hz, 1H), 7.56 (t, J=8.51 Hz, 1H), 7.59 (d, J=8.20 Hz, 1H), 7.79 (dd, J=8.67, 2.68 Hz, 1H), 8.38 (d, J=2.52 Hz, 1H), 8.94 (s, 1H), 12.31 (br s, 1H); MS (ESI) [M+1]⁺ 525.

Example C-53 methyl 2-(1-(5-(4-(4-chloro-2-fluorophenylcarbamoyl)-2-methyl-3,4-dihydro-2H-benzo[b][1,4]oxazin-7-yl)pyridin-2-yl)pyrrolidin-3-yl)acetate

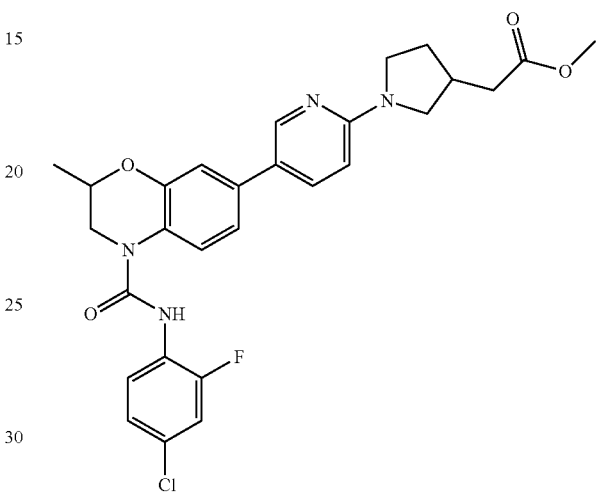

¹H NMR (500 MHz, DMSO-d₆) δ ppm 1.35 (d, J=6.31 Hz, 3H), 1.64-1.74 (m, 1H), 2.12-2.20 (m, 1H), 2.52 (d, J=7.50 Hz, 2H), 2.57-2.66 (m, 1H), 3.07 (dd, J=8.36, 10.24 Hz, 1H), 3.35-3.40 (m, 2H), 3.50-3.57 (m, 1H), 3.64 (s, 3H), 3.69 (dd, J=7.57, 10.25 Hz, 1H), 4.10 (J=2.10, 13.35 Hz, 1H), 4.33-4.40 (m, 1H), 6.49 (d, J=8.67 Hz, 1H), 7.12 (s, 1H), 7.13 (br d, J=10.35 Hz, 1H), 7.26 (br d, J=8.99 Hz, 1H), 7.47 (dd, J=2.05, 10.50 Hz, 1H), 7.56 (t, J=8.51 Hz, 1H), 7.59 (d, J=8.20 Hz, 1H), 7.79 (br d, J=8.67 Hz, 1H), 8.38 (d, J=2.52 Hz, 1H), 8.94 (s, 1H); MS (ESI) [M+1]⁺ 539.

Example C-54

2,2-dimethyl-3-(5-(4-(phenylcarbamoyl)-2-propyl-3,4-dihydro-2H-benzo[b][1,4]oxazin-7-yl)pyridin-2-yloxy)propanoic acid

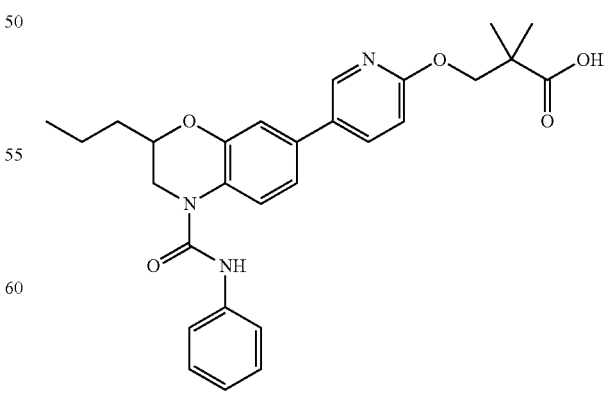

¹H NMR (500 MHz, DMSO-d₆) δ ppm 0.95 (t, J=7.25 Hz, 3H), 1.23 (s, 6H), 1.42-1.72 (m, 4H), 3.47 (dd, J=13.24, 7.25

Hz, 1H), 4.03 (br d, J=13.08 Hz, 1H), 4.21-4.27 (m, 1H), 4.28 (s, 2H), 6.86 (d, J=8.51 Hz, 1H), 7.01 (t, J=7.41 Hz, 1H), 7.18 (d, J=12.15 Hz, 1H), 7.19 (s, 1H), 7.29 (t, J=7.88 Hz, 2H), 7.49 (d, J=8.51 Hz, 2H), 7.55 (d, J=8.51 Hz, 1H), 7.99 (dd, J=2.52, 8.67 Hz, 1H), 8.44 (d, J=2.52 Hz, 1H), 9.16 (s, 1H), 12.37 (br s, 1H); MS (ESI) [M+1]$^+$ 490.

Example C-55

3-(5-(2-ethyl-4-(phenethylcarbamoyl)-3,4-dihydro-2H-benzo[b][1,4]oxazin-7-yl)pyridin-2-yloxy)-2,2-dimethylpropanoic acid

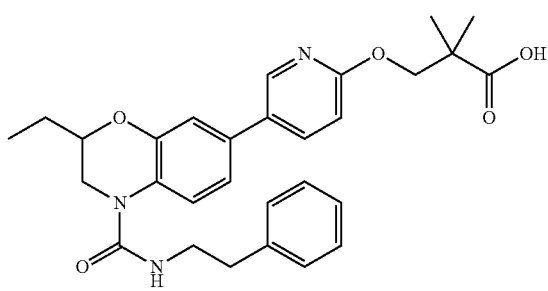 [SMILES: CCC1CN(C(=O)NCCc2ccccc2)c2ccc(-c3ccc(OCC(C)(C)C(=O)O)nc3)cc2O1]

$^1$H NMR (500 MHz, DMSO-d$_6$) δ ppm 0.99 (t, J=7.57 Hz, 3H), 1.23 (s, 6H), 1.54-1.67 (m, 2H), 2.80 (t, J=7.41 Hz, 2H), 3.25 (dd, J=13.56, 7.57 Hz, 1H), 3.36-3.44 (m, 2H), 3.92 (br d, J=13.56 Hz, 1H), 3.97-4.02 (m, 1H), 4.28 (s, 2H), 6.85 (d, J=8.51 Hz, 1H), 7.03 (t, J=5.35 Hz, 1H), 7.10 (dd, J=1.89, 8.36 Hz, 1H), 7.14 (d, J=1.89 Hz, 1H), 7.20-7.25 (m, 3H), 7.32 (t, J=7.57 Hz, 2H), 7.48 (d, J=8.20 Hz, 1H), 7.97 (dd, J=2.36, 8.67 Hz, 1H), 8.42 (d, J=2.36 Hz, 1H), 12.36 (s, 1H); MS (ESI) [M+1]$^+$ 504.

Example C-56

(R)-3-(5-(4-(4-chloro-2-fluorophenylcarbamoyl)-2-methyl-3,4-dihydro-2H-benzo[b][1,4]oxazin-7-yl)pyridin-2-yloxy)-2,2-dimethylpropanoic acid

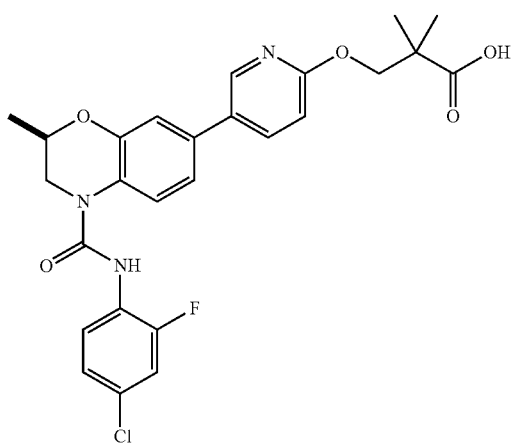 [SMILES: C[C@@H]1CN(C(=O)Nc2ccc(Cl)cc2F)c2ccc(-c3ccc(OCC(C)(C)C(=O)O)nc3)cc2O1]

$^1$H NMR (500 MHz, DMSO-d$_6$) δ ppm 1.22 (s, 6H), 1.35 (d, J=6.31 Hz, 3H), 3.38 (dd, J=13.56, 7.57 Hz, 1H), 4.11 (br d, J=13.40 Hz, 1H), 4.28 (s, 2H), 4.35-4.41 (m, 1H), 6.86 (d, J=8.83 Hz, 1H), 7.19 (d, J=11.35 Hz, 1H), 7.20 (s, 1H), 7.26 (d, J=8.83 Hz, 1H), 7.48 (d, J=10.25 Hz, 1H), 7.56 (t, J=8.67 Hz, 1H), 7.65 (d, J=8.51 Hz, 1H), 7.99 (d, J=1.89, 8.67 Hz, 1H), 8.44 (s, 1H), 9.01 (s, 1H), 12.37 (br s, 1H); MS (ESI) [M+1]$^+$ 514.

Example C-57

3-(5-(2-ethyl-4-(3-phenylpropylcarbamoyl)-3,4-dihydro-2H-benzo[b][1,4]oxazin-7-yl)pyridin-2-yloxy)-2,2-dimethylpropanoic acid

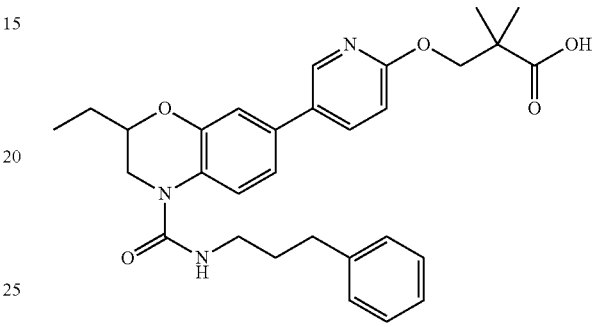

$^1$H NMR (500 MHz, DMSO-d$_6$) δ ppm 1.00 (t, J=7.41 Hz, 3H), 1.23 (s, 6H), 1.58-1.70 (m, 2H), 1.76-1.82 (m, 2H), 2.60 (q, J=7.41 Hz, 2H), 3.11-3.18 (m, 2H), 3.30-3.35 (m, 1H), 3.93 (dd, J=2.52, 13.40 Hz, 1H), 4.01-4.07 (m, 1H), 4.27 (s, 2H), 6.85 (d, J=8.67 Hz, 1H), 7.01 (t, J=5.40 Hz, 1H), 7.13-7.20 (m, 3H), 7.20-7.26 (m, 2H), 7.29 (t, J=7.41 Hz, 2H), 7.61 (d, J=8.99 Hz, 1H), 7.97 (dd, J=2.52, 8.51 Hz, 1H), 8.42 (d, J=2.52 Hz, 1H), 12.37 (br s, 1H); MS (ESI) [M+1]$^+$ 518.

Example C-58

3-(5-(2-ethyl-4-(4-phenylbutylcarbamoyl)-3,4-dihydro-2H-benzo[b][1,4]oxazin-7-yl)pyridin-2-yloxy)-2,2-dimethylpropanoic acid

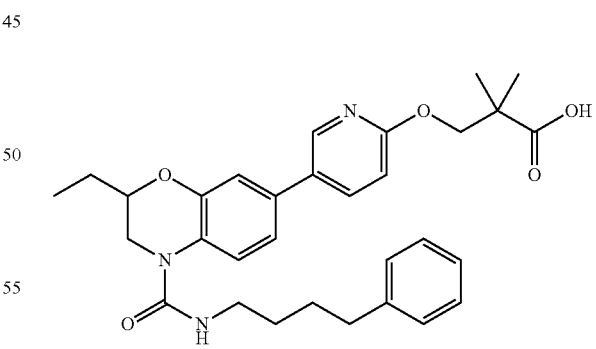

$^1$H NMR (500 MHz, DMSO-d$_6$) δ ppm 0.99 (t, J=7.41 Hz, 3H), 1.23 (s, 6H), 1.47-1.54 (m, 2H), 1.55-1.69 (m, 4H), 2.60 (t, J=7.57 Hz, 2H), 3.11-3.18 (m, 2H), 3.31 (dd, J=7.41, 13.57 Hz, 1H), 3.92 (br d, J=13.24 Hz, 1H), 4.00-4.05 (m, 1H), 4.28 (s, 2H), 6.85 (d, J=8.51 Hz, 1H), 6.99 (t, J=5.36 Hz, 1H), 7.11-7.23 (m, 5H), 7.28 (t, J=7.57 Hz, 2H), 7.59 (d, J=8.83 Hz, 1H), 7.96 (dd, J=2.21, 8.51 Hz, 1H), 8.42 (d, J=1.89 Hz, 1H), 12.40 (br s, 1H); MS (ESI) [M+1]$^+$ 532.

Example C-59

2-methyl-2-(4-(2-methyl-4-(phenylcarbamoyl)quinolin-7-yl)phenoxy)propanoic acid

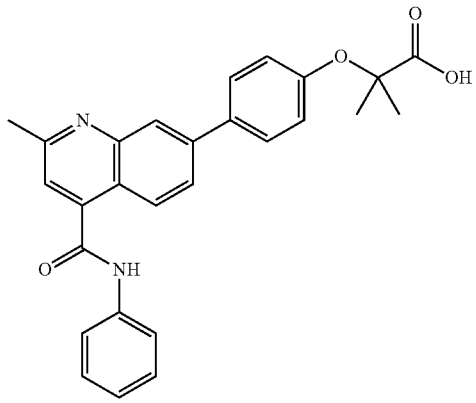 [SMILES: Cc1cc(C(=O)Nc2ccccc2)c2ccc(-c3ccc(OC(C)(C)C(=O)O)cc3)cc2n1]

$^1$H NMR (500 MHz, DMSO-d$_6$) δ ppm 1.58 (s, 6H), 2.81 (s, 3H), 6.99 (d, J=8.5 Hz, 2H), 7.19 (t, J=7.5 Hz, 1H), 7.42 (d, J=7.5 Hz, 2H), 7.77 (s, 1H), 7.81 (t, J=8.5 Hz, 3H), 8.12 (d, J=9.0 Hz, 1H), 8.19 (d, J=8.5 Hz, 1H), 8.27 (s, 1H), 10.88 (br s, 1H); MS (ESI) [M+1]$^+$ 441.

Example C-60

2,2-dimethyl-3-(5-(2-methyl-4-(2-propylphenylcarbamoyl) quinolin-7-yl)pyridin-2-yloxy)propanoic acid

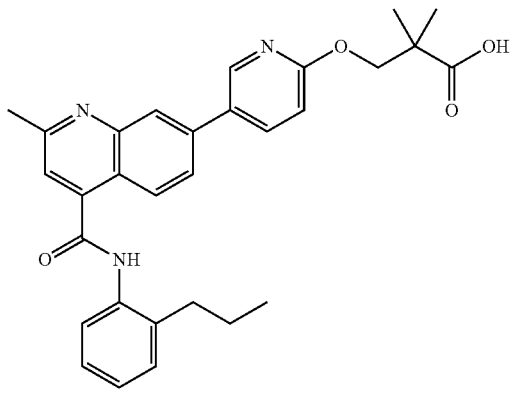 [SMILES: CCCc1ccccc1NC(=O)c1cc(C)nc2cc(-c3ccc(OCC(C)(C)C(=O)O)nc3)ccc12]

$^1$H NMR (500 MHz, DMSO-d$_6$) δ ppm 0.94 (t, J=7.5 Hz, 1H), 1.10 (s, 9H), 1.63 (m, 1H), 2.67 (t, J=7.5 Hz, 1H), 2.76 (s, 3H), 3.17 (s, 1H), 4.28 (s, 2H), 6.89 (d, J=9.0 Hz, 1H), 7.26-7.33 (m, 2H), 7.49 (d, J=8.5 Hz, 1H), 7.61 (s, 1H), 7.98 (d, J=9.0 Hz, 1H), 8.21 (t, J=8.5 Hz, 1H), 8.28 (s, 1H), 8.51 (s, 2H), 8.67 (m, 1H), 10.37 (br s, 1H); MS (ESI) [M+1]$^+$ 498.

Example C-61 ethyl 4-(4-(4-(phenylcarbamoyl)-3,4-dihydro-2H-benzo[b][1,4]oxazin-7-yl)phenoxy)cyclohexanecarboxylate

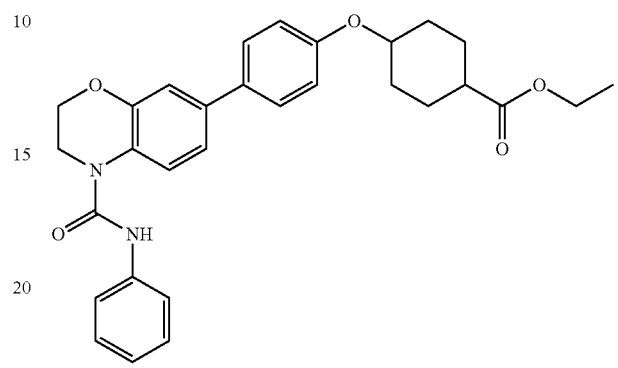

$^1$H NMR (500 MHz, CHLOROFORM-d) (isomer A) δ ppm 1.30 (t, J=7.50 Hz, 3H), 1.50-1.68 (m, 4H), 2.11-2.15 (m, 2H), 2.24-2.27 (m, 2H), 2.36-2.41 (m, 1H), 4.01 (t, J=4.50 Hz, 2H), 4.17 (q, J=7.50 Hz, 2H), 4.25-4.31 (m, 1H), 4.38 (t, J=4.50 Hz, 2H), 6.34 (br s, 1H), 6.99 (d, J=9.00 Hz, 2H), 7.11 (t, J=7.00 Hz, 1H), 7.16-7.18 (m, 1H), 7.21 (d, J=2.00 Hz, 1H), 7.35 (t, J=8.00 Hz, 2H), 7.39 (d, J=8.00 Hz, 1H), 7.43-7.45 (m, 2H), 7.52 (d, J=9.00 Hz, 2H); MS (ESI) [M+1]$^+$ 501.

Example C-62

(1r,4r)-ethyl 4-(5-(4-(phenylcarbamoyl)-3,4-dihydro-2H-benzo[b][1,4]oxazin-7-yl)pyridin-2-yloxy)cyclohexanecarboxylate

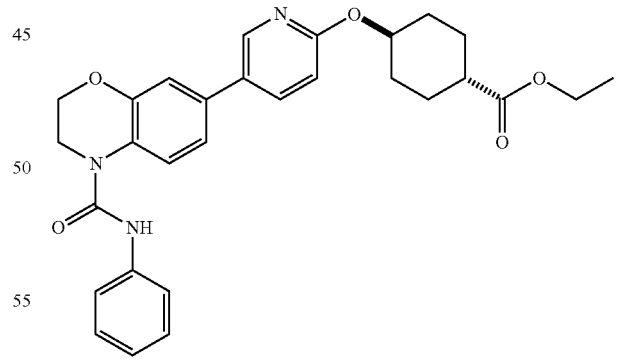

$^1$H NMR (500 MHz, CHLOROFORM-d) δ ppm 1.29 (t, J=7.00 Hz, 3H), 1.52-1.60 (m, 2H), 1.69-1.77 (m, 2H), 2.11-2.14 (m, 2H), 2.27-2.30 (m, 2H), 2.36-2.39 (m, 1H), 4.01 (t, J=4.50 Hz, 2H), 4.17 (q, J=7.00 Hz, 2H), 4.38 (t, J=4.50 Hz, 2H), 5.09-5.15 (m, 1H), 6.85 (d, J=8.50 Hz, 1H), 7.10-7.13 (m, 2H), 7.18 (d, J=1.50 Hz, 1H), 7.24 (br s, 1H), 7.35 (t, J=8.00 Hz, 2H), 7.43-7.45 (m, 3H), 7.86 (d, J=8.50 Hz, 1H), 8.41 (s, 1H); MS (ESI) [M+1]$^+$ 502.

Example C-63

4-(4-(4-(phenylcarbamoyl)-3,4-dihydro-2H-benzo[b][1,4]oxazin-7-yl)phenoxy)cyclohexanecarboxylic acid

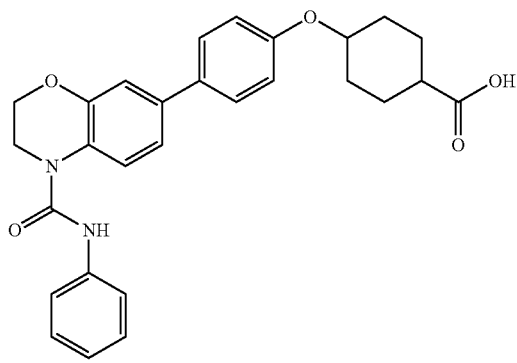

$^1$H NMR (500 MHz, CHLOROFORM-d) (isomer A) δ ppm 1.54-1.72 (m, 4H), 2.17-2.28 (m, 4H), 2.45-2.50 (m, 1H), 4.01 (t, J=4.50 Hz, 2H), 4.27-4.32 (m, 1H), 4.38 (t, J=4.50 Hz, 2H), 6.99 (d, J=8.50 Hz, 2H), 7.11 (t, J=7.50 Hz, 1H), 7.16-7.18 (m, 1H), 7.21 (d, J=2.00 Hz, 1H), 7.35 (t, J=7.50 Hz, 2H), 7.39 (d, J=8.00 Hz, 1H), 7.43-7.45 (m, 2H), 7.52 (d, J=8.50 Hz, 2H); MS (ESI) [M+1]$^+$ 473.

Example C-64

(1r,4r)-4-(5-(4-(phenylcarbamoyl)-3,4-dihydro-2H-benzo[b][1,4]oxazin-7-yl)pyridin-2-yloxy)cyclohexanecarboxylic acid

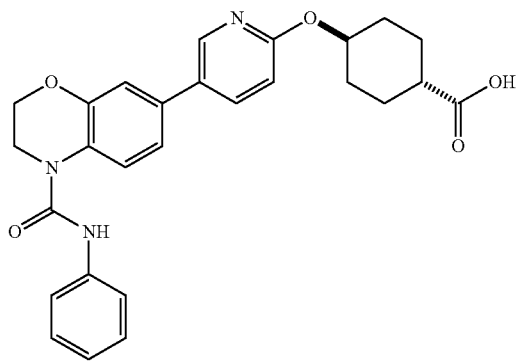

$^1$H NMR (500 MHz, CHLOROFORM-d) δ ppm 1.52-1.78 (m, 4H), 2.16-2.31 (m, 4H), 2.43-2.48 (m, 1H), 4.02 (t, J=4.50 Hz, 2H), 4.38 (t, J=4.50 Hz, 2H), 5.06-5.12 (m, 1H), 6.79 (d, J=8.50 Hz, 1H), 7.10-7.15 (m, 2H), 7.18 (d, J=2.00 Hz, 1H), 7.25 (br s, 1H), 7.35 (t, J=7.50 Hz, 2H), 7.42-7.45 (m, 3H), 7.79 (dd, J=2.50, 8.50 Hz, 1H), 8.38 (d, J=2.50 Hz, 1H); MS (ESI) [M+1]$^+$ 474.

Example C-65

4-(5-(4-(phenylcarbamoyl)-3,4-dihydro-2H-benzo[b][1,4]oxazin-7-yl)pyridin-2-yloxy)cyclohexanecarboxylic acid

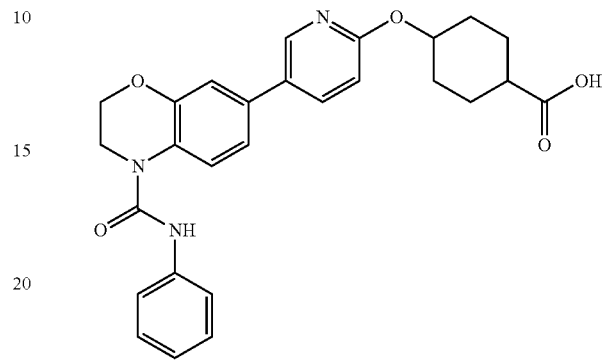

$^1$H NMR (500 MHz, DMSO-d$_6$) (major isomer described) δ ppm 1.41-1.53 (m, 4H), 1.96-2.13 (m, 4H), 2.25-2.28 (m, 1H), 3.87 (t, J=4.50 Hz, 2H), 4.30 (t, J=4.50 Hz, 2H), 4.94-4.98 (m, 1H), 6.81 (d, J=9.00 Hz, 1H), 7.00 (t, J=7.00 Hz, 1H), 7.17-7.19 (m, 2H), 7.29 (t, J=7.50 Hz, 2H), 7.50 (d, J=8.00 Hz, 2H), 7.59 (d, J=8.50 Hz, 1H), 7.95-7.97 (m, 1H), 8.45 (d, J=2.50 Hz, 1H), 9.17 (s, 1H), 12.21 (br s, 1H); MS (ESI) [M+1]$^+$ 474.

Example C-66

2-methyl-2-(5-(4-(phenylcarbamoyl)-3,4-dihydro-2H-benzo[b][1,4]oxazin-7-yl)pyridin-2-yloxy)propanoic acid

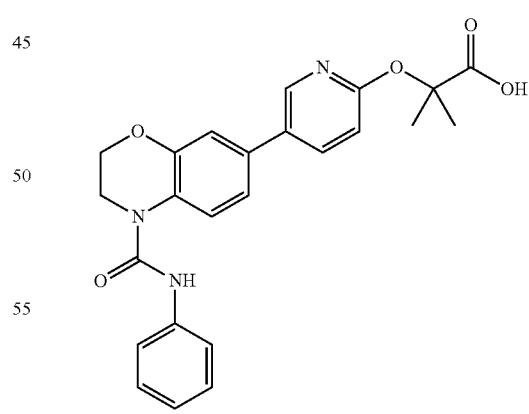

$^1$H NMR (500 MHz, DMSO-d$_6$) δ ppm 1.61 (s, 6H), 3.87 (t, J=4.50 Hz, 2H), 4.30 (t, J=4.50 Hz, 2H), 6.85 (d, J=8.50 Hz, 1H), 6.99-7.03 (m, 1H), 7.17-7.19 (m, 2H), 7.29 (t, J=8.50 Hz, 2H), 7.50 (d, J=8.50 Hz, 2H), 7.59 (d, J=8.50 Hz, 1H), 7.97 (dd, J=2.00, 8.50 Hz, 1H), 8.34 (d, J=2.50 Hz, 1H), 9.18 (s, 1H), 12.53 (br s, 1H); MS (ESI) [M+1]$^+$ 434.

Example C-67 ethyl 2-methyl-2-(5-(4-(phenylcarbamoyl)-3,4-dihydro-2H-benzo[b][1,4]oxazin-7-yl)pyridin-2-yloxy)propanoate

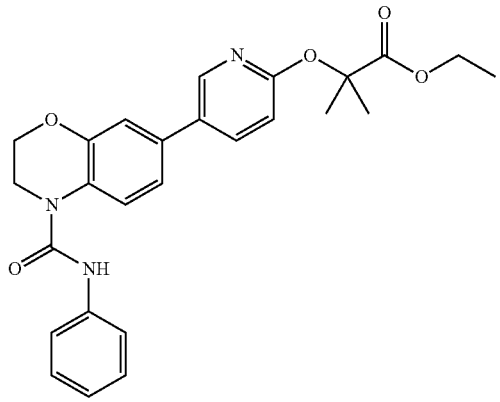 [SMILES: CCOC(=O)C(C)(C)Oc1ccc(-c2ccc3c(c2)OCCN3C(=O)Nc2ccccc2)cn1]

¹H NMR (500 MHz, DMSO-d₆) δ ppm 1.50 (t, J=7.00 Hz, 3H), 1.62 (s, 6H), 3.87 (t, J=4.50 Hz, 2H), 4.08 (q, J=7.00 Hz, 2H), 4.30 (t, J=4.50 Hz, 2H), 6.87 (d, J=9.00 Hz, 1H), 7.01 (t, J=7.50 Hz, 1H), 7.17-7.19 (m, 2H), 7.29 (t, J=7.50 Hz, 2H), 7.50 (d, J=8.50 Hz, 2H), 7.59 (d, J=8.50 Hz, 1H), 7.98-8.00 (m, 1H), 8.33-8.34 (m, 1H), 9.17 (s, 1H); MS (ESI) [M+1]⁺ 462.

Example C-68

4-(5-(2-methyl-4-(phenylcarbamoyl)-3,4-dihydro-2H-benzo[b][1,4]oxazin-7-yl)pyridin-2-yloxy)cyclohexanecarboxylic acid

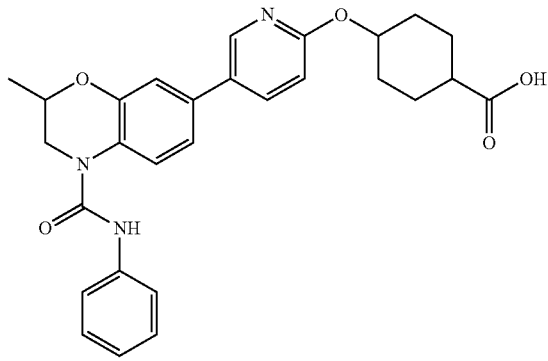 [SMILES: CC1CN(C(=O)Nc2ccccc2)c2ccc(-c3ccc(OC4CCC(C(=O)O)CC4)nc3)cc2O1]

¹H NMR (500 MHz, DMSO-d₆) (major isomer described) δ ppm 1.35 (d, J=6.50 Hz, 3H), 1.41-1.53 (m, 4H), 1.97-2.13 (m, 4H), 2.25-2.30 (m, 1H), 3.32-3.38 (m, 1H), 4.10 (d, J=12.50 Hz, 1H), 4.33-4.39 (m, 1H), 4.94-4.99 (m, 1H), 6.81 (d, J=8.50 Hz, 1H), 7.01 (dt, J=0.50, 7.50 Hz, 1H), 7.16-7.18 (m, 2H), 7.29 (t, J=7.50 Hz, 2H), 7.50 (d, J=8.50 Hz, 2H), 7.56 (d, J=8.50 Hz, 1H), 7.97 (d, J=8.50 Hz, 1H), 8.44 (d, J=2.50 Hz, 1H), 9.18 (s, 1H), 12.16 (br s, 1H); MS (ESI) [M+1]⁺ 488.

Example C-69

(1s,4s)-4-(5-(4-(phenylcarbamoyl)-3,4-dihydro-2H-benzo[b][1,4]oxazin-7-yl)pyridin-2-yloxy)cyclohexanecarboxylic acid

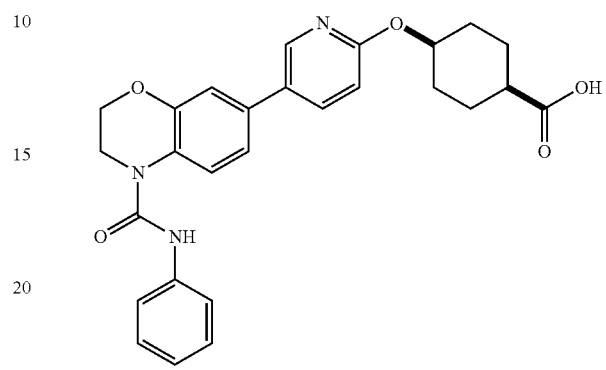

¹H NMR (500 MHz, DMSO-d₆) δ ppm 1.65-1.74 (m, 4H), 1.78-1.87 (m, 4H), 2.32-2.40 (m, 1H), 3.88 (t, J=4.00 Hz, 2H), 4.30 (t, J=4.00 Hz, 2H), 5.18-5.20 (m, 1H), 6.85 (d, J=8.50 Hz, 1H), 7.01 (t, J=7.00 Hz, 1H), 7.16-7.19 (m, 2H), 7.29 (t, J=8.00 Hz, 2H), 7.50 (d, J=8.00 Hz, 2H), 7.59 (d, J=8.50 Hz, 1H), 7.96 (dd, J=1.50, 8.50 Hz, 1H), 8.43 (d, J=2.00 Hz, 1H), 9.17 (s, 1H); MS (ESI) [M+1]⁺ 474.

Example C-70

4-(5-(2-ethyl-4-(phenylcarbamoyl)-3,4-dihydro-2H-benzo[b][1,4]oxazin-7-yl)pyridin-2-yloxy)cyclohexanecarboxylic acid (isomer A)

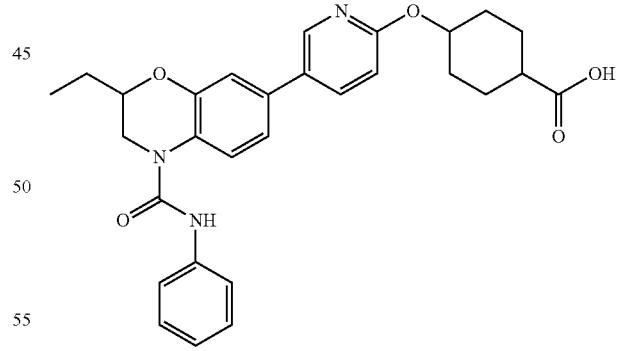

¹H NMR (500 MHz, DMSO-d₆) δ ppm 1.02 (t, J=7.50 Hz, 3H), 1.65-1.75 (m, 6H), 1.78-1.87 (m, 4H), 2.37-2.43 (m, 1H), 3.45-3.49 (m, 1H), 4.03-4.05 (m, 1H), 4.14-4.19 (m, 1H), 5.16-5.21 (m, 1H), 6.85 (d, J=9.00 Hz, 1H), 7.01 (dt, J=1.00, 7.50 Hz, 1H), 7.16-7.19 (m, 2H), 7.29 (t, J=7.50 Hz, 2H), 7.49 (d, J=8.50 Hz, 2H), 7.54 (d, J=8.00 Hz, 1H), 7.97 (dd, J=1.50, 8.50 Hz, 1H), 8.43 (d, J=2.50 Hz, 1H), 9.17 (s, 1H), 12.15 (br s, 1H); MS (ESI) [M+1]⁺ 502.

Example C-71

4-(5-(2-ethyl-4-(phenylcarbamoyl)-3,4-dihydro-2H-benzo[b][1,4]oxazin-7-yl)pyridin-2-yloxy)cyclohexanecarboxylic acid (isomer B)

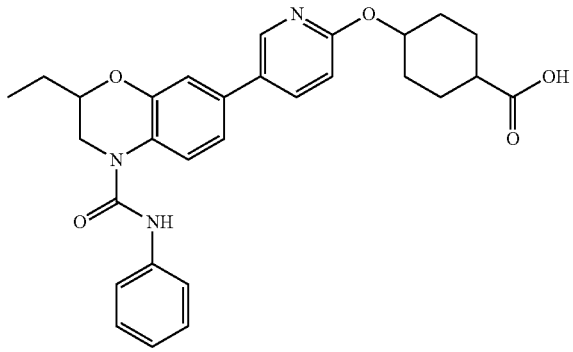 [SMILES: CCC1CN(C(=O)Nc2ccccc2)c2ccc(-c3ccc(OC4CCC(C(=O)O)CC4)nc3)cc2O1]

$^1$H NMR (500 MHz, DMSO-d$_6$) δ ppm 1.02 (t, J=7.50 Hz, 3H), 1.42-1.54 (m, 4H), 1.64-1.75 (m, 2H), 1.97-2.13 (m, 4H), 2.25-2.30 (m, 1H), 3.45-3.49 (m, 1H), 4.02-4.05 (m, 1H), 4.14-4.19 (m, 1H), 4.95-5.00 (m, 1H), 6.81 (d, J=8.50 Hz, 1H), 7.01 (t, J=7.50 Hz, 1H), 7.16-7.19 (m, 2H), 7.29 (t, J=7.50 Hz, 2H), 7.49 (d, J=8.50 Hz, 2H), 7.54 (d, J=8.00 Hz, 1H), 7.97 (dd, J=1.50, 8.50 Hz, 1H), 8.44 (d, J=2.00 Hz, 1H), 9.17 (s, 1H), 12.14 (br s, 1H); MS (ESI) [M+1]$^+$ 502.

Example C-72

4-(6-(4-(phenylcarbamoyl)-3,4-dihydro-2H-benzo[b][1,4]oxazin-7-yl)quinolin-2-yloxy)cyclohexanecarboxylic acid

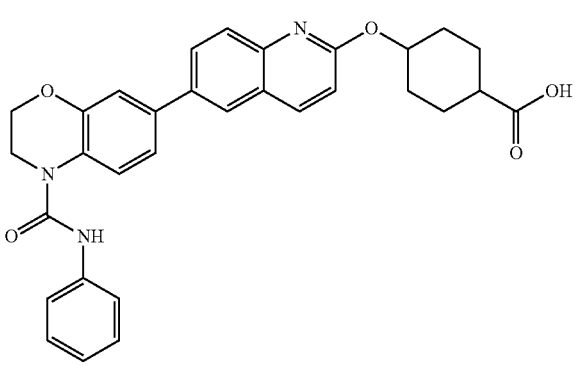 [SMILES: O=C(O)C1CCC(Oc2ccc3cc(-c4ccc5c(c4)OCCN5C(=O)Nc4ccccc4)ccc3n2)CC1]

$^1$H NMR (500 MHz, DMSO-d$_6$) (major isomer described) δ ppm 1.47-1.61 (m, 4H), 2.00-2.21 (m, 4H), 2.29-2.34 (m, 1H), 3.90 (d, J=4.00 Hz, 1H), 4.33 (t, J=4.00 Hz, 2H), 5.19-5.23 (m, 1H), 6.98-7.03 (m, 2H), 7.29-7.33 (m, 4H), 7.52 (d, J=8.50 Hz, 2H), 7.66 (d, J=9.00 Hz, 1H), 7.77-7.80 (m, 1H), 7.97 (d, J=9.00 Hz, 1H), 8.17 (s, 1H), 8.27 (d, J=9.00 Hz, 1H), 9.18 (s, 1H), 12.16 (br s, 1H); MS (ESI) [M+1]$^+$ 524.

Example C-73 ethyl 4-(6-(4-(phenylcarbamoyl)-3,4-dihydro-2H-benzo[b][1,4]oxazin-7-yl)quinolin-2-yloxy)cyclohexanecarboxylate

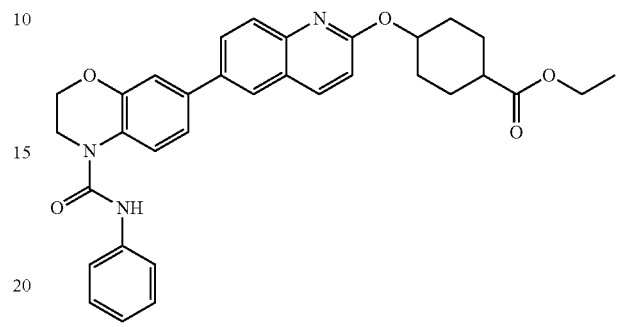

$^1$H NMR (500 MHz, CHLOROFORM-d) (major isomer described) δ ppm 1.31 (t, J=7.50 Hz, 3H), 1.58-2.08 (m, 8H), 2.47-2.52 (m, 1H), 4.04 (t, J=4.00 Hz, 2H), 4.19 (q, J=7.50 Hz, 2H), 4.40 (t, J=4.00 Hz, 2H), 5.55-5.63 (m, 1H), 6.99 (d, J=9.00 Hz, 1H), 7.12 (t, J=7.00 Hz, 1H), 7.29-7.37 (m, 5H), 7.44-7.48 (m, 3H), 7.88-7.93 (m, 2H), 7.96-8.00 (m, 1H), 8.07-8.11 (m, 1H); MS (ESI) [M+1]$^+$ 552.

Example C-74

(1s,4s)-4-(4-(4-(phenylcarbamoyl)-3,4-dihydro-2H-benzo[b][1,4]oxazin-7-yl)benzoyl)cyclohexanecarboxylic acid

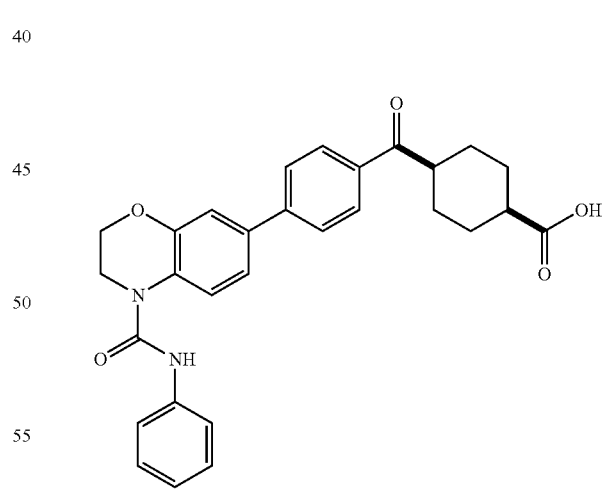

$^1$H NMR (500 MHz, DMSO-d$_6$) δ ppm 1.36-1.55 (m, 4H), 1.88-2.00 (m, 4H), 2.19-2.26 (m, 1H), 3.41-3.46 (m, 1H), 3.90 (t, J=4.00 Hz, 2H), 4.32 (t, J=4.00 Hz, 2H), 7.02 (t, J=7.50 Hz, 1H), 7.29-7.32 (m, 4H), 7.51 (d, J=8.00 Hz, 2H), 7.65 (d, J=9.00 Hz, 1H), 7.81 (d, J=8.00 Hz, 2H), 8.04 (d, J=8.50 Hz, 2H), 9.22 (s, 1H), 12.11 (br s, 1H); MS (ESI) [M+1]$^+$ 485.

Example C-75

(1r,4r)-4-(5-(4-(phenylcarbamoyl)-3,4-dihydro-2H-benzo[b][1,4]oxazin-7-yl)pyridin-2-ylcarbamoyl)cyclohexanecarboxylic acid

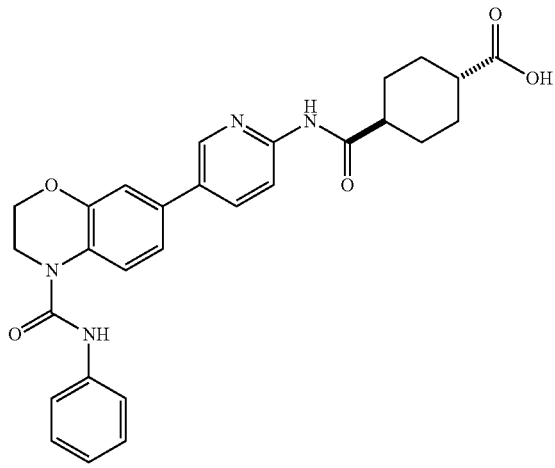 [SMILES: O=C(Nc1ccccc1)N1CCOc2cc(-c3ccc(NC(=O)[C@H]4CC[C@H](C(=O)O)CC4)nc3)ccc21]

$^1$H NMR (500 MHz, DMSO-d$_6$) δ ppm 1.30-1.50 (m, 4H), 1.87-2.00 (m, 4H), 2.18-2.23 (m, 1H), 3.88 (t, J=4.00 Hz, 2H), 4.31 (t, J=4.00 Hz, 2H), 7.01 (t, J=7.50 Hz, 1H), 7.23-7.31 (m, 4H), 7.51 (d, J=8.00 Hz, 2H), 7.62 (d, J=8.50 Hz, 1H), 8.05-8.07 (m, 1H), 8.14-8.15 (m, 1H), 8.62 (br s, 1H), 9.17 (s, 1H), 10.48 (s, 1H), 12.09 (br s, 1H); MS (ESI) [M+1]$^+$ 501.

Example C-76

4-(5-(2-ethyl-4-(2-(trifluoromethyl)phenylcarbamoyl)-3,4-dihydro-2H-benzo[b][1,4]oxazin-7-yl)pyridin-2-yloxy)cyclohexanecarboxylic acid

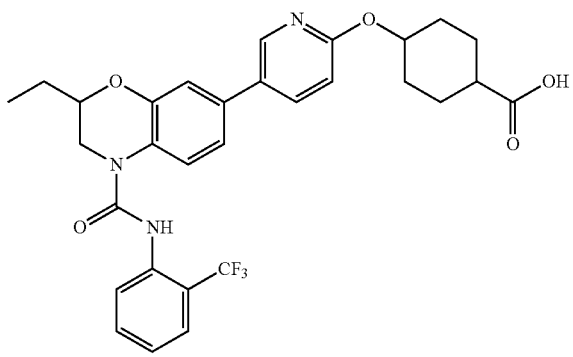 [SMILES: CCC1CN(C(=O)Nc2ccccc2C(F)(F)F)c2ccc(-c3ccc(OC4CCC(C(=O)O)CC4)nc3)cc2O1]

$^1$H NMR (500 MHz, DMSO-d$_6$) (major isomer described) δ ppm 1.02 (t, J=7.50 Hz, 3H), 1.41-1.54 (m, 4H), 1.62-1.87 (m, 2H), 1.97-2.13 (m, 4H), 2.25-2.31 (m, 1H), 3.46-3.50 (m, 1H), 4.08-4.17 (m, 2H), 4.94-4.99 (m, 1H), 6.81 (d, J=8.50 Hz, 1H), 7.18-7.20 (m, 2H), 7.46 (t, J=8.00 Hz, 1H), 7.57 (d, J=8.00 Hz, 1H), 7.64-7.75 (m, 3H), 7.96-7.99 (m, 1H), 8.44-8.45 (m, 1H), 8.81 (s, 1H), 12.15 (br s, 1H); MS (ESI) [M+1]$^+$ 570.

Example C-77 ethyl 4-(5-(2-ethyl-4-(2-(trifluoromethyl)phenylcarbamoyl)-3,4-dihydro-2H-benzo[b][1,4]oxazin-7-yl)pyridin-2-yloxy)cyclohexanecarboxylate

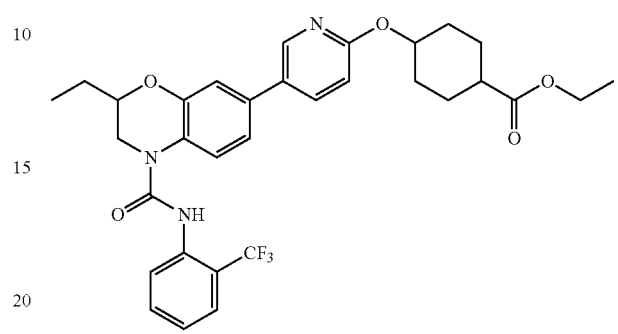

$^1$H NMR (500 MHz, CHLOROFORM-d) (major isomer described) δ ppm 1.13 (t, J=7.50 Hz, 3H), 1.30 (t, J=7.50 Hz, 3H), 1.52-1.85 (m, 6H), 1.98-2.13 (m, 4H), 2.26-2.47 (m, 1H), 3.33 (dd, J=8.50, 13.5 Hz, 1H), 4.15-4.22 (m, 3H), 4.44 (dd, J=2.50, 13.5 Hz, 1H), 5.30-5.34 (m, 1H), 6.84 (d, J=8.50 Hz, 1H), 7.13-7.23 (m, 3H), 7.44 (d, J=8.50 Hz, 1H), 7.58-7.61 (m, 2H), 7.72 (br s, 1H), 7.82-7.84 (m, 1H), 8.21 (d, J=8.50 Hz, 1H), 8.39 (d, J=2.50 Hz, 1H); MS (ESI) [M+1]$^+$ 598.

Example C-78

4-(6-(4-(phenylcarbamoyl)-3,4-dihydro-2H-benzo[b][1,4]oxazin-7-yl)pyridin-3-yloxy)cyclohexanecarboxylic acid

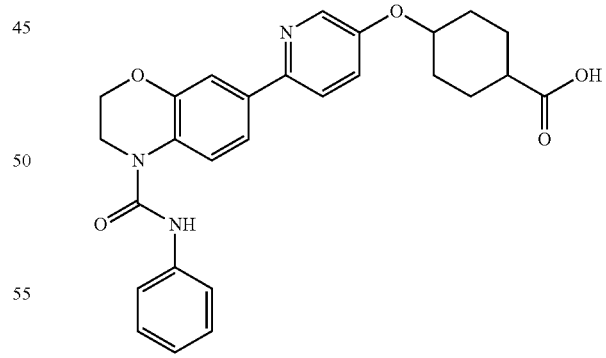

$^1$H NMR (500 MHz, DMSO-d$_6$) (major isomer described) δ ppm 1.39-1.58 (m, 4H), 1.95-2.12 (m, 4H), 2.24-2.30 (m, 1H), 3.88 (t, J=4.50 Hz, 2H), 4.30 (t, J=4.50 Hz, 2H), 4.41-4.47 (m, 1H), 7.01 (dt, J=0.50, 7.50 Hz, 1H), 7.30 (t, J=7.50 Hz, 2H), 7.45-7.54 (m, 5H), 7.59-7.61 (m, 1H), 7.84 (d, J=8.50 Hz, 1H), 8.32 (d, J=3.00 Hz, 1H), 9.18 (s, 1H), 12.17 (br s, 1H); MS (ESI) [M+1]$^+$ 474.

Example C-79 methyl 1-((5-(4-(phenylcarbamoyl)-3,4-dihydro-21'-benzo[b][1,4]oxazin-7-yl)pyridin-2-yloxy)methyl)cyclopropanecarboxylate

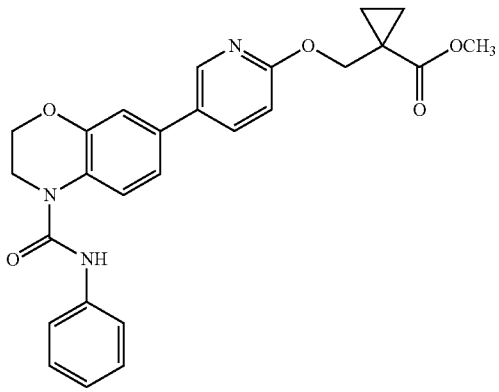 [SMILES: COC(=O)C1(COc2ccc(-c3ccc4c(c3)OCCN4C(=O)Nc3ccccc3)cn2)CC1]

$^1$H NMR (500 MHz, CHLOROFORM-d) δ ppm 1.09 (q, J=4.00 Hz, 2H), 1.42 (q, J=4.00 Hz, 2H), 3.74 (s, 3H), 4.02 (t, J=4.50 Hz, 2H), 4.38 (t, J=4.50 Hz, 2H), 4.53 (s, 2H), 6.87 (d, J=8.50 Hz, 1H), 7.10-7.15 (m, 2H), 7.18 (d, J=2.50 Hz, 1H), 7.25 (br s, 1H), 7.34-7.37 (m, 2H), 7.42-7.45 (m, 3H), 7.80 (dd, J=2.50, 8.50 Hz, 1H), 8.36 (d, J=2.50 Hz, 1H); MS (ESI) [M+1]$^+$ 460.

Example C-80 methyl 1-((5-(2-methyl-4-(phenylcarbamoyl)-3,4-dihydro-2H-benzo[b][1,4]oxazin-7-yl)pyridin-2-yloxy)methyl)cyclopropanecarboxylate

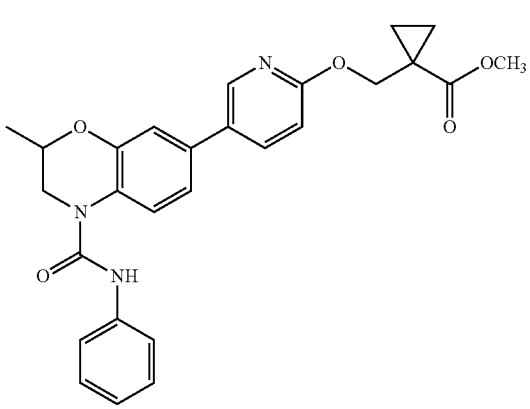 [SMILES: COC(=O)C1(COc2ccc(-c3ccc4c(c3)OC(C)CN4C(=O)Nc3ccccc3)cn2)CC1]

$^1$H NMR (500 MHz, CHLOROFORM-d) δ ppm 1.10 (q, J=4.00 Hz, 2H), 1.41-1.45 (m, 5H), 3.19 (dd, J=9.00, 13.50 Hz, 1H), 3.74 (s, 3H), 4.38-4.42 (m, 1H), 4.49 (dd, J=2.50, 13.50 Hz, 1H), 4.55 (s, 2H), 6.89 (d, J=8.50 Hz, 1H), 7.11-7.14 (m, 2H), 7.18 (d, J=2.50 Hz, 1H), 7.25 (br s, 1H), 7.34-7.37 (m, 2H), 7.43-7.45 (m, 3H), 7.80 (dd, J=2.50, 8.50 Hz, 1H), 8.37 (d, J=2.50 Hz, 1H); MS (ESI) [M+1]$^+$ 474.

Example C-81

4-(5-(4-(phenylcarbamoyl)-3,4-dihydro-2H-benzo[b][1,4]oxazin-7-yl)pyrazin-2-yloxy)cyclohexanecarboxylic acid

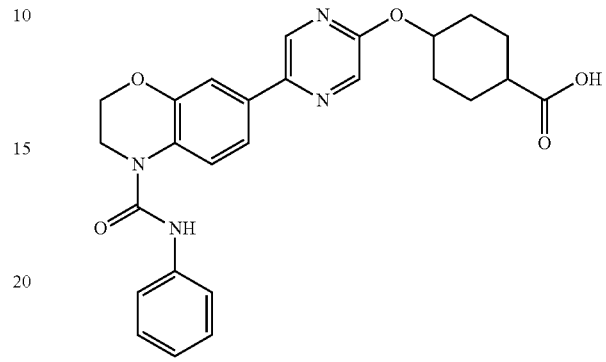

$^1$H NMR (500 MHz, DMSO-d$_6$) (major isomer described) δ ppm 1.46-1.55 (m, 4H), 1.97-2.16 (m, 4H), 2.28-2.33 (m, 1H), 3.89 (t, J=4.50 Hz, 2H), 4.31 (t, J=4.50 Hz, 2H), 4.93-4.99 (m, 1H), 7.02 (t, J=7.50 Hz, 1H), 7.30 (t, J=7.50 Hz, 2H), 7.50-7.55 (m, 4H), 7.62-7.64 (m, 1H), 8.29 (br s, 1H), 8.75 (br s, 1H), 9.20 (s, 1H), 12.16 (br s, 1H); MS (ESI) [M+1]$^+$ 475.

Example C-82 methyl 1-((5-(2-ethyl-4-(phenylcarbamoyl)-3,4-dihydro-2H-benzo[b][1,4]oxazin-7-yl)pyridin-2-yloxy)methyl)cyclopropanecarboxylate

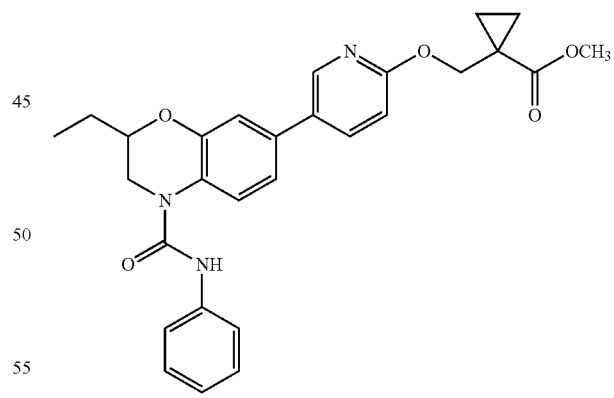

$^1$H NMR (500 MHz, DMSO-d$_6$) δ ppm 1.02 (t, J=7.50 Hz, 3H), 1.11 (q, J=4.00 Hz, 2H), 1.25 (q, J=4.00 Hz, 2H), 1.62-1.75 (m, 2H), 3.47 (dd, J=7.50, 13.50 Hz, 1H), 3.63 (s, 3H), 4.04 (dd, J=2.00, 13.50 Hz, 1H), 4.14-4.19 (m, 1H), 4.41 (s, 2H), 6.89 (d, J=8.50 Hz, 1H), 7.01 (t, J=7.50 Hz, 1H), 7.17-7.20 (m, 2H), 7.29 (t, J=8.00 Hz, 2H), 7.50 (d, J=8.50 Hz, 2H), 7.55 (d, J=8.50 Hz, 1H), 7.99 (dd, J=2.50, 8.50 Hz, 1H), 8.44 (d, J=2.50 Hz, 1H), 9.17 (s, 1H); MS (ESI) [M+1]$^+$ 488.

Example C-83

1-((5-(4-(phenylcarbamoyl)-3,4-dihydro-2H-benzo[b][1,4]oxazin-7-yl)pyridin-2-yloxy)methyl)cyclopropanecarboxylic acid

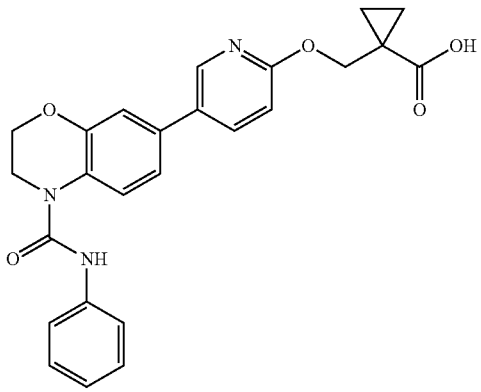 [SMILES: O=C(Nc1ccccc1)N1CCOc2cc(-c3ccc(OCC4(C(=O)O)CC4)nc3)ccc21]

$^1$H NMR (500 MHz, DMSO-d$_6$) δ ppm 1.03 (q, J=4.00 Hz, 2H), 1.20 (q, J=4.00 Hz, 2H), 3.88 (t, J=4.50 Hz, 2H), 4.30 (t, J=4.50 Hz, 2H), 4.39 (s, 2H), 6.89 (d, J=9.00 Hz, 1H), 7.01 (dt, J=1.00, 7.50 Hz, 1H), 7.17-7.20 (m, 2H), 7.29 (t, J=7.50 Hz, 2H), 7.50 (d, J=8.50 Hz, 2H), 7.59 (d, J=8.50 Hz, 1H), 7.97 (dd, J=2.50, 8.50 Hz, 1H), 8.43 (d, J=2.50 Hz, 1H), 9.16 (s, 1H), 12.41 (br s, 1H); MS (ESI) [M+1]$^+$ 446.

Example C-84

1-((5-(2-methyl-4-(phenylcarbamoyl)-3,4-dihydro-2H-benzo[b][1,4]oxazin-7-yl)pyridin-2-yloxy)methyl)cyclopropanecarboxylic acid

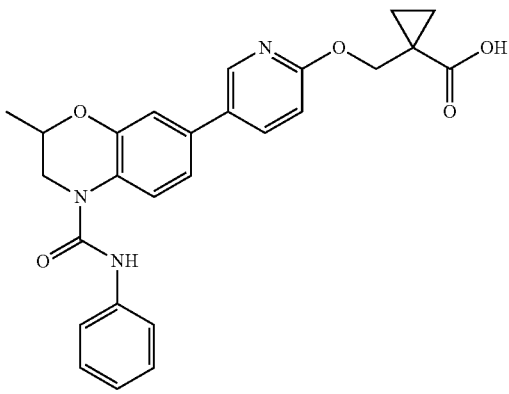 [SMILES: CC1CN(C(=O)Nc2ccccc2)c2ccc(-c3ccc(OCC4(C(=O)O)CC4)nc3)cc2O1]

$^1$H NMR (500 MHz, DMSO-d$_6$) δ ppm 1.04 (q, J=4.00 Hz, 2H), 1.20 (q, J=4.00 Hz, 2H), 1.35 (d, J=6.50 Hz, 3H), 3.32-3.38 (m, 1H), 4.09-4.12 (m, 1H), 4.35-4.38 (m, 1H), 4.38 (s, 2H), 6.88 (d, J=9.00 Hz, 1H), 7.01 (t, J=7.50 Hz, 1H), 7.17-7.19 (m, 2H), 7.29 (t, J=8.00 Hz, 2H), 7.50 (d, J=8.50 Hz, 2H), 7.57 (d, J=8.00 Hz, 1H), 7.98 (dd, J=2.50, 8.50 Hz, 1H), 8.43 (d, J=2.50 Hz, 1H), 9.18 (s, 1H), 12.39 (br s, 1H); MS (ESI) [M+1]$^+$ 460.

Example C-85 ethyl 4-(6-(4-(phenylcarbamoyl)-3,4-dihydro-2H-benzo[b][1,4]oxazin-7-yl)pyridin-3-yloxy)cyclohexanecarboxylate

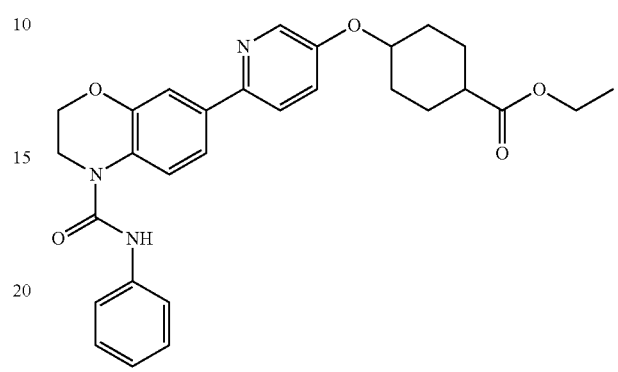

$^1$H NMR (500 MHz, CHLOROFORM-d) (major isomer described) δ ppm 1.30 (t, J=7.50 Hz, 3H), 1.72-1.84 (m, 4H), 1.97-2.12 (m, 4H), 2.34-2.50 (m, 1H), 4.01 (t, J=4.50 Hz, 2H), 4.19 (q, J=7.50 Hz, 2H), 4.38 (t, J=4.50 Hz, 2H), 4.61-4.64 (m, 1H), 7.11 (t, J=7.50 Hz, 1H), 7.30 (br s, 1H), 7.35 (t, J=7.50 Hz, 2H), 7.41-7.48 (m, 4H), 7.54-7.59 (m, 2H), 7.67-7.70 (m, 1H), 8.46 (d, J=2.50 Hz, 1H); MS (ESI) [M+1]$^+$ 502.

Example C-86

1-((5-(2-ethyl-4-(phenylcarbamoyl)-3,4-dihydro-2H-benzo[b][1,4]oxazin-7-yl)pyridin-2-yloxy)methyl)cyclopropanecarboxylic acid

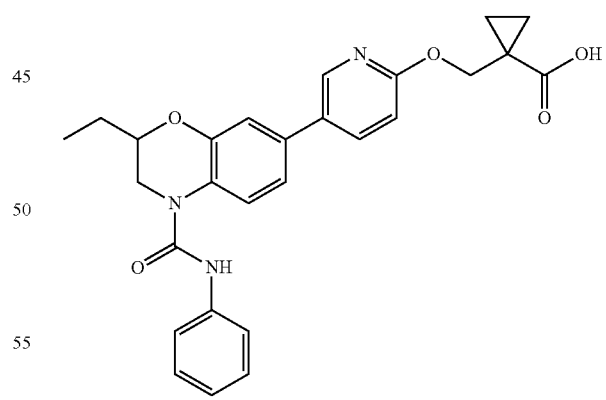

$^1$H NMR (500 MHz, DMSO-d$_6$) δ ppm 1.01-1.04 (m, 5H), 1.19-1.24 (m, 2H), 1.64-1.75 (m, 2H), 3.47 (dd, J=7.00, 13.50 Hz, 1H), 4.04 (d, J=13.50 Hz, 1H), 4.15-4.18 (m, 1H), 4.38 (s, 2H), 6.88 (d, J=8.50 Hz, 1H), 7.01 (t, J=7.50 Hz, 1H), 7.17-7.20 (m, 2H), 7.29 (t, J=7.50 Hz, 2H), 7.50 (d, J=8.50 Hz, 2H), 7.55 (d, J=8.50 Hz, 1H), 7.98 (d, J=9.00 Hz, 1H), 8.43 (s, 1H), 9.17 (s, 1H), 12.40 (br s, 1H); MS (ESI) [M+1]$^+$ 474.

Example C-87

4-(5-(4-(2-ethylphenylcarbamoyl)-3,4-dihydro-2H-benzo[b][1,4]oxazin-7-yl)pyridin-2-yloxy)cyclohexanecarboxylic acid

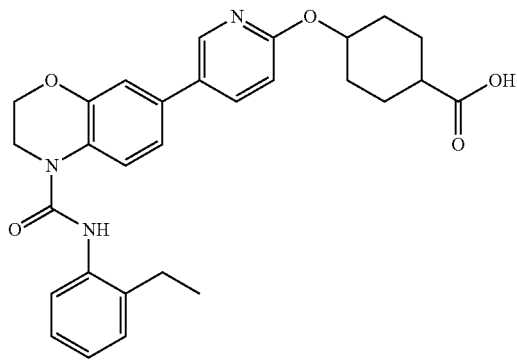 [SMILES: CCc1ccccc1NC(=O)N1CCOc2cc(-c3ccc(OC4CCC(C(=O)O)CC4)nc3)ccc21]

$^1$H NMR (500 MHz, DMSO-d$_6$) (major isomer described) δ ppm 1.16 (t, J=7.50 Hz, 3H), 1.65-1.88 (m, 8H), 2.37-2.40 (m, 1H), 2.60 (q, J=7.50 Hz, 2H), 3.90 (t, J=4.50 Hz, 2H), 4.32 (t, J=4.50 Hz, 2H), 5.17-5.20 (m, 1H), 6.85 (d, J=9.00 Hz, 1H), 7.14-7.21 (m, 4H), 7.25-7.27 (m, 1H), 7.30-7.32 (m, 1H), 7.71 (d, J=8.50 Hz, 1H), 7.96 (dd, J=2.50, 8.50 Hz, 1H), 8.43 (d, J=2.50 Hz, 1H), 8.56 (s, 1H), 12.23 (br s, 1H); MS (ESI) [M+1]$^+$ 502.

Example C-88 ethyl 4-(5-(4-(4-fluoro-2-(trifluoromethyl)phenylcarbamoyl)-3,4-dihydro-2H-benzo[b][1,4]oxazin-7-yl)pyridin-2-yloxy)cyclohexanecarboxylate

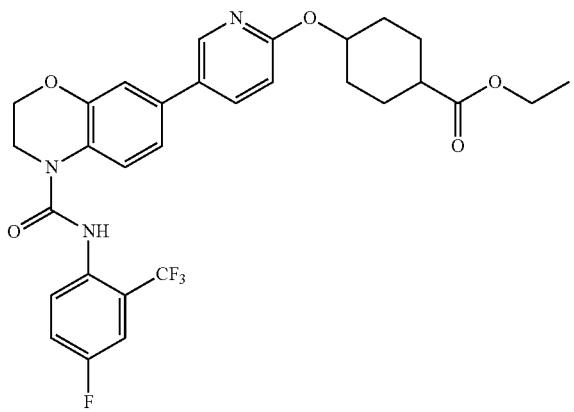 [SMILES: CCOC(=O)C1CCC(Oc2ccc(-c3ccc4c(c3)OCCN4C(=O)Nc3ccc(F)cc3C(F)(F)F)cn2)CC1]

$^1$H NMR (500 MHz, CHLOROFORM-d) (major isomer described) δ ppm 1.28-1.31 (m, 3H), 1.49-1.77 (m, 4H), 2.10-2.29 (m, 4H), 2.34-2.40 (m, 1H), 4.02 (t, J=4.50 Hz, 2H), 4.15-4.20 (m, 2H), 4.40 (t, J=4.50 Hz, 2H), 5.05-5.10 (m, 1H), 6.78 (d, J=8.50 Hz, 1H), 7.15-7.18 (m, 2H), 7.29-7.34 (m, 2H), 7.43 (d, J=8.50 Hz, 1H), 7.61 (br s, 1H), 7.78 (dt, J=2.50, 8.50 Hz, 1H), 8.13 (dd, J=5.00, 9.00 Hz, 1H), 8.36-8.37 (m, 1H); MS (ESI) [M+1]$^+$ 588.

Example C-89 ethyl 4-(5-(4-(2,4-difluorophenylcarbamoyl)-3,4-dihydro-2H-benzo[b][1,4]oxazin-7-yl)pyridin-2-yloxy)cyclohexanecarboxylate

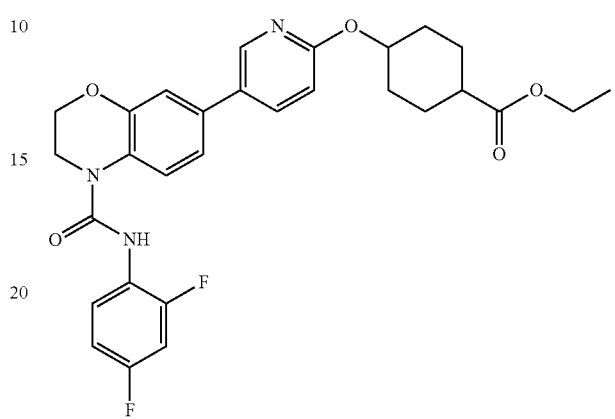

$^1$H NMR (500 MHz, CHLOROFORM-d) (major isomer described) δ ppm 1.28-1.31 (m, 3H), 1.49-1.77 (m, 4H), 2.09-2.29 (m, 4H), 2.34-2.41 (m, 1H), 4.02 (t, J=4.50 Hz, 2H), 4.15-4.21 (m, 2H), 4.39 (t, J=4.50 Hz, 2H), 5.05-5.11 (m, 1H), 6.78 (d, J=8.50 Hz, 1H), 6.86-6.94 (m, 2H), 7.15-7.18 (m, 2H), 7.46-7.47 (m, 2H), 7.78 (dt, J=2.50, 8.50 Hz, 1H), 8.14 (dt, J=6.00, 9.00 Hz, 1H), 8.36-8.37 (m, 1H); MS (ESI) [M+1]$^+$ 538.

Example C-90 ethyl 4-(5-(2-ethyl-4-(2-ethylphenylcarbamoyl)-3,4-dihydro-2H-benzo[b][1,4]oxazin-7-yl)pyridin-2-yloxy)cyclohexanecarboxylate

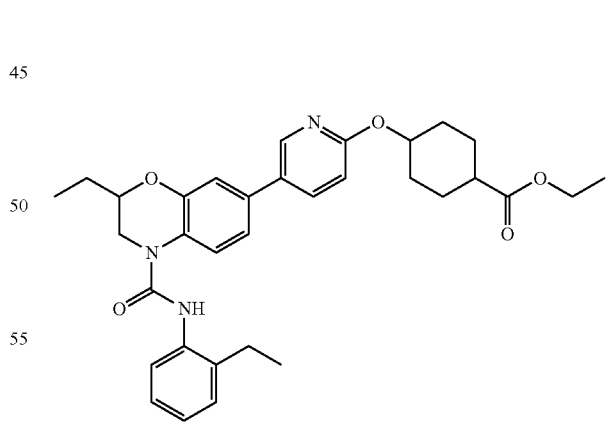

$^1$H NMR (500 MHz, CHLOROFORM-d) (major isomer described) δ ppm 1.11-1.31 (m, 9H), 1.49-1.84 (m, 6H), 2.08-2.34 (m, 4H), 2.35-2.41 (m, 1H), 2.49-2.54 (m, 2H), 3.29 (dd, J=8.50, 13.50 Hz, 1H), 4.15-4.21 (m, 3H), 4.47 (dd, J=2.50, 13.50 Hz, 1H), 5.05-5.10 (m, 1H), 6.78 (d, J=8.50 Hz, 1H), 7.10-7.13 (m, 2H), 7.19-7.28 (m, 4H), 7.49 (d, J=8.50

Hz, 1H), 7.79 (dt, J=2.50, 8.50 Hz, 1H), 7.85 (d, J=8.50 Hz, 1H), 8.37 (d, J=2.50 Hz, 1H); MS (ESI) [M+1]+ 558.

Example C-91

4-(5-(4-(4-fluoro-2-(trifluoromethyl)phenylcarbamoyl)-3,4-dihydro-2H-benzo[b][1,4]oxazin-7-yl)pyridin-2-yloxy)cyclohexanecarboxylic acid

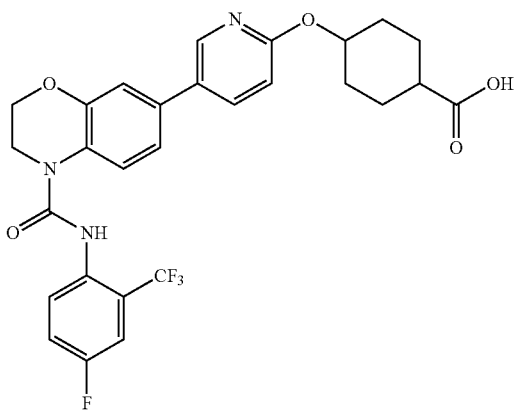

1H NMR (500 MHz, DMSO-d6) (major isomer described) δ ppm 1.41-1.54 (m, 4H), 1.97-2.13 (m, 4H), 2.25-2.30 (m, 1H), 3.89 (t, J=4.50 Hz, 2H), 4.31 (t, J=4.50 Hz, 2H), 4.93-4.99 (m, 1H), 6.81 (d, J=8.50 Hz, 1H), 7.18-7.20 (m, 2H), 7.58-7.60 (m, 2H), 7.65-7.69 (m, 2H), 7.95-7.98 (m, 1H), 8.45 (d, J=2.50 Hz, 1H), 8.82 (s, 1H), 12.17 (br s, 1H); MS (ESI) [M+1]+ 560.

Example C-92

4-(5-(4-(2,4-difluorophenylcarbamoyl)-3,4-dihydro-2H-benzo[b][1,4]oxazin-7-yl)pyridin-2-yloxy)cyclohexanecarboxylic acid

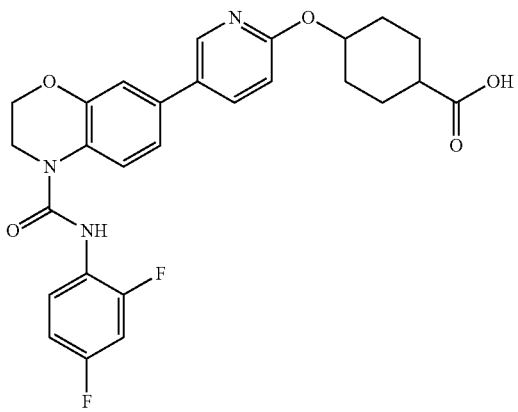 [SMILES: O=C(O)C1CCC(Oc2ccc(-c3ccc4c(c3)OCCN4C(=O)Nc3ccc(F)cc3F)cn2)CC1]

1H NMR (500 MHz, DMSO-d5) (major isomer described) δ ppm 1.41-1.53 (m, 4H), 1.97-2.13 (m, 4H), 2.25-2.31 (m, 1H), 3.89 (t, J=4.50 Hz, 2H), 4.31 (t, J=4.50 Hz, 2H), 4.94-4.99 (m, 1H), 6.81 (d, J=8.50 Hz, 1H), 7.05-7.09 (m, 1H), 7.18-7.20 (m, 2H), 7.29-7.33 (m, 1H), 7.49-7.54 (m, 1H), 7.69 (d, J=8.50 Hz, 1H), 7.96 (d, J=8.50 Hz, 1H), 8.45 (d, J=2.50 Hz, 1H), 8.89 (s, 1H), 12.16 (br s, 1H); MS (ESI) [M+1]+ 510.

Example C-93

4-(5-(2-ethyl-4-(2-ethylphenylcarbamoyl)-3,4-dihydro-2H-benzo[b][1,4]oxazin-7-yl)pyridin-2-yloxy)cyclohexanecarboxylic acid

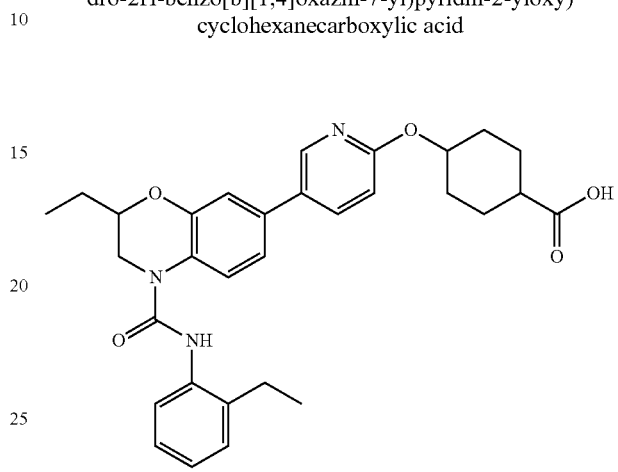

1H NMR (500 MHz, DMSO-d6) (major isomer described) δ ppm 1.04 (t, J=7.50 Hz, 3H), 1.16 (t, J=7.50 Hz, 3H), 1.41-1.54 (m, 4H), 1.65-1.87 (m, 2H), 1.97-2.13 (m, 4H), 2.25-2.31 (m, 1H), 2.60 (q, J=7.50 Hz, 2H), 3.51 (dd, J=7.50, 13.50 Hz, 1H), 4.05-4.08 (m, 1H), 4.15-4.19 (m, 1H), 4.94-4.99 (m, 1H), 6.81 (d, J=8.50 Hz, 1H), 7.15-7.20 (m, 4H), 7.25-7.30 (m, 2H), 7.67 (d, J=8.50 Hz, 1H), 7.95-7.98 (m, 1H), 8.44 (d, J=2.50 Hz, 1H), 8.58 (s, 1H), 12.15 (br s, 1H); MS (ESI) [M+1]+ 530.

Biological Assay

The assay used to determine the DGAT inhibitory activity of the inventive compounds is described below:

The in vitro assay to identify DGAT1 inhibitors uses human DGAT1 enzyme expressed in Sf9 insect cells prepared as microsomes. The reaction was initiated by the addition of the combined substrates 1,2-dioleoyl-sn-glycerol and [$^{14}$C]-palmitoyl-CoA and incubated with test compounds and microsomal membranes for 2 hours at room temperature. The assay was stopped by adding 0.5 mg wheat germ agglutinin beads in assay buffer with 1% Brij-35 and 1% 3-cholamidopropyldimethyl-ammonio-1-propane sulfonate. Plates were sealed with TopSeal and incubated for 18 hours to allow the radioactive triglyceride product to come into proximity with the bead. Plates were read on a TopCount instrument.

Percent inhibition was calculated as the percent of (test compound inhibition minus non-specific binding) relative to (total binding minus non-specific binding). IC$_{50}$ values were determined by curve fitting the data to a Sigmoidal dose-response in GraphPad Prism utilizing the following equation:

$$Y=A+(B-A)/(1+10^{((\text{Log IC}_{50}-X))}),$$

where A and B are the bottom and top of the curve (highest and lowest inhibition), respectively, and X is the logarithm of concentration.

| Biological Data | | |
|---|---|---|
| Compound Number | Structure | hDGAT1 IC50 (nM) |
| C-65 | | 60 |
| C-68 | | 156 |
| C-70 isomer A | | 36 |
| C-71 isomer B | | 54 |
| C-87 | | 67 |

-continued

| Biological Data | | |
|---|---|---|
| Compound Number | Structure | hDGAT1 IC50 (nM) |
| C-91 | *structure* | 85 |
| B-4 | *structure* | 138 |
| C-1 | *structure* | 254 |
| C-3 | *structure* | 131 |
| C-5 | *structure* | 118 |

-continued

Biological Data

| Compound Number | Structure | hDGAT1 IC50 (nM) |
|---|---|---|
| C-8 | 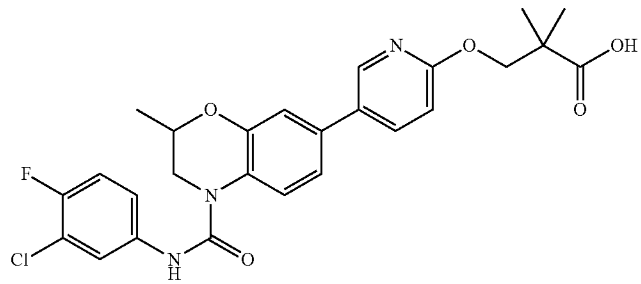 [SMILES: CC1CN(C(=O)Nc2ccc(F)c(Cl)c2)c2ccc(-c3ccc(OCC(C)(C)C(=O)O)nc3)cc2O1] | 119 |
| C-60 | 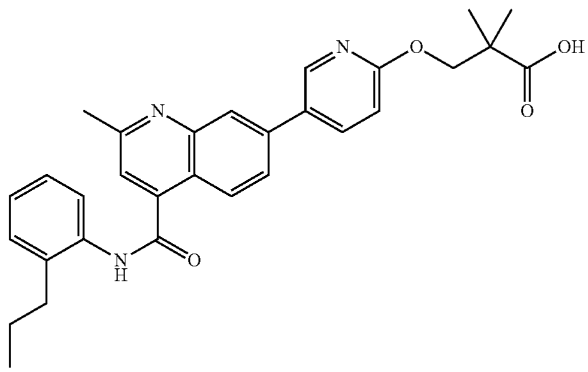 [SMILES: CCCc1ccccc1NC(=O)c1cc(C)nc2cc(-c3ccc(OCC(C)(C)C(=O)O)nc3)ccc12] | 280 |
| B-17 | 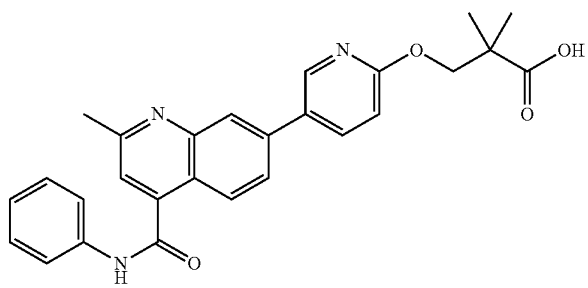 [SMILES: Cc1cc(C(=O)Nc2ccccc2)c2ccc(-c3ccc(OCC(C)(C)C(=O)O)nc3)cc2n1] | 275 |
| B-13 | 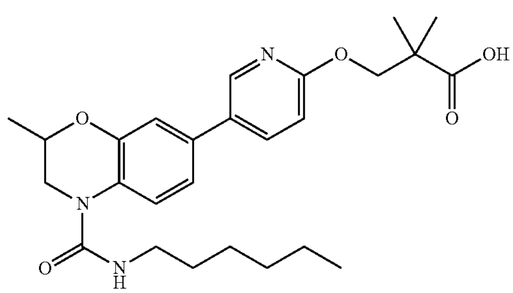 [SMILES: CCCCCCNC(=O)N1CC(C)Oc2cc(-c3ccc(OCC(C)(C)C(=O)O)nc3)ccc21] | 87 |
| C-56 | 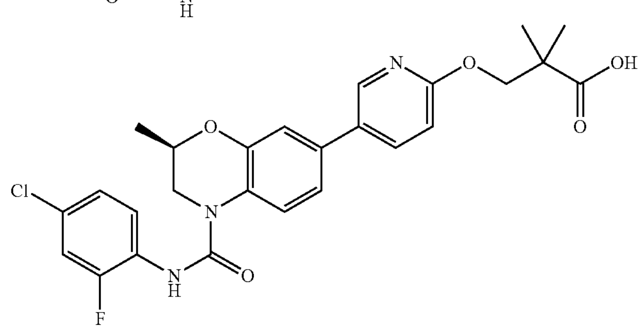 | 131 |

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A compound, or pharmaceutically acceptable salt of said compound, the compound being represented by the Formula IB

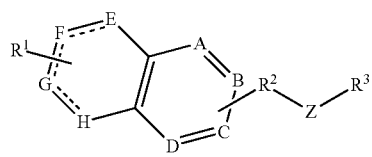

or a stereoisomer or tautomer of said compound, wherein the bond denoted by === represents a single bond;

E is O;

F is $C(R^4R^{4'})$;

G is $C(R^4R^{4'})$;

H is $N(R^{4'})$;

$R^4$ is present depending on the allowed vacancy and is selected from H, alkyl, or hydroxyalkyl;

$R^{4'}$ is present depending on the allowed vacancy and is $R^1$;

$R^1$ is selected from the group consisting of (alkylamino)carbonyl, (cycloalkylamino)carbonyl, (heterocycloalkylamino)carbonyl, and (arylamino)carbonyl, wherein each of these $R^1$ groups is unsubstituted or optionally independently substituted with 1-4 substituents independently selected from halogen, amino, alkylamino, hydroxy, alkoxy, alkyl, cycloalkyl, carboxy, carboxyester, methylenedioxy, CN, cyanoalkyl-, nitro and $CF_3$;

A is $CR^5$;

B is $CR^5$;

C is $CR^5$;

D is $CR^5$;

$R^5$ is selected from H, alkyl, or halogen, wherein each of these $R^5$ groups is unsubstituted or optionally independently substituted with 1-4 substituents independently selected from halogen, amino, alkylamino, hydroxy, alkoxy, alkyl, cycloalkyl, CN and $CF_3$;

$R^2$ is heteroaryl, wherein said heteroaryl is a six-membered aromatic ring system containing 1 to 2 N atoms, and wherein said heteroaryl is unsubstituted or optionally independently substituted with 1-4 substituents independently selected from halogen, amino, alkylamino, hydroxy, alkoxy, alkyl, cycloalkyl, CN and $CF_3$;

Z is O; and $R^3$ is selected from the group consisting of alkyl or cycloalkyl.

2. A pharmaceutical composition comprising at least one compound of claim 1 and at least one pharmaceutically acceptable carrier.

3. A method of treating obesity, diabetes or metabolic syndrome in a patient in need thereof comprising administering therapeutically effective amounts of at least one compound of claim 1 to said patient.

4. A compound selected from the compounds of the formulae:

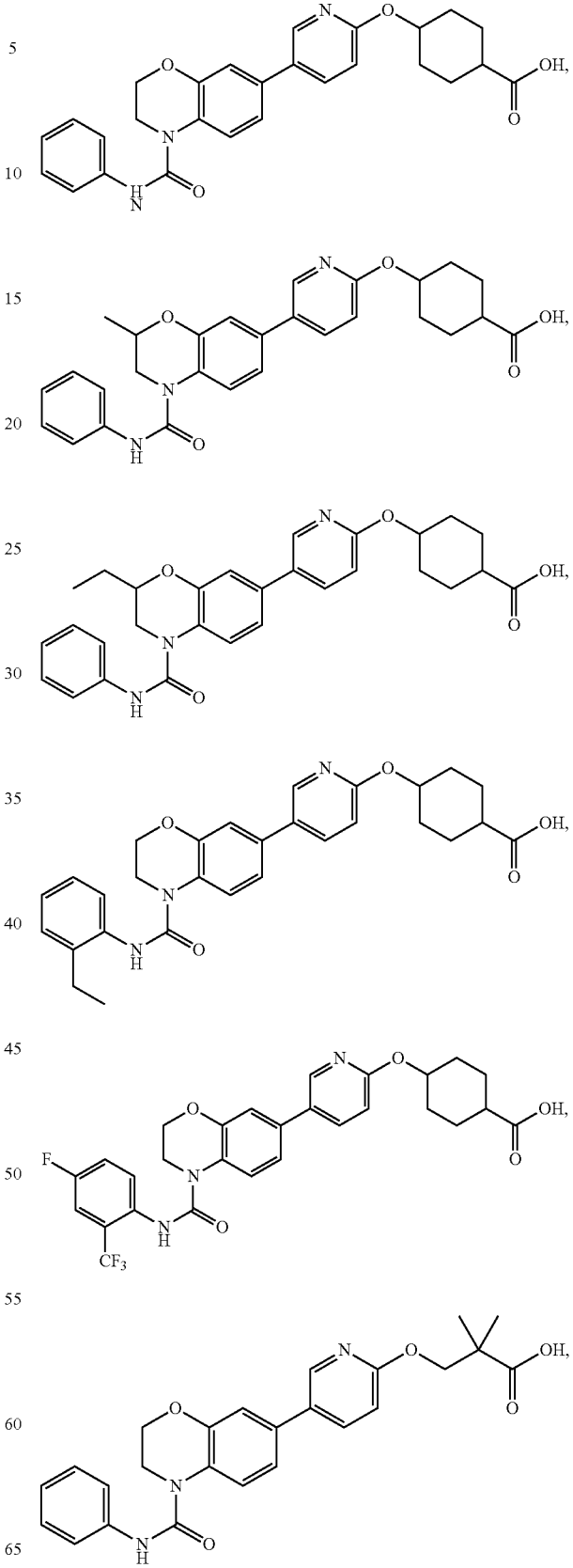

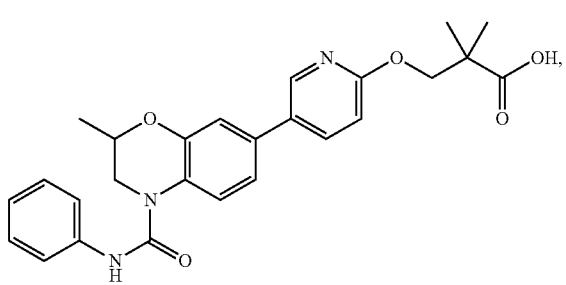
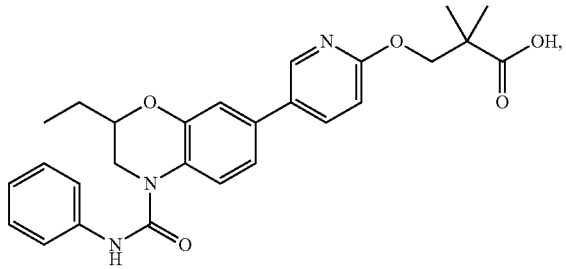
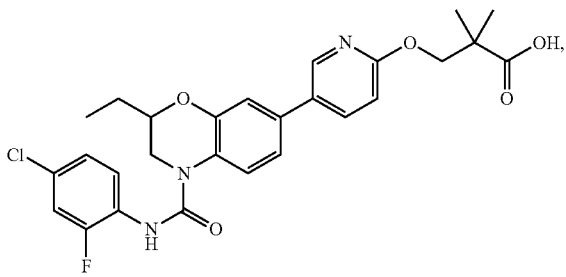
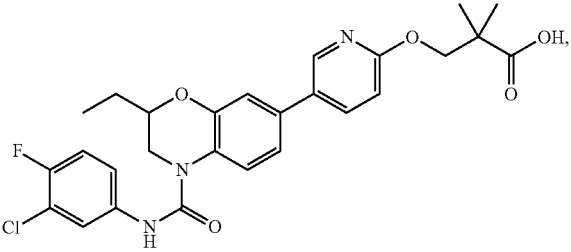
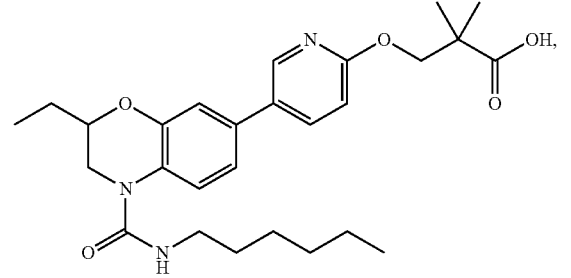
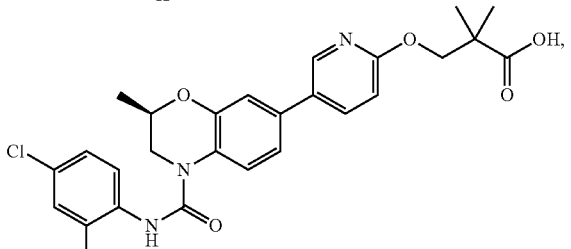
or a pharmaceutically acceptable salt thereof.
* * * * *